(12) United States Patent
Taylor et al.

US008124835B2

(10) Patent No.: US 8,124,835 B2
(45) Date of Patent: Feb. 28, 2012

(54) **ACYL-COA-DEPENDENT DIACYLGLYCEROL ACYLTRANSFERAS 1 (DGAT1) GENE FROM *TROPAEOLUM MAJUS*, PROTEIN ENCODED THEREBY AND USES THEREOF**

(75) Inventors: David C. Taylor, Saskatoon (CA); Jingyu Xu, Saskatoon (CA); Elzbieta Mietkiewska, Saskatoon (CA); Tammy Francis, Saskatoon (CA)

(73) Assignee: National Research Council of Canada, Ottawa, Ont.

( * ) Notice: Subject to any disclaimer, the term of this patent is extended or adjusted under 35 U.S.C. 154(b) by 354 days.

(21) Appl. No.: 12/309,134

(22) PCT Filed: Jul. 12, 2007

(86) PCT No.: PCT/CA2007/001225
§ 371 (c)(1),
(2), (4) Date: Jan. 8, 2009

(87) PCT Pub. No.: WO2008/006207
PCT Pub. Date: Jan. 17, 2008

(65) Prior Publication Data
US 2009/0293145 A1    Nov. 26, 2009

Related U.S. Application Data

(60) Provisional application No. 60/830,337, filed on Jul. 13, 2006.

(51) Int. Cl.
*A01H 1/00* (2006.01)
*A01H 5/00* (2006.01)
*C07K 14/415* (2006.01)
*C12N 5/04* (2006.01)
*C12N 5/14* (2006.01)

(52) U.S. Cl. ........ 800/278; 800/281; 800/306; 800/312; 800/314; 800/322; 530/370; 435/419; 435/468

(58) Field of Classification Search ....................... None
See application file for complete search history.

(56) References Cited

U.S. PATENT DOCUMENTS

| 6,051,755 | A | 4/2000 | Zou et al. |
| 7,015,373 | B1 | 3/2006 | Zou et al. |
| 2003/0074695 | A1 | 4/2003 | Farese, Jr. |

FOREIGN PATENT DOCUMENTS
EP    1746149    1/2007

OTHER PUBLICATIONS

Mietkiewska et al, Database GenEmbl, Accession No. AY084052, Jun. 8, 2005.*
Et al, Plant Physiology, Jun. 2001, vol. 126, pp. 861-874.*
Altschul SF, Gish W, Miller W, Myers EW, Lipman DJ (1990) Basic local alignment search tool. J.Mol.Biol. 215: 403-410.
Banas A, Dahlqvist A, Stahl U, Lenman M, Stymne S (2000) The involvement of phospholipid:diacylglycerol acyltransferases . . . Biochem.Soc.Trans. 28: 703-705.
Billheimer JT, Cromley DA, Kempner ES (1990) The Functional Size of Acyl-coenzyme A (CoA):Cholesterol Acyltransferase and Acyl-CoA . . . J. Biol. Chem. 265: 8632-8635.
Bouvier-Nave P, Benveniste P, Oelkers P, Sturley SL, Schaller H (2000) Expression in yeast and tobacco of plant cDNAs encoding acyl CoA . . . Eur. J. Biochem. 267: 85-96.
Burg DA, Kleiman R (1991) Preparation of meadowfoam dimer acids and mider esters and their use as lubricants. Journal of the American Oil Chemists' Society 68: 600-603.
Cahoon EB, Marillia EF, Stecca KL, Hall SE, Taylor DC, Kinney AJ (2000) Production of fatty acid components of meadowfoam oil in somatic . . . Plant Physiol. 124: 243-251.
Cases S, Smith SJ, Zheng YW, Myers HM, Lear SR, Sande E, Novak S . . . (1998) Identification of a gene encoding an acyl CoA . . . PNAS 95: 13018-13023.
Chang TY, Chang CC, Cheng D (1997) Acyl-coenzyme A:cholesterol acyltransferase. Annu.Rev.Biochem. 66: 613-638.
Dahlqvist A, Stahl U, Lenman M, Banas A . . . (2000) Phospholipid:diacylglycerol acyltransferase: An enzyme that catalyzes the acyl-CoA-independent . . . PNAS 97: 6487-6492.
Erhan SM, Kleiman R, Isbell TA (1993) Estolides from meadowfoam oil fatty . . . Journal of the American Oil Chemists' Society 70: 461-465.
Fehling E, Murphy DJ, Mukherjee KD (1990) Biosynthesis of Triacylglycerols Containing Very Long Chain Monounsaturated . . . Plant Physiol. 94: 492-498.
Fehling E, Mukherjee KD (1991) Acyl-CoA elongase from a higher plant (*Lunaria annua*): metabolic intermediates . . . Biochim.Biophys.Acta 1082: 239-246.
Fehling E, Lessire R, Cassagne C, Mukherjee KD (1992) Solubilization and partial purification . . . Biochim.Biophys.Acta 1126: 88-94.
Focks N, Benning C (1998) wrinkled1: A novel, low-seed-oil mutant of Arabidopsis with a deficiency in the seed-specific . . . Plant Physiol. 118: 91-101.
Griffiths G, Stymne S, Stobart AK (1988) Phosphatidylcholine and its relationship to triacylglycerol biosynthesis in oil-tissues. Phytochemistry 27: 2089-2093.
Halford NG, Hardie DG (1998) SNF1-related protein kinases: global regulators of carbon metabolism in plants? Plant Molecular Biology 37: 735-748.
He X, Turner C, Chen GQ, Lin J-T, Mckeon TA (2004) Cloning and Characterization of a cDNA Encoding Diacylglycerol Acyltransferase from Castor Bean. Lipids 39: 311-318.
Hobbs DH, Lu C, Hills MJ. (1999) Cloning of a cDNA encoding diacylglycerol acyltransferase from *Arabidopsis thaliana* and its functional expression. FEBS, 452, 145-149.
Hogge LR, Taylor DC, Underhill EW (1991) Characterization of castor bean neutral lipids by mass . . . Journal of the American Oil Chemists' Society68: 863-868.
Ichihara K, Takahashi T, Fujii S (1988) Diacylglycerol acyltransferase in maturing safflower seeds: its influences on the fatty acid . . . Biochim.Biophys.Acta 958: 125-129.

(Continued)

*Primary Examiner* — Eileen B O Hara

(57) ABSTRACT

A diacylglycerol acyltransferase (DGAT1) gene from *Tropaeolum majus* encodes a DGAT1 polypeptide that regulates the production of triacylglycerols from diacylglycerols. Transformation of cells with the *Tropaeolum majus* DGAT1 (TmDGAT1) gene, or variants thereof, leads to changes in DGAT1 activity and alterations in oil and/or fatty acid content and/or seed weight. In particular, oil content, seed weight, erucic acid and/or trierucin content may be increased.

12 Claims, 12 Drawing Sheets

OTHER PUBLICATIONS

IPRP on PCT CA2007-001225, Nov. 14, 2008.
ISR-WO on PCT CA2007-001225, Oct. 24, 2007.
Mietkiewska, E. et al., NCBI Accession Nos. AY084052 and AAMo3340, Jun. 8, 2005.
Batra, N., Optimisation of Trierucin Content in Oilseed Rape. Ph.D. Dissertation, Sep. 21, 2005.
Jako C, et al. (2001) Plant Physiol 126: 861-874.
Kalscheuer R, et al. (2004) Appl Environ Microbiol 70: 7119-7125.
Katavic V, et al. (1995) Plant Physiol 108: 399-409.
Katavic V, et al. (2002) Eur J Biochem 269: 5625-5631.
Knutzon DS, et al. (1995) Plant Physiol 109: 999-1006.
Lardizabal KD, et al. (2001) J Biol Chem 276: 38862-38869.
Lassner MW, et al. (1995) Plant Physiol 109: 1389-1394.
Lehner R, Kuksis A (1996) Biosynthesis of triacylglycerols. Prog in Lipid Res 35: 169-201.
Lewin TM, Wang P, Coleman RA (1999) Analysis of amino acid motifs diagnostic for the sn-glycerol-3-phosphate acyltransferase reaction. Biochemistry 38: 5764-5771.
Lu CL, de Noyer SB, Hobbs DH, Kang J, Wen Y, Krachtus D, Hills MJ (2003) Plant Mol Biol 52: 31-41.
Mancha M, Stymne S (1997) Remodelling of triacylglycerols in microsomal preparations from developing castor bean (*Ricinus communis* L.) endosperm. Planta 203: 51-57.
Milcamps A, Tumaney AW, Paddock T, Pan DA, Ohlrogge J, Pollard M (2005) J Biol Chem 280: 5370-5377.
Murphy DJ, Vance J (1999) Mechanisms of lipid-body formation. Trends Biochem Sci 24: 109-115.
Nakai K, Kanehisa M (1992) A knowledge base for predicting protein localization sites in eukaryotic cells. Genomics 14: 897-911.
Nykiforuk CL, Furukawa-Stoffer TL, Huff PW, Sarna M, Laroche A, Moloney MM, Weselake RJ (2002) Biochim Biophys Acta 1580: 95-109.
Oelkers P, Behari A, Cromley D, Billheimer JT, Sturley SL (1998) J Biol Chem 273: 26765-26771.
Oo KC, Chew YH (1992) Diacylglycerol Acyltransferase in Microsomes and Oil Bodies of Oil Palm Mesocarp. Plant Cell Physiol 33: 189-195.
Perry HJ, Bligny R, Gout E, Harwood JL (1999) Phytochemistry 52: 799-804.
Perry HJ, Harwood JL (1993a) Changes in the lipid content of developing seeds of *Brassica napus*. Phytochemistry 32: 1411-1415, 1993 Issue 6.
Perry HJ, Harwood JL (1993b) Radiolabelling studies of acyl lipids in developing seeds of *Brassica napus*; use of [1-14C] acetate precursor. Phytochemistry 33: 329-333, May 13, 1993 vol. 33, Issue 2.
Persson B, Argos P (1997) Prediction of membrane protein topology utilizing multiple sequence alignments. J Protein Chem 16: 453-457.
Routaboul JM, Benning C, Bechtold N, Caboche M, Lepiniec L (1999) Plant Physiol and Biochem 37: 831-840.
Slocombe SP, Piffanelli P, Fairbairn D, Bowra S, Hatzopoulos P, Tsiantis M, Murphy DJ (1994) Plant Physiol 104: 1167-1176.
Stahl U, Carlsson AS, Lenman M, Dahlqvist A, Huang B, Banas W, Banas A, Stymne S (2004) Plant Physiol 135: 1324-1335.
Stobart K, Mancha M, Lenman M, Dahlqvist A, Stymne S (1997) Planta 203: 58-66.
Stoveken T, Kalscheuer R, Malkus U, Reichelt R, Steinbuchel A (2005) J Bacteriol 187: 1369-1376.
Taylor DC, Weber N, Hogge LR, Underhill EW, Pomeroy MK (1992) J Am Oil Chem Soc 69: 355-358.
Taylor DC, Barton DL, Giblin EM, MacKenzie SL, Van Den BC, McVetty P (1995) Plant Physiol 109: 409-420.
Wolters-Arts M, Lush WM, Mariani C (1998) Lipids are required for directional pollen-tube growth. Nature 392: 818-821.
Xue L, McCune LM, Kleppinger-Sparace KF, Brown MJ, Pomeroy MK, Sparace SA (1997) Plant Physiol 113: 549-557.
Zheng Z, Xia Q, Dauk M, Shen W, Selvaraj G, Zou J (2003) Plant Cell 15: 1872-1887.
Zou J, Wei Y, Jako C, Kumar A, Selvaraj G, Taylor DC (1999) Plant J 19: 645-653.
Sandager L, et al. (2002) The Journal of Biological Chemistry 277(8): 6478-6482.
Marilla E-F, et al. (2002) Plant Physiol. Biochem. 40: 821-828.
Lindstrom JT, Vodkin LO (1991) The Plant Cell 3: 561-571.
The Durk Pearson & Sandy Shaw (2003) Life Extension News. vol. 6, No. 1.
Yamamoto K, et al. (2006) Diabetes Care 29(2); 417-419.
Bonaldo MF, Lennon G, Soares MB (1996) Normalization and Subtraction: Two Approaches to Facilitate Gene Discovery. Genome Research 6: 791-806.
Bradford MM (1976) Anal Biochem 72: 248-254.
Brough CL, Coventry JM, Christie WW, Kroon JTM, Brown AP, Barsby TL, Slabas AR (1996) Molecular Breeding 2: 133-142.
Cao J, Li J-L, Li D, Tobin JF, Gimeno RE (2006) Proc. Nat'l Acad Sci. 103: 19695-19700.
Cao YZ, Huang AHC (1987) Acyl Coenzme A preference of diacylglycerol acyltransferase from maturing sees of *Cuphea*, maize, rapeseed and canola. Plant Physiol. 84: 762-765.
Cao YZ Huang AHC (1986) Plant Physiol. 82: 813-820.
Cao YZ, Oo K-C, Huang AHC (1990) Lysophosphatidic acid acyltransferase in the microsomes from maturing seeds of meadowfoam (*Limnanthes alba*). Plant Physiol 94: 1199-1206.
Clough SJ, Bent AF (1998) Floral dip: a simplified method for Agrobacterium-mediated transformation of *Arabidopsis thaliana*. Plant J 16: 735-743.
Daniel J, Deb C, Dubey VS, Sirakova TD, Abomoelak B, Morbidoni HR, Kolattukudy PE (2004) J Bacteriol 186: 5017-5030.
DeBlock M, DeBrouwer D, Tenning P (1989) Plant Physiol 91: 694-701.
Guo Z, Cromley D, Billheimer JT, Sturley SL (2001) J Lipid Res 42: 1282-1291.
Ichihara K, Asahi T, Fugii S (1987) Eur J Biochem 167: 339-347.
Jadhav A, Katavic V, Marillia E-F, Giblin EM, Barton DL, Kumar A, Sonntag C, Babic V, Keller WA and Taylor DC (2005) Metabolic Engineering 7: 215-220.
Katavic V, Friesen W, Barton DL, Gossen KK, Giblin EM, Luciw T, An J, Zou J, MacKenzie SL, Keller WA, Males D, Taylor DC (2000) Biochem. Soc. Trans. 28(6): 935-937.
Koncz C, Schell J (1986) Mol Gen Genet 204: 383-396.
Larsen MR, Thingholm TE, Jensen ON, Roepstorff P, Jorgensen TJD (2005) Molecular and Cellular Proteomics 4: 873-866.
Laurent P, Huang AHC (1992) Organ- and development-specific acyl coenzyme A lysophosphatidate acyltransferases in palm and meadowfoam. Plant Physiol 99: 1711-1715.
Li Y, Beisson F, Pollard M, Ohlrogge J (2006) Oil content of *Arabidopsis* seeds: The influence of seed anatomy, light and plant-to-plant variation. Phytochemistry. 67: 904-15.
Lung A-C, Weselake RJ (2006) Diacylglycerol acyltransferase: A key mediator of plant triacylglycerol synthesis. Lipids. 41: 1073-1088.
Mhaske M, Beljilali K, Ohlrogge J, Pollard M (2005) Plant Physiol Biochem. 43:413-417.
Mietkiewska E, Giblin EM Wang S, Barton DL, Dirpaul J, Brost JM, Katavic V and Taylor DC (2004) Plant Physiol 136: 2665-2675.
Moloney MM, Walker JM, Sharma KK (1989) High efficiency transformation of *Brassica napus* using Agrobacterium vectors. Plant Cell Reports 8: 238-242.
Polge C, Thomas M (2006) SNF1/AMPK/SnRK1 kinases, global regulators at the heart of energy control. Trends in Plant Science 12: 20-28.
Pollard MR, Stumpf PK (1980) Long Chain (C20 and C22) Fatty Acid Biosynthesis in Developing Seeds of *Tropaeolum majus*. Plant Physiol 66: 641-648.
Saha S, Enugutti B, Rajakumari S, Rajasekharan R (2006) Plant Physiol 141:1533-1543.
Sambrook J, Fritsch EF, Maniatis T (1989) Molecular Cloning, A Laboratory Manual, Ed 2. Cold Spring Harbor Laboratory Press, Cold Spring Harbor, NY.
Shockey JM, Gidda SK, Chapital DC, Kuan JC, Dhanoa PK, Bland JM, Rothstein SJ, Mullen RT, Dyer JM (2006) Plant Cell 15: 1872-1887.
Tang GQ, Novitzky WP, Carol Griffin H, Huber SC, Dewey RE (2005) Plant J 44: 433-446.
Taylor DC, Weber N, Barton DL, Underhill EW, Hogge LR, Weselake RJ, Pomeroy MK (1991) Plant Physiol 97: 65-79.

Taylor DC, Barton DL, Rioux KP, MacKenzie SL, reed DW, Underhill EW, Pomeroy MK, Weber N (1992) Plant Physiol 99: 1609-1618.

Taylor DC, Katavic V, Zou J, MacKenzie SL, Keller WA, An J, Friesen W, Barton DL, Gossen KK, Giblin EM, Ge Y, Dauk M, Luciw T, Males D (2001) Molecular Breeding 8: 317-322.

Vigeolas H, Waldeck P, Zank T, Geigenberger P (2007) Plant Biotechnology Journal 5: 431-441.

Vyetrogon K, Tebbji F, Olson DJH, Ross ARS, Matton DP (2007) Proteomics 7: 232-247.

Wan L, Ross ARS, Yang J, Hegedus DD, Kermode AR (2007) Biochemical Journal 404: 247-256.

Weselake RJ, et al. (2006) BMC Biochemistry 7:24 (URL-http://www.biomedcentral.com/1471-2091/7/24).

Yamada K, Lim J, Dale JM, Chen H, Shinn P, Palm CJ, Southwick AM, Wu HC, Kim C, Nguyen M, et al (2003) Science 302: 842-846.

Zimmermann P, Hirsch-Hoffmann M, Hennig L, Gruissem W (2004) GENEVESTIGATOR. *Arabidopsis* microarray database and analysis toolbox. Plant Physiol 136: 2621-2632.

Zou J-T, Brokx SJ, Taylor DC (1996) Plant Mol Biol 31: 429-433.

Zou J-T, Katavic V, Giblin EM, Barton DL, MacKenzie SL, Keller WA, Hu X and Taylor DC (1997) Plant Cell 9: 909-923.

Löhden and Frentzen (1992) Triacylglycerol biosynthesis in developing seeds of *Tropaeolum majus* L. and *Limnanthes douglasii* R. Br. Planta 188:215-224.

Taylor DC, et al. (1990) In: Sixth Crucifer Genetics Workshop Proceedings, (McFerson JR, et al, eds), USDA-ARS Plant Genetic Resources Unit, Cornell University, pp. 38-39.

Wang HW, Zhang JS, Gai JY, Chen SY (2006) Theor Appl Genet. 112: 1086-1097.

Wang CS, Vodkin LO (1994) Extraction of RNA from Tissues Containing High Levels of Procyanidins that Bind RNA. Plant Mol Bio Rep 12: 132-145.

Taylor DC, Kunst L MacKenzie SL In: Progress in New Crops, (Janick J, Simon JE eds) Wiley, New York, pp. 181-191, 1993.

Weier D, et al. (1997) Trierucoylglyccerol biosynthesis in transgenic plants of rapeseed (*Brassica napus* L.) Fett/Lipid 99: 160-165.

Weselake RJ, et al. (2007) In: Current advances in the Biochemistry and Cell Biology of Plant Lipids. (Benning, eds.) Proc. of the 17th Int. Symp. on Plant Lipids, pp. 232-234.

Weselake RJ (2005) Storage lipids in Plant Lipids, Biology, Utilisation and Manipulation. Murphy DJ (ed.), Blackwell Publishing Ltd, Cardiff, UK, pp. 162-225.

Stymne S. et al. (1987) Triacylglycerol biosynthesis. The Biochemistry of Plants, vol. 9 Lipids: Structure and Function. PK Stumpf, ed, Academic Press, New York, pp. 175-214.

Katavic V, Zou J, Jako C, Marillia EF, Taylor DC (2001) Recent Res Devel Plant Biol 1: 131-142.

Taylor DC, et al. In: Seed Oils for the Future, (MacKenzie, et al. eds.) American Oil Chemists' Society, Champaign, IL., pp. 77-102, 1993.

Munster, G et al. (1998) Experiments to Optimise the Channelling of Erucic Acid into the sn-2 Position of Transgenic . . . , Advances in Plant Lipid Research, 671-674.

Frentzen, M., (1993) Acyltransferases and Triacylglycerols, Lipid Metabolism in Plants, 195-230.

\* cited by examiner

ID-DEPENDENT
DIACYLGLYCEROL ACYLTRANSFERAS 1
(DGAT1) GENE FROM *TROPAEOLUM MAJUS*,
PROTEIN ENCODED THEREBY AND USES
THEREOF

CROSS-REFERENCE TO RELATED APPLICATIONS

This application is a national entry of International application PCT/CA2007/001225 filed on Jul. 12, 2007 and claims the benefit of U.S. provisional patent application 60/830,337 filed Jul. 13, 2006, the entire contents of which are hereby incorporated by reference.

FIELD OF THE INVENTION

The present invention relates to the field of biochemistry. More particularly, the present invention relates to diacylglycerol acyltransferase genes, proteins encoded thereby and uses thereof.

BACKGROUND OF THE INVENTION

The main storage lipids in plants are triacylglycerols (TAGs) which are present in most plant organs: developing seeds, flower petals, anthers, pollen grains, and fruits (Stymne and Stobart, 1987; Oo and Chew 1992; Xue et al., 1997; Murphy and Vance, 1999). TAGs are thought to be not only the major energy source for seed germination but also essential for pollen development and sexual reproduction in many plants (Slocombe et al., 1994; Wolters-Arts et al., 1998; Zheng et al., 2003). TAG bioassembly is catalyzed by the membrane-bound enzymes of the Kennedy pathway that operate in the endoplasmic reticulum (Stymne and Stobart, 1987). The process begins with sn-glycerol-3-phosphate (G3P) undergoing two acylations catalyzed by the acyltransferases glycerol-3-phosphate acyltransferase (GPAT; EC 2.3.1.15) and lysophosphatidic acid acyltransferase (LPAAT; EC 2.3.1.51) The final acylation of sn-1,2-DAG by diacylglycerol acyltransferase (DGAT; EC 3.2.1.20) to give TAG, occurs after removal of the phosphate group from the sn-3 position of the glycerol backbone by phosphatidate phosphatase (PAPase; EC 3.1.3.4). It has been suggested that DGAT may be one of the rate-limiting steps in plant storage lipid accumulation (Ichihara et al., 1988; Perry and Harwood, 1993a & b; Perry et al., 1999; Jako et al., 2001; Weselake R J, 2005; Lung and Weselake, 2006), and thus a potential target in the genetic modification of plant lipid biosynthesis in oilseeds for economic benefit.

In the traditional Kennedy pathway DGAT is the only enzyme that is exclusively committed to TAG biosynthesis using acyl-CoA as its acyl donor. The first DGAT gene was cloned from mouse and is a member of the DGAT1 family, which has high sequence similarity with sterol:acyl-CoA acyltransferase (Cases et al., 1998). A second family of DGAT genes (DGAT2) was first identified in the oleaginous fungus *Morteriella ramanniana*, which has no sequence similarity with DGAT1 (Lardizabal et al., 2001). A novel class of acyl-CoA-dependent acyltransferases, wax ester synthase/acyl-CoA:diacylglycerol acyltransferase (WS/DGAT) was recently identified and purified from the bacterium *Acinetobacter* sp. strain ADP1, which can utilize both fatty alcohols and diacylglycerols as acyl acceptors to synthesize wax esters and TAGs, respectively (Kalscheuer and Steinbuchel, 2004; Stoveken et al., 2005). Other proposed additions to the traditional scheme of the Kennedy pathway include demonstrations that in developing castor and safflower seeds, TAG can also be generated from two molecules of DAG via a DAG:DAG transacylase (with MAG as a co-product) and that the reverse reaction participates in remodeling of TAGs (Lehner and Kuksis, 1996; Mancha and Stymne, 1997; Stobart al, 1997). In some species, it is apparent that TAG can also be formed by an acyl-CoA-independent enzyme, phosphatidylcholine:diacylglycerol acyltransferase (PDAT), in which the transfer of an acyl group from the sn-2 position of PC to the sn-3 position of DAG yields TAG and sn-1 lyso-PC (Dahlqvist et al, 2000; Banas et al., 2000). The two closest homologs to the yeast PDAT gene have been identified in *Arabidopsis* (Stahl et al, 2004). These findings suggest that these other TAG synthesizing enzymes may regulate the TAG biosynthesis at different stages of seed development or in different cellular compartments. It is not yet clear to what extent these enzymes may play a role in conventional TAG assembly in oilseeds. For example, Mhaske et al (2005) isolated and characterized a knockout mutant of *Arabidopsis thaliana* L. which has a T-DNA insertion in PDAT locus At5g13640 (PDAT, EC 2.3.1.158). Lipid analyses were conducted on these plants to assess the contribution of the PDAT gene to lipid composition; surprisingly, the fatty acid content and composition in seeds did not show significant changes in the mutant. This is a contrary situation to yeast where PDAT is a major contributor to triacylglycerol (TAG) accumulation in exponential growth phase. The results were interpreted to indicate that PDAT activity as encoded by At5g13640 is not a major determining factor for TAG synthesis in *Arabidopsis* seeds. Nonetheless, these other TAG synthesizing enzymes may regulate TAG biosynthesis at different stages of seed development or in different cellular compartments (Marianne et al., 2002).

We previously characterized an EMS-induced mutant of *Arabidopsis*, designated AS11, which displayed a decrease in stored TAG and an altered fatty acid composition (Katavic et al., 1995). Since the first identification of the DGAT1 gene from *Arabidopsis* (Zou et al., 1999; Hobbs et al., 1999; Routaboul et al., 1999), homologous DGAT1 genes from several other plants have been cloned (Bouvier-Nave et al, 2000; Nykiforuk et al., 2002; He et al., 2004; Milcamps et al., 2005; Wang et al., 2006; Saha et al., 2006; Shockey et al., 2006). Studies on these genes showed that the DGAT1 plays a dominating role in determining oil accumulation and fatty acid composition of seed oils. Thus, there was implied utility in manipulating the expression of this gene for improving oil content and perhaps, altering fatty acid composition. To this end, we demonstrated that expression of the *Arabidopsis* DGAT1 cDNA in a seed specific manner in the AS11 mutant restored wild type levels of TAG and VLCFA content. The acyl distribution i.e. the sn-3 composition of the TAGs was also restored to WT. Furthermore, over-expression of the *Arabidopsis* DGAT1 in wild type plants led to an increase in seed oil content and seed weight (Jako et al., 2001).

Oilseeds produce a variety of chemically unusual fatty acids that are currently used as industrial feedstocks. Erucic acid ($22:1^{\Delta 13}$) is one such fatty acid, and high erucic acid rapeseed (HEAR) is grown as an industrial feedstock crop on the Canadian prairies. The industrial applications of high erucic acid seed oils and their derivatives include lubricants, slip-promoting agents (in the manufacture of plastic films), nylon 1313, plasticizers, coating agents, photographic developers etc. (Taylor et al., 2001) The current market for high erucic oils exceeds $120M U.S./annum. Consistent with the market trends predicted by Sonntag (1995), since 1990, worldwide erucic acid demand has almost doubled and is predicted to reach 80 million pounds by the year 2010. Similarly, demand for the derivative behenic acid is predicted to triple to about 102 M pounds by 2010. Similarly, demand for the derivative, behenic acid, is predicted to triple to about 102 M pds by 2010. In recent years, production has increased to meet market needs, and high erucic acreage in western Canada is currently at a record high (D. Males, Saskatchewan Wheat Pool, personal communication). A *Brassica* cultivar containing erucic acid levels approaching 80% would significantly reduce the cost of producing erucic acid and its derivatives, and could meet the forecast demand for erucic and behenic acids as renewable, environmentally friendly industrial feedstocks (Leonard, 1994; Taylor et al., 2001; Mietkiewska et al., 2004). For this reason, improving the erucic acid content of HEAR Brassicaceae is of interest in a biotechnology context. Erucic acid is synthesized by successive 2-carbon extensions of oleic acid donated from malonyl-CoA by the action of an elongase complex (Katavic et al., 2001).

The only plant known to accumulate trierucin in its seed oil is garden nasturtium (*Tropaeolum majus*). Although the total oil content of the seed is only 8-15%, erucic acid constitutes 70-75% of the total fatty acid composition and most of this is in the form of trierucin (Pollard and Stumpf, 1980, Taylor et al., 1992).

There is a need in the art to isolate a gene from *Tropaeolum majus* that encodes the DGAT1 protein.

SUMMARY OF THE INVENTION

In accordance with the present invention, there is provided an isolated, purified or recombinant nucleic acid molecule comprising a nucleotide sequence of SEQ ID NO: 2, a nucleotide sequence having 98% or greater nucleotide identity to SEQ ID NO: 2, or a complementary nucleotide sequence thereof.

There is further provided an isolated or purified polypeptide comprising an amino acid sequence of SEQ ID NO: 3 or an amino acid sequence having 98% or greater amino acid identity to SEQ ID NO: 3.

There is yet further provided a vector, host cell, seed or plant transformed with a nucleic acid molecule of the present invention.

There is yet further provided a method of altering oil and/or fatty acid content in a cell comprising: expressing or over-expressing a nucleic acid molecule of the present invention in the cell to increase or decrease expression of a diacylglycerol acyltransferase.

There is yet further provided a method of altering seed weight comprising: expressing or over-expressing a nucleic acid molecule of the present invention in the seed to increase or decrease expression of a diacylglycerol acyltransferase.

There is yet further provided a method comprising: converting a diacylglycerol to a triacylglycerol in the presence of an acyl donor and a diacylglycerol acyltransferase comprising a polypeptide of the present invention.

There is yet further provided a method of altering diacylglycerol acyltransferase activity in a cell comprising: expressing or over-expressing the polypeptide of the present invention in the cell.

Here we disclose the cloning and broad characterization of a diacylglycerol acyltransferase (DGAT1) from *T. majus*. We show the utility of the TmDGAT1 to enable the production of oilseed plants with enhanced oil and/or fatty acid content and/or seed weight, and of the recombinant gene product to synthesize trierucin. For the first time, we have conducted site-directed mutagenesis (SDM) studies on a plant DGAT1. Six independent putative functional motifs were modified via SDM. These studies reveal the utility of targeted changes in enzyme motifs to enable up- or down-regulation of DGAT1 activity providing a new means to effect changes in seed development, oil content, fatty acid content and/or seed weight.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Figure 1A:
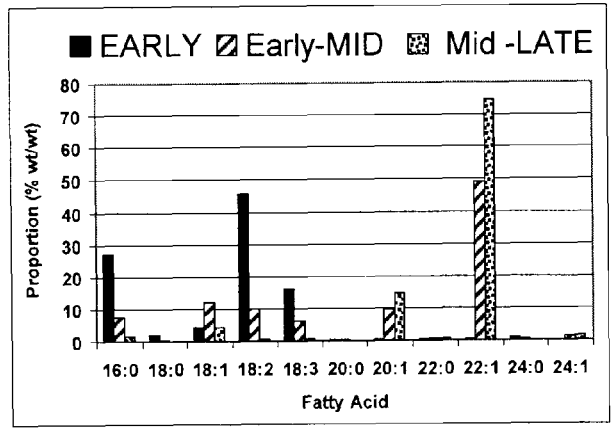
FIG. 1. (A) Fatty acid composition in developing *T. majus* seed. (B) TAG accumulation in developing *T. majus* seed. (C) DGAT activity in developing *T. majus* seed. The following were the designated stages of embryo development in days post anthesis: Early: 8-15 d.p.a.; Early-mid: 16-20 d.p.a.; Mid: 22-27 d.p.a.; Mid-late: 27-30 d.p.a.; Mature: 38 d.p.a. Total FAMEs, Oil content and DGAT activity were measured as described in "Materials and Methods". DGAT activity was measured in the presence of paired acyl-CoA and sn-1,2 DAG containing the same acyl groups.

All technical terms employed in this specification are commonly used in biochemistry, molecular biology and agriculture; hence, they are understood by those skilled in the field to which this invention belongs. Those technical terms can be found, for example in: *Molecular Cloning: A Laboratory Manual* 3rd ed., vol. 1-3, ed. Sambrook and Russel, Cold Spring Harbor Laboratory Press, Cold Spring Harbor, N.Y., 2001; *Current Protocols in Molecular Biology*, ed. Ausubel et al., Greene Publishing Associates and Wiley-Interscience, New York, 1988 (including periodic updates); *Short Protocols in Molecular Biology: A Compendium of Methods from Current Protocols in Molecular Biology* 5th ed., vol. 1-2, ed.

Ausubel et al., John Wiley & Sons, Inc., 2002; *Genome Analysis: A Laboratory Manual*, vol. 1-2, ed. Green et al., Cold Spring Harbor Laboratory Press, Cold Spring Harbor, N.Y., 1997. Methodology involving plant biology techniques are described here and also are described in detail in treatises such as *Methods in Plant Molecular Biology: A Laboratory Course Manual*, ed. Maliga et al., Cold Spring Harbor Laboratory Press, Cold Spring Harbor, N.Y., 1995.

The term "altering" in respect of oil content, fatty acid content or seed weight refers to changing the level of one or more of these properties relative to the level for a non-transformed cell, tissue or whole organism. An altered level may be increased or decreased relative to the level in a non-transformed cell, tissue or whole organism.

The terms "encoding" and "coding" refer to the process by which a gene, through the mechanisms of transcription and translation, provides information to a cell from which a series of amino acids can be assembled into a specific amino acid sequence to produce an active enzyme. Because of the degeneracy of the genetic code, certain base changes in DNA sequence do not change the amino acid sequence of a protein.

As used herein, "expression" denotes the production of an RNA product through transcription of a gene or the production of the protein product encoded by a nucleotide sequence.

Over-expression" or "up-regulation" is used to indicate that expression of a particular gene sequence or variant thereof, in a cell or plant, including all progeny plants derived thereof, results in a DGAT enzyme whose activity has been increased by genetic engineering, relative to a control cell or plant.

The terms "suppression" or "down-regulation" are used synonymously to indicate that expression of a particular gene sequence, or variant thereof, in a cell or plant, including all progeny plants derived thereof, results in a DGAT enzyme whose activity has been reduced, relative to a control cell or plant.

Use in this description of a percentage of sequence identity denotes a value determined by comparing two optimally aligned sequences over a comparison window, wherein the portion of the polynucleotide or amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The present application is directed to nucleic acid molecules and polypeptides which are at least 98%, 99% or 100% identical to a nucleic acid sequence described in SEQ ID NO: 1 or SEQ ID NO: 2 or an amino acid sequence described in SEQ ID NO: 3. Preferred are nucleic acid molecules and polypeptides which are at least 99% or 100% identical to the nucleic acid sequence shown in SEQ ID NO: 1 or SEQ ID NO: 2 or the amino acid sequence shown in SEQ ID NO: 3. Differences between two nucleic acid sequences or two amino acid sequences may occur at the 5' or 3' terminal positions of the reference nucleotide or amino acid sequence or anywhere between those terminal positions, interspersed either individually among nucleotides or amino acids in the reference sequence or in one or more contiguous groups within the reference sequence.

Nucleic acid molecules of the present invention may be transformed into and/or expressed or over-expressed in cells, tissues and/or whole organisms. Tissues may be, for example, seed tissues of a plant. Organisms may be, for example, plants, animals (e.g. insects) or microorganisms (e.g. yeast). Plants of particular interest, and cells and tissues thereof, may include, for example, oilseed plants. Oilseed plants, include, for example, Brassicaceae spp. (e.g. rapeseed and Canola), *Borago* spp. (borage), *Ricinus* spp. (e.g. *Ricinus communis* (castor)), *Theobroma* spp. (e.g. *Theobroma cacao* (cocoa bean)), *Gossypium* spp. (cotton), *Crambe* spp., *Cuphea* spp., *Linum* spp. (flax), *Lesquerella* spp., *Limnanthes* spp., *Linola*, *Tropaeolum* spp. (nasturtium), *Olea* spp. (olive), *Elaeis* spp. (palm), *Arachis* spp. (peanut), *Carthamus* spp. (safflower), *Glycine* spp. (soybean), *Soja* spp. (soybean), *Helianthus* spp. (sunflower), *Vernonia* spp. Oilseed plants of particular note are from the family Brassicaceae, especially *Arabidopsis, Brassica napus, Brassica rapa, Brassica carinata, Brassica juncea*, and *Camelina sativa*. Other plant species of interest include, for example, *Zea mays* (corn), *Oenothera* spp., *Nicotiana* spp. (e.g. tobacco), *Triticum* spp. (e.g. wheat), *Hordeum* spp. (e.g. barley), *Oryza* spp. (e.g. rice), *Avena* spp. (e.g. oat), *Sorghum* spp. (e.g. sorghum), *Secale* spp. (e.g. rye) and other members of the Gramineae.

Materials and Methods:

Plant Materials and Growth Conditions

*Tropaeolum majus* seeds (cultivar Dwarf Cherry Rose) were obtained from Early's Farm and Garden Centre, Saskatoon, SK, and were grown at the Kristjanson Biotechnology Complex greenhouses, Saskatoon, under natural light conditions supplemented with high-pressure sodium lamps with a 16 h photoperiod (16 h of light and 8 h of darkness) at 22° C. and a relative humidity of 25 to 30%. Flowers were hand-pollinated and seeds at various stages of development were harvested, their seed coats were removed and embryos were frozen in liquid nitrogen and stored at −80° C. In a similar fashion other plant tissues (roots, leaves, flower petals) were harvested and stored. *Arabidopsis* plants were grown in a growth chamber at 22° C. with photoperiod of 16 h light (120 µE·m$^{-2}$·s$^{-1}$) and 8 h dark, and where necessary, developing seeds harvested as described previously (Katavic et al., 1995). Determination of the lipid composition of developing nasturtium embryos at various stages of development was conducted on freeze-dried material. The following were the designated stages of embryo development in days post anthesis: Early: 8-12 d.p.a.; Early-mid: 13-20 d.p.a.; Mid: 22-27 d.p.a.; Mid-late: 27-30 d.p.a.; Mature: 35 d.p.a.

Analysis of Oil Accumulation, DGAT Activity, DAG, TAG and Overall Fatty Acid Composition in Developing *Tropaeolum majus* Embryos Nasturtium embryos of early, mid and late stages, as well as mature seed were weighed and transferred to a cooled mortar and ground in 2 ml IPA:CH$_2$Cl$_2$ (2:1), the mixture was transferred to a test tube; to this was added the above solvent (1 ml) and 0.9% NaCl (1 ml) and vortexed. 2 ml CH$_2$Cl$_2$ was added, the mixture re-vortexed and centrifuged at 2500 r.p.m. for 3 min. The CH$_2$Cl$_2$ layer was removed, the extraction repeated and the CH$_2$Cl$_2$ layers combined. CH$_2$Cl$_2$:Benzene:Methanol (1:1:1) (1 ml) was added and then the sample evaporated to dryness. The dried sample was re-suspended in CHCl$_3$ (1 ml) to give the total lipid extract (TLE).

The developmental acyl composition of the TLE and the total oil content at each stage were determined by transesterification followed by GC using tri-15:0 as an internal standard and tri-17:0 as an external standard (to determine completeness of transmethylation) as described previously (Mietkiewska et al., 2004). The DAGs and TAGs were recovered by running the TLE on a Silica G TLC plate developed in Hexane:Diethyl Ether:Acetic acid (70:30:1). The TAG and DAG regions on the TLC plate were scraped and silicates extracted in CHCl$_3$:Acetone (96:4) (3×2 mls), evaporated to dryness and dissolved in CHCl$_3$.

The individual molecular species of DAGs in the mid stage, and TAGs at all three stages, were resolved by HPLC in acetonitrile:acetone. HPLC fractionation of TAGs and DAGs was conducted on an Agilent 1100 HPLC fitted with a Partisphere C18 4.6×12.5 cm HPLC column (Whatman) and an evaporative light scattering detector (ELSD) (ACS). HPLC conditions: Solvent A: Acetonitrile; Solvent B: Acetone; Gradient program: 0 min-50% A:50% B; 4 min-40% A:60% B; 20 min-35% A:65% B; 30 min-0% A:100% B; 40 min-0% A: 100% B; 50 min-50% A: 50% B. Column Temperature 40° C.; Two HPLC runs were performed: in the 1st run, peaks were detected by ELSD; in the 2nd run, fractions were collected by time for MALDI analyses.

The TAG and DAG species from the HPLC fractionation were analyzed by MALDI-Q tof MS/MS mass spectrometry on a Voyager-DE STR (Applied Biosystems) using pencil lead as the MALDI matrix to enhance production of cationized molecular ions in the full scan, and to evaluate Post Source Decay (PSD) of these ions for structural determination. TAGs and DAGs were overspotted on a MALDI plate with the pencil lead matrix: a 6B General's SEMI-HEX DRAWING Pencil was gently scribbled inside the well on the plate and then sample (0.75 µl) was placed on top of the well and air dried.

MALDI-TOF MS/MS spectra were acquired in positive ion and linear modes from m/z 500-1200 (full scan). Laser power was initially set at 2100 for pencil lead, and adjusted as required to maximize signal. For PSD acquisitions with pencil lead, the laser power was increased until fragmentation occurred (typically ~2400). Two mirror ratios were used, one for the precursor mass and one in the expected region of the fragment ions, and the spectra stitched together using the instrument software (Data Explorer). The instrument was calibrated using the sodiated molecular ions for Trierucin (Tri-22:1; m/z 1075.960) and Dierucin (Di-22:1; m/z 755.652). PSD of the standards showed the expected losses of the acyl groups from the sodiated molecular ion. Similarly, PSD of the sodiated ions of HPLC-fractionated nasturtium TAGs and DAGs also resulted in the loss of specific acyl and of [acyl+Na] groups.

Isolation of the TmDGAT1 cDNA by a Degenerate Primers Approach

Degenerate primers were designed for amino acid sequences conserved among *Arabidopsis* and other known plant DGAT1s. A single-stranded cDNA template for reverse transcriptase-PCR was synthesized at 42° C. from embryo poly (A) RNA with PowerScript™ (Clontech, Palo Alto, Calif., USA). A 50 µL PCR reaction contained single-stranded cDNA derived from 40 ng of poly (A) RNA, 20 pM of each primer: 5'-TA(T/C)TT(T/C)ATGGTIGCICCIAC-3' (SEQ ID NO: 16) and 5'-GGCAT(A/G)TTCCACAT(T/C)C (T/G)CCA-3' (SEQ ID NO: 17) and 2.5 U of Taq DNA Polymerase (Amersham Biosciences, Quebec, Canada) under standard conditions. An internal part of the DGAT sequence was amplified in a thermocycler during 30 cycles of the following program: 94° C. for 30 s, 55° C. for 30 s, and 72° C. for 1 min. The sequence of a 380-bp PCR product was used to design a primer to amplify the 5' and 3' ends of the cDNA using the SMART™ RACE cDNA Amplification Kit (Clontech). After assembly of the full length sequence of the cDNA, the open reading frame (ORF) was amplified using the primers 5'-GAAATGGCGGTGGCAGAG-3' (SEQ ID NO: 18) and 5'-TCACTTTTCCTTTAGATTTATC-3' (SEQ ID NO: 19), and subsequently cloned into the pYES2.1/V5-His-TOPO expression vector (Invitrogen, Burlington, ON, Canada).

cDNA Library Construction and Normalization cDNA was synthesized from mRNA isolated from mid-developing nasturtium embryos using a cDNA synthesis kit (Stratagene). The cDNA was directionally cloned into the pBluescript SK II (+) vector (Stratagene) and transformed into DH10B electrocompetent cells. The primary library was amplified using semi-solid agar (SeaPrep agarose, Mandel). Normalization of the library was performed at $C_0t$ 2.5 and $C_0t$ 5 following the normalization method 4 of Bonaldo et al., 1997. Double stranded phagemid DNA is converted to single stranded DNA using Gene II protein and Exonuclease III (Genetrapper cDNA Positive Selection System, Gibco BRL, cat. no. 10356-020). The single stranded DNA is purified from the double stranded DNA using HAP chromatography (type II Hydroxyapatite, BioRad, cat. no. 158-4200).

Sequence Handling

Sequence analyses were performed using Lasergene software (DNAStar, Madison, Wis., USA). Sequence similarity searches and other analyses were performed using BLASTN, BLASTX (Altschul et al., 1990) and PSORT (Nakai and Kanehisa, 1992) programs.

Northern Analysis

Total RNA from *T. majus* plant material was isolated as described by Wang and Vodkin (1994). 20 µg of RNA was fractionated on a 1.4% formaldehyde-agarose gel and the gels were then stained with ethidium bromide to ensure that all lanes had been loaded equally (Sambrook et al., 1989). The RNA was subsequently transferred to Hybond N+ membrane (Amersham Biosciences) and hybridized with the $^{32}$P-labeled TmDGAT1 DNA probe, prepared using the Random Primers DNA labeling kit (Gibco-BRL, Cleveland, USA). Membranes were hybridized at 60° C. overnight.

Expression of TmDGAT1 in Sf9 Insect Cell Cultures

The coding region of TmDGAT1 (SEQ. ID. NO: 2) was sub-cloned into pFastBAC for expression of the protein in an insect cell expression system (Bac-to-Bac baculovirus expression system, Invitrogen). *Escherichia coli* DH10Bac cells were transformed with the construct to generate recombinant bacmid DNA, and then the bacmid DNA was isolated and used to transfect Sf9 insect cells. The virus stock harvested from the transfected cells was used to re-infect fresh Sf9 insect cells. Insect cells (2.5×10$^6$ per 25 cm$^2$ dish) were infected with virus and were collected at 48 h by centrifugation and washed twice with PBS (Hobbs et al., 1999). Cells were broken by grinding with a polytron for 45 seconds. Sample tubes were cooled on ice while grinding. Samples were then probe-sonicated on ice for 30 sec. Unbroken cells were removed from the cell lysate by low speed centrifugation (10,000×g for 20 min). The membrane particles isolated from the supernatant by ultracentrifugation (100,000×g, 60 min), were re-suspended in the homogenization buffer (in 0.32M sucrose, 50 mM KCl, 40 mM KH$_2$PO$_4$, and 30 mM EDTA (pH 7.2). Protein determination was performed using Biorad reagent, based on the method described by Bradford (1976).

DGAT assays were conducted at pH 7.4, with shaking at 100 rev/min in a water bath at 30° C. for 60 min. Assay mixtures (0.5 ml final volume) contained 500 µg lysate protein normalized as described above, 90 mM HEPES-NaOH, 0.5 mM ATP, 0.5 mM CoASH, 1 mM MgCl2, 200 µM sn-1,2 diolein (pre-purified by TLC on 10% borate silica H plates) in 0.02% Tween-20, and 18 µM [1-$^{14}$C] 18:1-CoA (specific activity 2 nCi/nmol) as the acyl donor. The $^{14}$C-labelled TAGs were isolated by TLC on silica gel G plates developed in hexane:diethyl ether:acetic acid (70:30:1 v/v/v/), the radiolabelled TAG bands visualized on a Bioscan AR-2000 radio-TLC scanner using Win-Scan 2D© software (Bioscan Inc., Washington D.C., USA) and the bands scraped and quantified as described by Taylor et al. (1991).

Expression of TmDGAT1 in Yeast

The TmDGAT1 ORF (SEQ. ID. NO: 2) in pYES2.1/V5-His-TOPO plasmid was transformed into a quadruple yeast mutant H1246MATα (Sandager et al, 2002) using the S.c. EasyComp™ transformation Kit (Invitrogen). Yeast cells transformed with pYES2.1/V5-His-TOPO plasmid only were used as a control. Transformants were selected by growth on synthetic complete medium lacking uracil (SC-ura), supplemented with 2% (w/v) glucose. The colonies were transferred into liquid SC-ura with 2% (w/v) glucose and grown at 28° C. overnight. The overnight cultures were diluted to an OD of 0.4 in induction medium (SC-ura+2% Galactose+1% Raffinose), and were induced for 24-36 hours at 28° C. Cells were collected and broken using glass beads. The crude protein concentration in the lysates was normalized using the Biorad assay based on the method of (Bradford, 1976) and assayed for DGAT activity. DGAT assays were conducted at pH 7.4, with shaking at 100 rev/min in a water bath at 30° C. for 60 min. Assay mixtures (0.5 ml final volume) contained 500 µg lysate protein normalized as described above, 90 mM HEPES-NaOH, 200 µM sn-1,2 diolein or sn-1,2 dierucin (pre-purified by TLC on 10% borate silica H plates) in 0.02% Tween-20, and 18 µM 1-$^{14}$C acyl-CoA (specific activity 2 nCi/nmol) as the acyl donor. The $^{14}$C-labelled TAGs were isolated and counted as described above for insect cell expression.

Plant Transformation Vectors

The coding region of the TmDGAT1 (SEQ. ID. NO: 2) was amplified by polymerase chain reaction with primers: F-forward: 5'-tatctagaATGGCGGTGGCAGAG-3' (SEQ ID NO: 20) (lower case-restriction site for XbaI) and R-reverse: 5'-atggtaccTCACTTTTCCTTTAGATTTATC-3' (SEQ ID NO: 21) (lower case shows restriction site for KpnI enzyme) and subsequently cloned behind the napin promoter in the respective sites of the pSE vector (Jako et al., 2001). The final binary vector (napin/DGAT/nos) was verified and electroporated into Agrobacterium tumefaciens cells strain GV3101 containing helper plasmid pMP90 (Koncz and Schell, 1986). Plasmid integrity was verified by DNA sequencing following its re-isolation from A. tumefaciens and transformation into E. coli.

Plant Transformation and Molecular Genetic Analysis of Transgenic Plants

Arabidopsis thaliana (ecotype Columbia) WT and mutant line AS11 (Katavic et al., 1995; Zou et al, 1999) were transformed by a vacuum infiltration method (Clough and Bent, 1998). B. napus HEAR breeding line 2026 (courtesy of Dr. P. B. E. McVetty, University of Manitoba) was transformed utilizing hypocotyl explants and a modified method of DeBlock et al., 1998. Modifications of the hypocotyl explant transformation method were described previously (Zou et al., 1997).

Transgenic plants were selected and analyzed essentially as described previously (Jako et al., 2001; Mietkiewska et al., 2004). DNA was isolated from 150 mg of Arabidopsis leaf material. Stable integration of the napin:DGAT:nos cassette into the genome of transgenic plants was checked by PCR amplification of genomic DNA as described by Mietkiewska et al., (2004).

Segregation analyses were performed to further confirm and select those transformants containing a single copy of the inserted fragment. Seeds from the Agrobacterium-transformed plants were plated on selective medium and kanamycin resistant $T_1$ plants were transferred to soil and their genotype characterized. Plants that contained the insertion (as shown by the presence of a PCR product from a napin/NOS junction using NN3 primer (5'-TTTCTTCGCCACTTGT-CACTCC-3'; SEQ ID NO: 22) and NN4 primer (5'-CGCGC-TATATTTTGTTTTCTA-3'; SEQ ID NO: 23) and that carry a single locus insertion (as determined by a 3:1 segregation ratio of $T_2$ seeds on kanamycin) were identified. Southern analyses were performed to further confirm and select those transformants containing single vs. multiple copies of the inserted fragment. DNA samples were digested with restriction enzymes KpnI (or BglII), resolved by electrophoresis on a 1% (w/v) agarose gel, and Southern blotting performed using a nylon filter (Hybond N+, Amersham) according to Sambrook et al. (1989). The TmDGAT cDNA fragment, labeled with [$^{32}$P]dCTP (Amersham Pharmacia Biotech in Canada, Quebec, Canada) using the Random Primer DNA labeling kit (Gibco-BRL, Cleveland), was used as a probe. Hybridization was performed at 65° C. according to Church and Gilbert (1984). The filter was then exposed to X-OMAT-AR film (Kodak, Rochester, N.Y.). RNA extraction and northern blots were conducted as described above "Northern analysis". 20 µg of RNA was loaded for each sample, and the TmDGAT1 DNA probe was $^{32}$P-labeled by random priming (Sambrook et al., 1989).

Lipid Analyses and DGAT1 Enzyme Assay of Transgenic Seeds

Total lipid extracts (TLEs) were prepared as described above, and lipid class analyses, determination of oil content and composition in all seed lines from WT and the AS11 transgenic plants and in nasturtium seed were performed as described previously (Taylor et al., 1991; 1992 a & b; Zou et al., 1997; Jako et al., 2001). In all cases, the data represent the averages of three to five determinations. Intact-seed transmethylation followed by gas chromatography (GC) analysis provided equally reproducible analyses of Arabidopsis seed oil as reported by Li et al., (2006).

About 200 Arabidopsis siliques containing mid-green developing seeds (pooled silique stages 3-6 inclusive, as described by Zou et al., 1996) or about 25 mid-developing B. napus seeds were harvested from pSE in WT control, and napin:TmDGAT1 transgenic lines and immediately powdered with liquid nitrogen in a mortar and pestle. Grinding medium (100 mM HEPES-KOH, pH 7.4 containing 0.32 M sucrose, 1 mM EDTA, and 1 mM dithiothreitol) was immediately added, and grinding continued on ice for 3 min. The slurried cell free homogenate was filtered through two layers of Miracloth (Calbiochem, La Jolla, Calif.). Protein determinations were performed using Biorad reagent and DGAT assays were conducted as described above for the insect cell expression experiments.

Site-Directed Mutagenesis Studies

To introduce point mutations into the Tropaeolum majus DGAT1 coding region, we used a QuikChange™ site-directed mutagenesis kit (Stratagene). We designed oligonucleotide primer pairs containing the desired mutations as indicated in Table 2. Primers were complementary to opposite strands of pYES2.1/V5-His TOPO yeast expression vector (Invitrogen) containing the TmDGAT1 gene. During the PCR, primers were extended with PfuTurbo DNA polymerase. This polymerase replicated both strands with high fidelity and without displacing the mutated oligonucleotide primers. The cycling parameters used for site-directed mutagenesis were as follows: initial denaturation at 95° C. for 30 s, followed by 15 cycles at 95° C. for 30 s, 55° C. for 1 min, and 68° C. for 15 min, with termination at 68° C. for 15 min.

Following the PCR reaction, the product was treated with DpnI endonuclease (target sequence: 5'-Gm6ATC-3') which is specific for methylated and hemimethylated DNA, used to digest the parental DNA template and to select for the mutated DNA. For western blotting purposes, the SDM TMDGAT1s were amplified out of the pYES2.1/V5-His yeast vector using 5' primer 5'-GAggtaccGGAAATGGCG-GTGGCAG-3' (SEQ ID NO: 24) (lower case shows KpnI restriction site) and 3' primer 5'-CCGctc-gagTTTCACTTTTCCTTTAGATTTATCAGG-3' (SEQ ID NO: 25) (lower case shows XhoI restriction site), and ligated into the pYES2/NT yeast expression vector at the KpnI and Xho I restriction sites. All TmDGAT1/pYES constructs were sequenced to verify that only the intended point mutations were present and that the genes were cloned in-frame with the epitope tags. The correct constructs were transformed into the quadruple mutant yeast strain H1246 MATα using the S.c. EasyComp™ transformation Kit (Invitrogen). Yeast cells transformed with pYES2/NT plasmid only were used as a control. The yeast transformants were grown for 7, 16, 24 or 36 hr in induction medium (SC-ura+2% Galactose+1% Raffinose) at 30° C. Under the control of the GALL promoter, the DGAT gene in the pYES2/NT yeast vector was expressed as an N-terminal fusion protein to the Xpress epitope and polyhistidine (6xHis) tag.

Immunodetection

The transformed and induced yeast cells were collected and broken using glass beads. The yeast lysate was centrifuged and a 15,000×g membrane pellet fraction was collected. The 15,000×g samples were run on a 10% Tris-HCl SDS-PAGE gel and the proteins were transferred to a nitrocellulose membrane (Nitrobind, Fisher). The membrane was blocked in PBST (phosphate buffered saline containing 0.5% Tween 20) containing 4% skim milk for 60 min, and then incubated with the primary antibody, Anti-Xpress antibody (Invitrogen) diluted to 1:5000 with PBST containing 2% skim milk, for 60 min. The membrane was submitted to three washes with PBST followed by three washes with PBS to remove any unbound antibody. Next, the membrane was incubated with a goat anti-mouse IgG peroxidase antibody (Sigma, A2554), diluted to 1:5000 with PBST containing 2% skim milk, for 60 min. The membrane was washed three times PBST and three times PBS, then the proteins were detected using the Amersham ECL Plus Western Blotting Detection Kit (GE Healthcare Life Sciences).

Figure 1B:
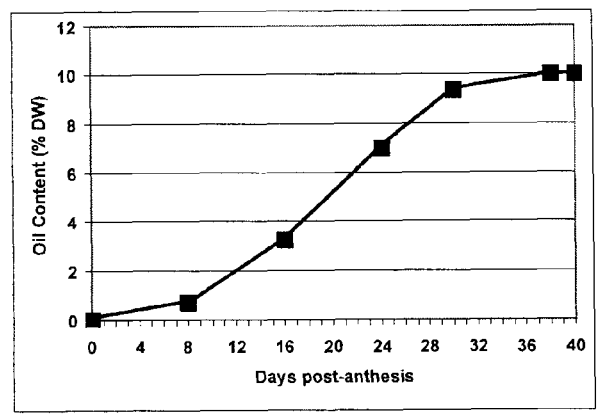

Results:

Neutral Lipid Accumulation, Fatty Acid Composition and DGAT Activity in *Tropaeolum majus* cv Dwarf Cherry Rose Developing Seed The acyl composition of the lipid fraction in developing embryos of this cultivar showed that in the early stages of development, the predominant fatty acids were those typically found in membrane lipids-18:2, 16:0, 18:3 and 18:1 (FIG. 1A). As the embryo entered mid-development, the acyl composition reflected the shift toward storage lipid deposition, with a drastic drop in proportions of 16:0, 18:2 and 18:3, and a rise in 18:1 and 20:1, the precursors of the now dominant 22:1. By late embryogenesis, the proportions of 18:1 and 20:1 shifted in favour of the latter, with the proportion of erucic acid representing 60% of the total fatty acyl makeup. At maturity, the acyl composition of the lipid fraction, predominantly TAGs, was similar to that reported previously (Taylor et al., 1993; Taylor, Kunst & MacKenzie, 1993) with highly enriched proportions of VLCMFAs, particularly 22:1 (75%) and 20:1 (1.5%) with a trace of 24:1 (1.6%), and a low proportion of total palmitate and C18 fatty acids (7%), primarily oleate (18:1 (9; 4.5%). Oil deposition exhibited a sigmoidal pattern typical of developing seed, with the highest rate occurring between 16 and 24 days post-anthesis, spanning the period of mid-late development (FIG. 1B).

Figure 1C:
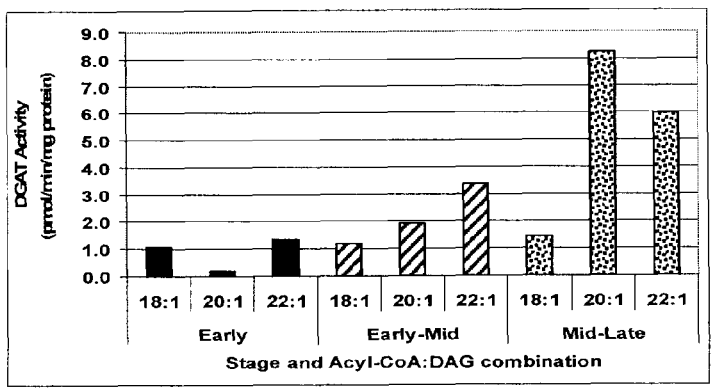

DGAT activity was assayed in microsomal fractions from early, early-mid and mid-late developing dissected embryos in the presence of pairs of fatty-acyl-CoAs and their corresponding sn-1,2 DAGs: 18:1-CoA+diolein; 20:1-CoA+dieicosenoin, 22:1-CoA+dierucin (FIG. 1 C). The highest rate of DGAT activity was observed in the microsomal fraction from mid-late developing embryos. In general, the DGAT activity throughout development in nasturtium embryos was consistently about three- to five-fold lower compared to the corresponding activities at the equivalent embryonic stages for microspore-derived embryos of *B. napus* cv Topas, used as a positive control for the DGAT1 assay. This low DGAT activity in *T. majus* is reflected in the relatively low oil content of nasturtium (typically ranging from 8-10% DW), compared to other oilseeds. Even microsomes from early stage embryos were able to synthesize trierucin. The VLC 22:1-CoA+dierucin and 20:1-CoA+dieicosenoin combinations were preferred over the oleoyl-CoA+diolein substrate pairing in both early-mid and especially mid-late developing embryos. The strong DGAT activity with erucoyl- and eicosenoyl-CoAs is reflected in the developmental DAG and TAG composition.

TAG and DAG species were analyzed using MALDI-tof MS/MS and pencil lead as the matrix. MALDI mass spectrometry has become a well established technique in the field of lipid analysis. Schiller et al. (1999) outlined the use of this technique for lipids in general, and published a comprehensive review of the field (Schiller et al., 2004). One limitation we have observed with this technique in analyzing neutral lipids is the prompt loss of acyl groups from sodiated molecular ions when using DHB as a matrix. This can make molecular weight determinations difficult, especially when analyzing plant extracts that contain numerous TAG species. The mechanism of this phenomenon was described previously Al-Saad et al. (2003).

In 2006 Langley an co-workers (Black et al., 2006) described the use of pencil lead as a matrix for analysis of low molecular weight compounds in MALDI applications. Pencil lead is a mixture of graphite, clays and waxes; hence, graphite is bound within these other materials, lessening the danger of damage to instrument electronics from loose graphite leaving the MALDI plate.

Figure 2A:
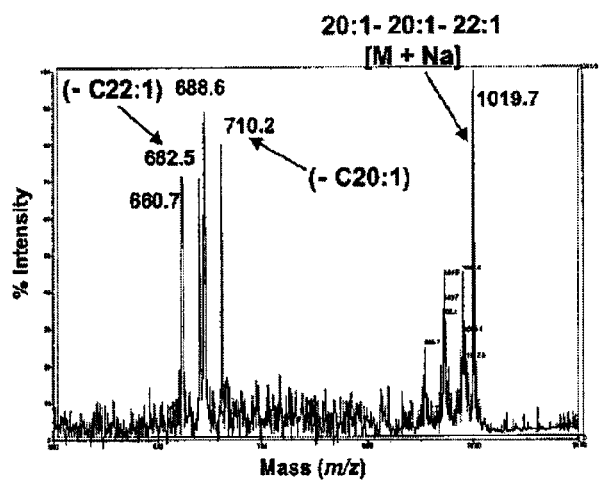
FIG. 2. Analysis of HPLC-purified *T. majus* TAG fractions in mid-developing seed by MALDI-Q tof MS/MS mass spectrometry using pencil lead as the MALDI matrix to enhance the production of cationized molecular ions in the full scan, and to evaluate Post Source Decay (PSD) of these ions for structural determination. PSD of the sodiated ions resulted in the expected losses of specific acyl (RnCOOH) or [acyl+Na] (RnCOONa) groups as delineated in Table 1. HPLC conditions were as described in "Materials and Methods"; TAGs were deemed to be (A) Fraction 15 (24-26 min): [M+Na] base peak=20:1-20:1-22:1 ((B) Fraction 16 (26-28 min): [M+Na] base peak=22:1-20:1-22:1 (C) Fraction 17 (28-30 min): [M+Na] base peak=22:1-22:1-22:1. Erucic and eicosenoic acyl moieties, are designated 22:1 and 20:1, respectively. Other TAGs and DAGs were assigned as in FIGS. 3A and 3B, and in the text, respectively.
Figure 2B:
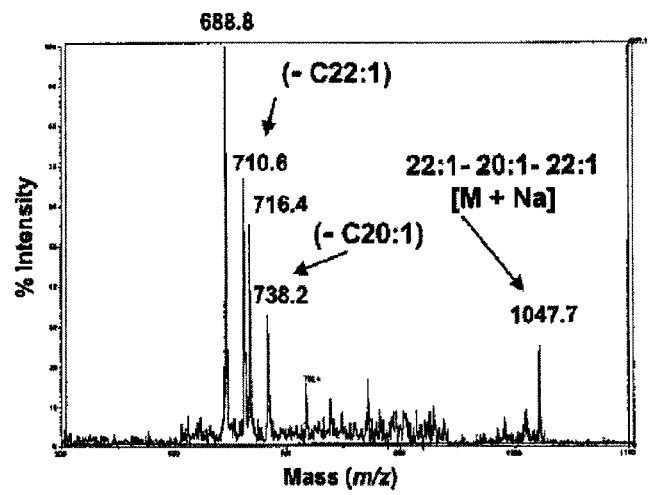
Figure 2C:
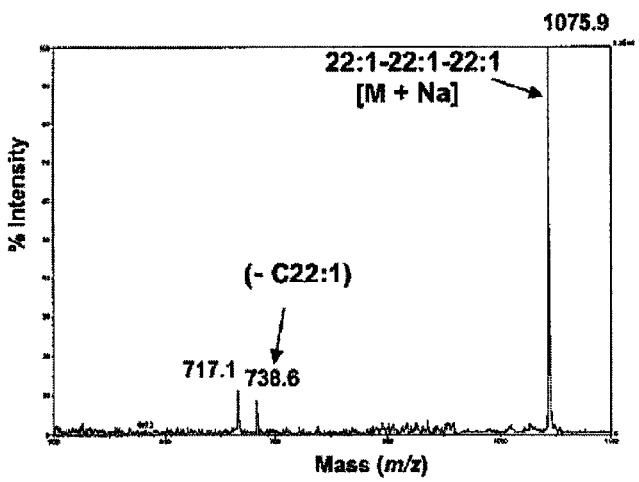

In both TAG standards and nasturtium extracts, the utilization of pencil lead as opposed to DHB as the MALDI matrix resulted in enhanced cationic molecular ion production, with a concomitant decrease in the prompt loss of the acyl groups, thereby yielding better molecular weight determinations. PSD of the standards showed the expected losses of the acyl groups from the sodiated molecular ion. Similarly, PSD of the sodiated ions of HPLC-fractionated nasturtium TAGs and DAGs also resulted in the loss of specific acyl and of [acyl+Na] groups. Typical TAG PSD spectra are shown in FIGS. 2 A-C, and expected PSD losses are shown in Table 1.

TABLE 1

Expected PSD Fragmentation Losses of Acyl Moieties from TAGs by MALDI-tof MS/MS

| Acyl Moiety chain length:# of double bonds | —RCOOH | —RCOOH + Na |
|---|---|---|
| 16:0 | −255 | −277 |
| 18:0 | −283 | −305 |
| 18:1 | −281 | −303 |
| 18:2 | −280 | −301 |

TABLE 1-continued

Expected PSD Fragmentation Losses of Acyl
Moieties from TAGs by MALDI-tof MS/MS

| Acyl Moiety chain length:# of double bonds | —RCOOH | —RCOOH + Na |
|---|---|---|
| 20:1 | −309 | −331 |
| 22:1 | −337 | −359 |

The use of this information, along with the molecular weight from the sodiated molecular ion in full scan, as well as the developmental acyl composition, allowed a determination of probable TAG and DAG structures, with the proviso that one must take into account isobaric species. No attempt was made at this time to determine the position of the acyl groups on TAGs; positional analysis had been conducted previously for mature seed oil of this nasturtium cultivar (Taylor et al., 1993 a; 1993b).

Figure 3A:
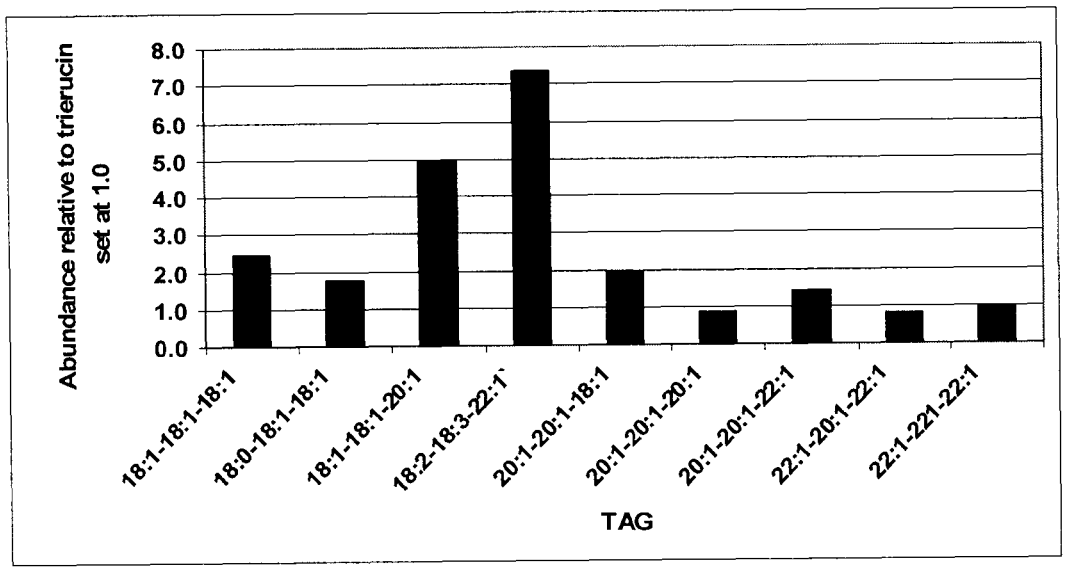
FIG. 3. TAG species accumulating in developing *T. majus* embryos at (A) Early and (B) Mid- and Late-stages. TAG species were assigned using MALDI-tof MS/MS as shown in FIG. 2 and as described in "Materials and Methods".
Figure 3B:
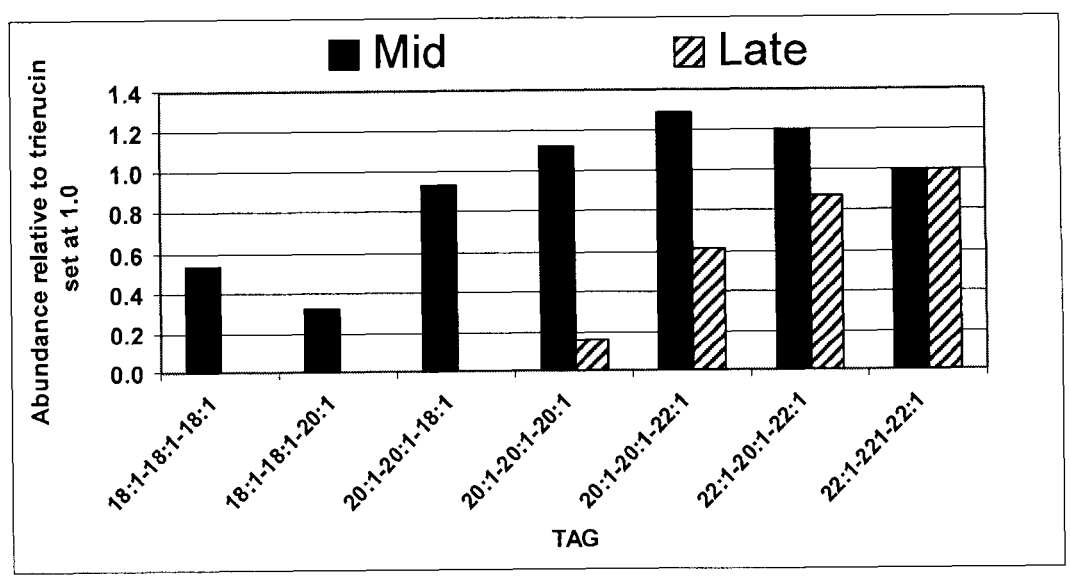

The TAG distribution at the early embryo stage reflected the prominence of oleoyl, and especially 18:2 and 18:3 acyl groups, such that 18:2-18:3-22:1, 18:1-18:1-20:1 and triolein were the main TAG species (FIG. 3A). It is noteworthy that even at this very early stage, trierucin was present, although at a low concentration. By mid-development, the trend shifted to TAGs containing at two or three VLCFAs, and by late development, the four predominant species of TAGs were: 22:1-22:1-22:1 (37%)>22:1-20:1-22:1 (32%)>20:1-20:1-22:1 (22%)>20:1-20:1-20:1 (6%) (FIG. 3B). At mid-late development, the relative distribution of the predominant DAG species was 22:1-22:1 (37%)>22:1-20:1 (19%)>20:1-20:1 (13%)>18:1-18:1 (9%)>18:1-20:1 (4%). At maturity, the predominant TAG species were trierucin followed by 22:1/20:1/22:1, supporting the trend in composition reported previously (Taylor et al., 1993; Taylor, Kunst & MacKenzie, 1993). Seeds were fully mature at about 38-40 days post anthesis.

Isolation of the DGA T1 cDNA from *Tropaeolum majus*

Based on sequence homology among plant DGAT1 genes, a full-length cDNA clone was amplified by PCR with DNA from mid-developing embryos as a template, using a degenerate primers approach and the sequence submitted to GenBank™ (Accession no. AY084052) (SEQ. ID. NO: 1). The nucleotide sequence had an open reading frame of 1,557-bp (SEQ. ID. NO: 2) encoding a polypeptide of 518 amino acids (SEQ. ID. NO: 3) with a calculated molecular mass of 58.78 kD and a predicted theoretical pI value of 8.6. The coding region is flanked by 5' and 3' untranslated regions of 171 bp and 363 bp, respectively. The *T. majus* DGAT1 clone was also represented among 20,000 ESTs isolated and analyzed from a normalized cDNA library prepared from mid-developing nasturtium embryos.

Figure 4A:
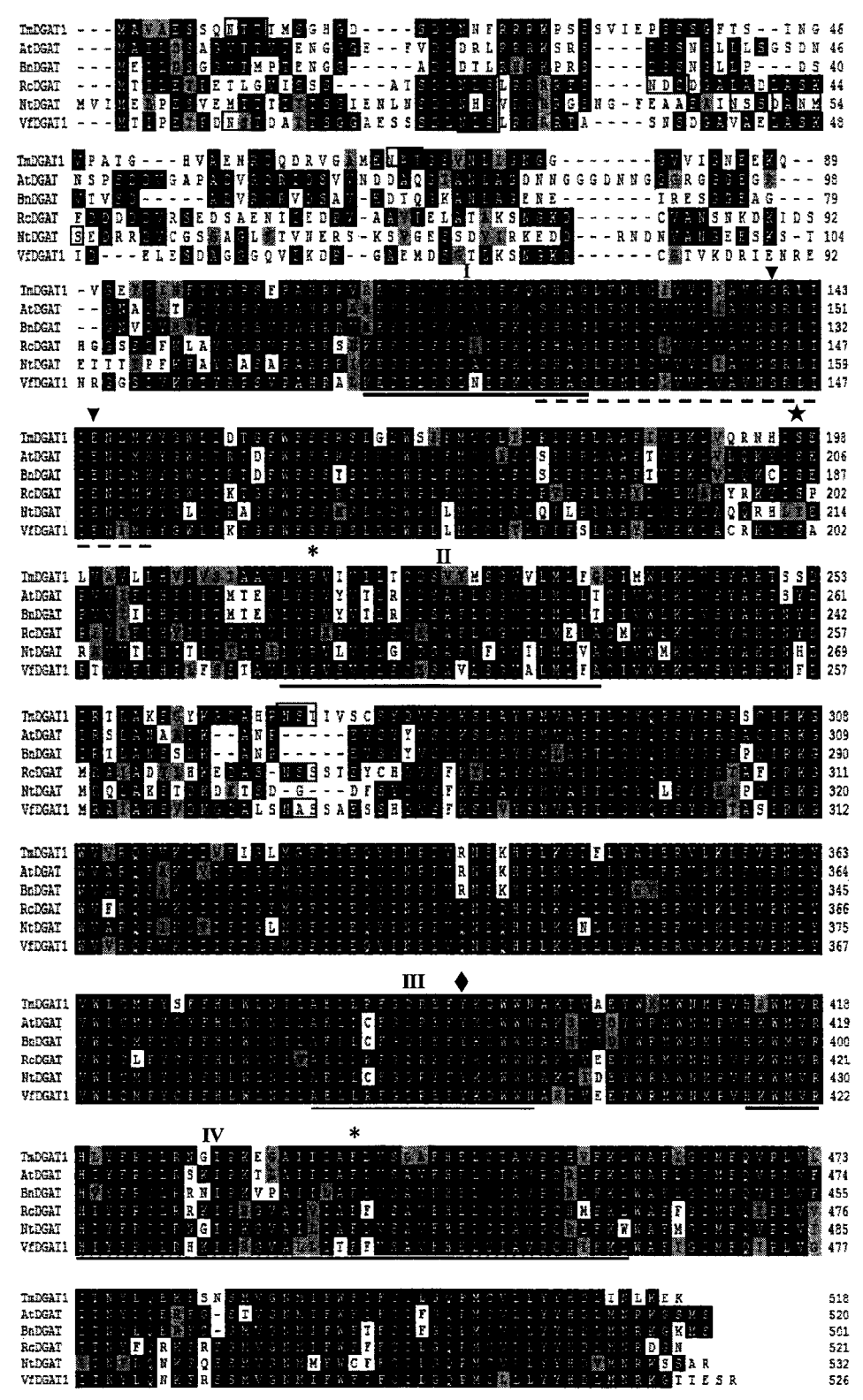
Figure 4B:
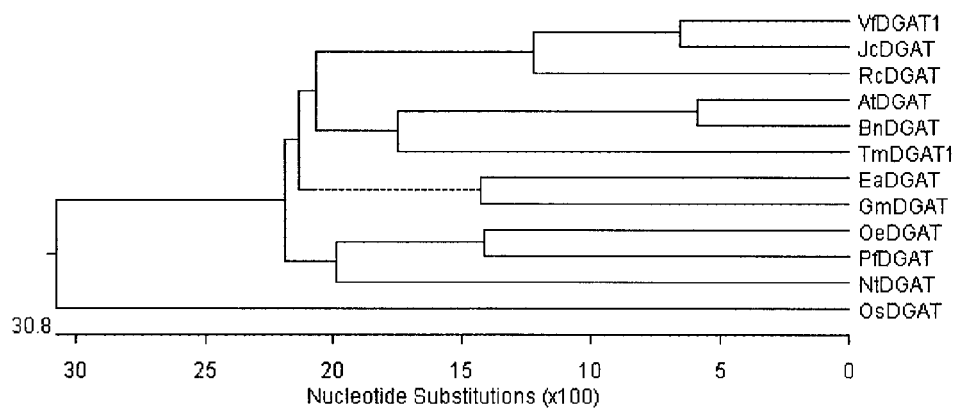
FIG. 4 (A) Homology comparison of the amino acid sequences of the *Tropaeolum majus* DGAT with DGATs from other plant species. GeneBank accession numbers: AY084052 *Tropaeolum majus* (TmDGAT), AF251794 *Brassica napus* (BnDGAT) (SEQ ID No. 38), AJ238008 *Arabidopsis thaliana* (AtDGAT) (SEQ ID No. 39), ABC94471 *Vernicia fordii* (VfDGAT) (SEQ ID No. 40), AY366496 *Ricinus communis* (RcDGAT) (SEQ ID No. 41), AF129003 *Nicotiana tabacum* (NtDGAT) (SEQ ID No. 42). Identical amino acid residues are highlighted in black. Conserved residues are shaded. A putative acyl-CoA binding motif is underlined and designated as "I". The AS11 tandem repeat is underlined by (-----) The SnRK1 target site is designated by a star. The putative thiolase acyl-enzyme intermediate signature is underlined and designated as "II"; the asterisk (*) shows the invariant proline. The putative fatty acid protein signature is underlined and designated as "III", which contains a tyrosine phosphorylation site (♦). The DAG/phorbol ester binding signature motif is underlined and designated as "IV", the asterisk shows the conserved phenylalanine. The N-glycosylation sites are boxed. The residues within the catalytic site are designated by a triangle (▼). (B) Dendrogram of the DGAT gene family based on the amino acid sequences. The alignment was carried out by the Clustal W method using Lasergene analysis software (DNAStar, Madison, Wis.).

A BLASTP search showed high identity (65-75%) of the *T. majus* DGAT1 with other plant DGAT1s. It was designated as TmDGAT1 to differentiate it from other plant homologs. As shown in FIG. 4A, very high identity was observed with DGAT1s from: *Arabidopsis thaliana* (72% GenBank#AJ238008; Zou et al, 1999), *Brassica napus* (73% GenBank#AF251794), *Ricinus communis* (65% GenBank#AY751297), *Nicotiana tabacum* (66% Genbank#AF129003) *Vernicia fordii* (67%, Genbank#DQ356680) (FIG. 4A). A recently isolated DGAT1 from soybean (*Glycine max*) (Wang et al., 2006) was 68% homologous to the TmDGAT1. Using the Clustal W method in the Lasergene analysis software suite (DNAStar, Madison, Wis.), the dendrogram (FIG. 4B) shows the relationship of the TmDGAT1 to other members of the DGAT1 gene family based on amino acid sequence alignment. DGAT1s also showed some sequence similarity to acyl CoA:cholesterol acyltransferases (ACATs) from a number of species (Chang et al., 1997) (data not shown). However, the similarity is significantly lower in comparison to that of DGAT1s at around 30%, and is largely confined to the C-terminus.

Figure 5A:
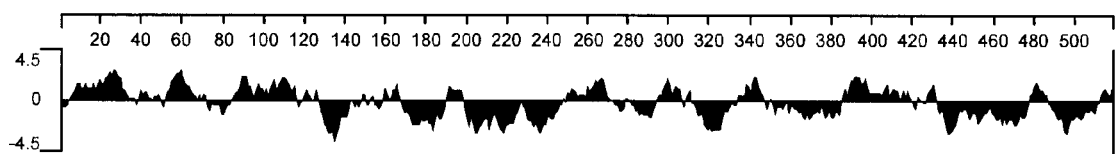
FIG. 5. Hydropathy analysis of the *T. majus* DGAT1. (A) Hydropathy plot of the TmDGAT1 indicating the presence of several hydrophobic regions. (B) Schematic representation of the putative transmembrane domains of TmDGAT1 amino-acid sequence as predicted by TMAP analysis [Persson, Argos 1994]. Numbers shown in the boxes correspond to the residues of each domain in the TmDGAT1.
Figure 5B:
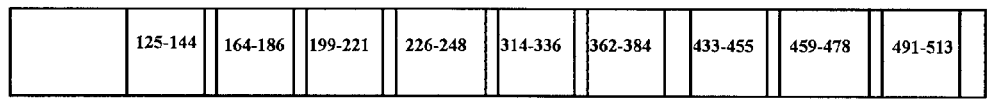

A Kyte-Doolittle hydropathy analysis of the amino acid sequence of the TmDGAT1 revealed several hydrophobic domains (FIG. 5A). Protein analysis with the TMAP algorithm (Persson and Argos, 1997) predicted 9 transmembrane domains (FIG. 5B). Upon re-analysis of the *Arabidopsis* DGAT using the TMAP algorithm, 9 transmembrane domains were also predicted (only 5 transmembrane domains reported previously when using the PC gene program (Zou et al, 1999)). This finding is consistent with the 9 transmembrane domains predicted for a mammalian DGAT (Cases et al, 1998) as well as the *Brassica napus* DGAT1, castor DGAT and soybean DGAT (Nykiforuk et al., 2002; He, et al, 2004; Wang et al., 2006). Other plant DGAT1s also contain multiple transmembrane domains (8 for tobacco DGAT and 10 for tung tree DGAT1; Shockey et al., 2006), the exception being a recently isolated peanut DGAT1, which has no predicted transmembrane domains (Saha et al., 2006).

An examination of a partial genomic clone of the TmDGAT1 revealed the presence of at least 10 introns. Southern analyses showed that there was likely only one copy of the DGAT1 gene in the *T. majus* genome, as is the case in *Arabidopsis*.

Repeated efforts to identify and clone a DGAT2 homolog by RT-PCR or by searching 20,000 ESTs, were unsuccessful, suggesting that the TmDGAT1 is perhaps the only acyl-CoA-dependent DGAT gene in developing seed of this species.

Predicted Structural Features of the TmDGAT1

The motif spanning $R^{110}$---$S^{123}$HAGLF---$K^{149}$ in the TmDGAT1 is highly conserved (90.0-97.5% identity) among other DGAT1s and contains the putative acyl-CoA binding motif $R^{110}$---$G^{126}$, as well as the putative active site catalytic residues $R^{141}$-L-I-I-$E^{145}$-$N^{146}$ (FIG. 4A). An 81 bp insertional mutation (a repeat of exon 2) in the *A. thaliana* DGAT1 gene resulted in a 27 aa repeat in this region of the DGAT1 in mutant AS11 (Zou et al, 1999), which had resulted in a reduction in seed oil content (Katavic et al., 1995). This correlation is a strong indication of the key importance of this motif for activity, and led to the cloning of the *A. thaliana* DGAT1 (Zou et al., 1999).

As reported previously (Zou et al, 1999), a putative diacylglycerol/phorbol ester-binding motif (Billheimer et al, 1990), HKW-X-X-RH-X-Y-X-P, a signature sequence observed to be unique to DGAT while absent in the ACATs (Oelkers et al., 1998), is present in the *A. thaliana* DGAT1 sequence and is located at amino acids 413-423. In the current TmDGAT1 sequence, this putative diacylglycerol/phorbol ester-binding motif is found within a highly conserved interface of a near amphiphilic/highly hydrophobic region extending from residues 413-459 (FIG. 4A).

A visual examination of the TmDGAT1 also revealed the sequence ($L^{190}$-$V^{191}$-X-$R^{193}$-X-X-X-$S^{197}$-X-X-X-$A^{201}$). Such motifs have been identified as targeting sites typical of members of the SnRK1 protein kinase family (Halford and Hardie, 1998). First identified in the *Arabidopsis thaliana* DGAT1 (Zou et al, 1999), similar motifs are now recognized in other plant DGAT1 sequences (FIG. 4A). Interestingly, as pointed out by Zou et al., (1999), similar SnRK1 targeting motifs could also be identified in the lysophosphatidic acid acyltransferases (LPAATs) from coconut (Knutzon et al, 1995) and meadowfoam (Lassner et al, 1995).

A putative acyl-CoA binding signature spans residues $R^{110}$---$G^{126}$ (interestingly, the final 4 residues of this motif are part of the tandem repeat in the *A. thaliana* AS11 mutant DGAT1). A putative catalytic site is found at residues $R^{141}$-X-X-X-$E^{145}$-$N^{146}$. There is a phosphopantetheine attachment site spanning residues $G^{157}$-$M^{172}$. A putative thiolase acyl-enzyme intermediate binding motif, previously cited in the *Arabidopsis* sequence by Zou et al (1999), is also found in the TmDGAT1. It contains an invariant $Pro^{216}$ at the N-terminus of this motif; this proline has been suggested to participate in presenting the fatty acyl group to the active site (see above) for esterification to (diacyl)glycerol. (Lewin et al, 1999). There is also a fatty acid binding protein signature spanning residues $A^{381}$-$N^{397}$ (Zou et al, 1999) which contains a putative tyrosine phosphorylation site, $Y^{392}$. The TmDGAT1 also had the following conserved signature motifs of putative function (See FIG. 4A).

A leucine zipper motif with signature residues $L^{214}$, $L^{221}$, $L^{233}$ and $L^{242}$; 2 potential DGAT motifs, $H^{249}$-X-X-X-$D^{253}$ and $H341$-X-X-X-$D^{346}$, having three or four amino acids, respectively, between what have been postulated are critical His and Asp residues (Daniel et al., 2004), a signature which is also present in other acyltransferase family members (Saha et al., 2006); 3 potential N-linked glycosylation sites (N-X-S/T), which are present in the TmDGAT, NtDGAT, and VfD-GAT1, but not in the AtDGAT and DnDGAT (He et al., 2004).

Tissue-Specific Expression of *T. majus* DGAT1

Figure 6A:
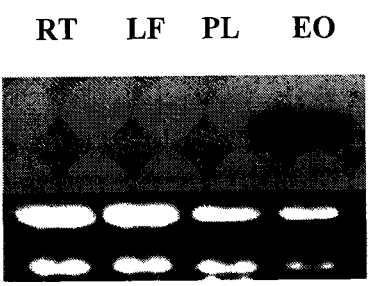
FIG. 6. Northern analysis of TmDGAT1 gene expression. (A) Total RNA was isolated from roots (RT), leaves (LF), petals (PL) and embryos (EO). (B) Total RNA was isolated from early developing embryos (EE) [8-15 dpa], mid-developing embryos (ME) [22-26 dpa], and late developing embryos (LE) [30 dpa].
Figure 6B:
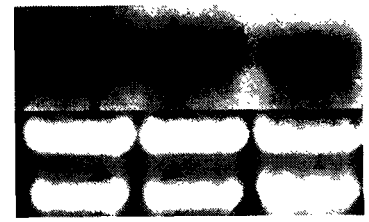

Northern blot analyses were performed to investigate the expression profile of the TmDGAT1 gene in *T. majus* roots, leaves, floral petals and developing embryos. A strong hybridization signal with a TmDGAT1-specific probe was observed only with RNA isolated from developing embryos (FIG. 6A). By further investigating three stages of seeds development in days post anthesis (dpa): (early [7-13 dpa], mid [14-19 dpa] and late [20-27 dpa]), the maximal accumulation of transcript was observed in RNA isolated from early developing embryos, and this gradually declined in the middle and late stages (FIG. 6B). Erucic acid and trierucin were already accumulating by the early stage of seed development. Based on the developmental profile for induction of DGAT activity, this finding suggests that the transcript, once produced, is very stable.

Heterologous Expression of TmDGAT1 in Sf9 Insect Cells

Figure 7:
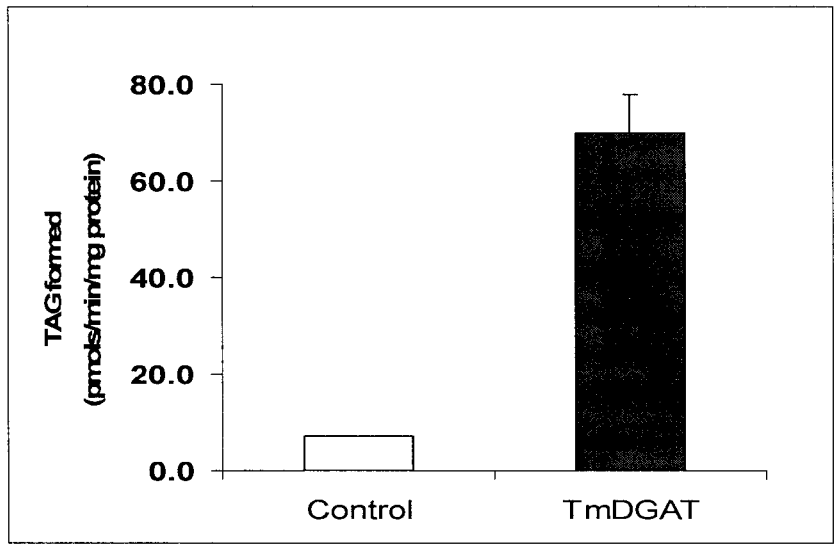
FIG. 7. Expression of *T. majus* DGAT1 in baculovirus insect cells. TmDGAT1 activity was determined using membranes isolated from insect cells infected with wild type baculovirus (Control) and TmDGAT1 recombinant baculovirus in the presence of sn-1,2-diolein and [1-$^{14}$C]oleoyl-CoA.
Figure 7:

To confirm the function of the putative DGAT clone, the full-length coding region of TmDGAT1 gene (SEQ. ID. NO: 2) was cloned into a Baculovirus insect cell expression system. The Sf9 insect cells infected with virus containing the *T. majus* DGAT1 cDNA and with control virus were collected after 48 hours post-transfection and total membrane fractions (100,000×g pellet) were assayed for DGAT activity. The membrane fraction from insect cells infected with virus containing the TmDGAT1 cDNA exhibited a strong capacity to synthesize TAGs with about 10 fold higher activity than that found in the membrane fraction from control cells infected with vector only (FIG. 7). Similar results have previously been obtained upon expression of a mouse DGAT and an *Arabidopsis* DGAT cDNA in insect cells (Cases et al., 1998; Hobbs et al., 1999).

The Substrate Preference of Recombinant TmDGAT Expressed in Yeast

Figure 8:
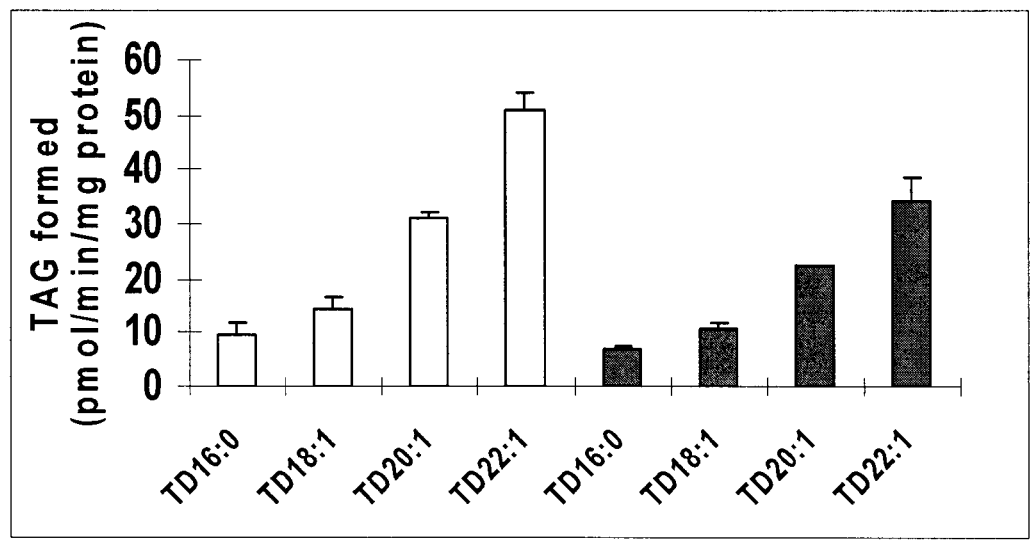
FIG. 8. Expression of TmDGAT1 in yeast mutant H1246 MATα. DGAT assays were performed on cell lysates of yeast quadruple mutant (DGAT-, PDAT-, ASAT1$^-$, ASAT2$^-$) strain: H1246 MATα transformed with pYES2.1/V5-His-TOPO plasmid only (Control) and TmDGAT1/pYES2.1 in the presence of $^{14}$C-labeled 16:0-, 18:0-, 18:1-, eicosenoyl-(20:1 Δ11) and 22:1 acyl-CoAs and sn-1,2-diolein (18:1 DAG) or sn-1,2-dierucin (22:1 DAG). The enzyme activity is scarcely detected in the yeast strain harboring the empty control vector, and has been subtracted from the enzyme activities detected from the H1246MATα strain expressing the TmDGAT1.

The TmDGAT1 coding region (SEQ. ID. NO: 2) was also cloned into a yeast expression vector pYES2.1 under the control of the galactose-inducible GAL1 promoter, and the construct was used to transform a yeast mutant strain H1246MATα, which lacks all four genes, ARE1, ARE2, DGAT1 and LRO1, which were found to contribute to TAG synthesis in yeast (Sandager et al., 2002). H1246MATα yeast cells harboring an empty pYES2.1 vector plasmid were used as a control. Under our experimental conditions, an in vitro assay of membrane fractions isolated from the two transformants showed that the expression of the TmDGAT1 in the H1246MATα strain resulted in a restoration of DGAT function in the mutant host (enzyme activity is hardly detected in the yeast strain harboring the empty control vector; data not shown) making it an ideal system for examining acyl preference. The microsomal membrane fractions from the induced yeast cells were assayed for DGAT activity using either 1-$^{14}$C-labelled palmitoyl (16:0)-, oleoyl (18:1)-, eicosenoyl (20:1(11))- or erucoyl (22:1)-CoA as an acyl doner, and unlabelled sn-1,2-diolein (18:1) or sn-1,2-dierucin (22:1) as acceptor. As shown in FIG. 8, the TmDGAT1 protein showed an preference for utilizing acyl-CoAs of increasing chain length to produce TAGs, a trend observed regardless of whether sn-1,2-diolein(18:1) or sn-1,2-dierucin (22:1) was the as acyl acceptor. DGAT activity was about 2-fold higher when using 20:1-CoA and 3-fold higher when using 22:1-CoA compared to TAGs formed using 18:1-CoA. In both cases, the lowest level of TAG was detected when using the saturated 16:0-acyl-CoA. Comparing the two acyl acceptors used here, it seemed that in vitro, the TmDGAT1 preferred diolein over dierucin when using the same acyl-CoA donor (FIG. 8). There was no activity when radiolabeled free fatty acids were tested as acyl donors (data not shown), confirming that the cDNA encodes an acyl-CoA-dependent DGAT1.

Figure 9A:
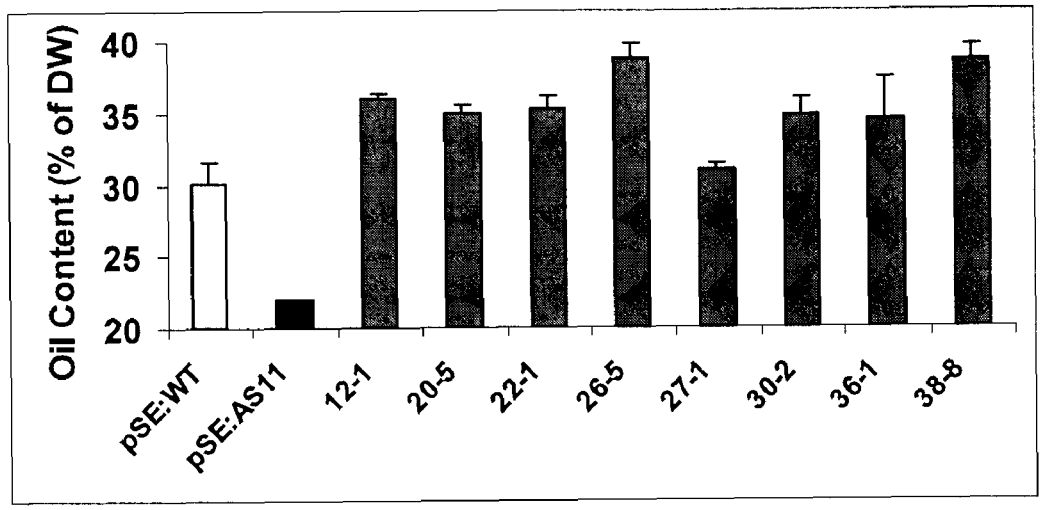
FIG. 9. Complementation of *A. thaliana* AS11 mutant seed oil and fatty acid profile by expression of TmDGAT1. Transformation of *Arabidopsis* mutant line AS11 with the TmDGAT1 cDNA under the control of a napin promoter leads to a restoration of (A) fatty acid composition profile of the transgenic lines and (B) the WT level oil content. Total oil content (as percentage of mature seed dry weight) and fatty acid composition (% wt/wt) were determined on the seed oil extracted from $T_3$ seeds of *Arabidopsis* pSE:WT and pSE:AS11 (empty plasmid) controls and from napin:TmDGAT1 AS11 transgenics lines.
Figure 9B:
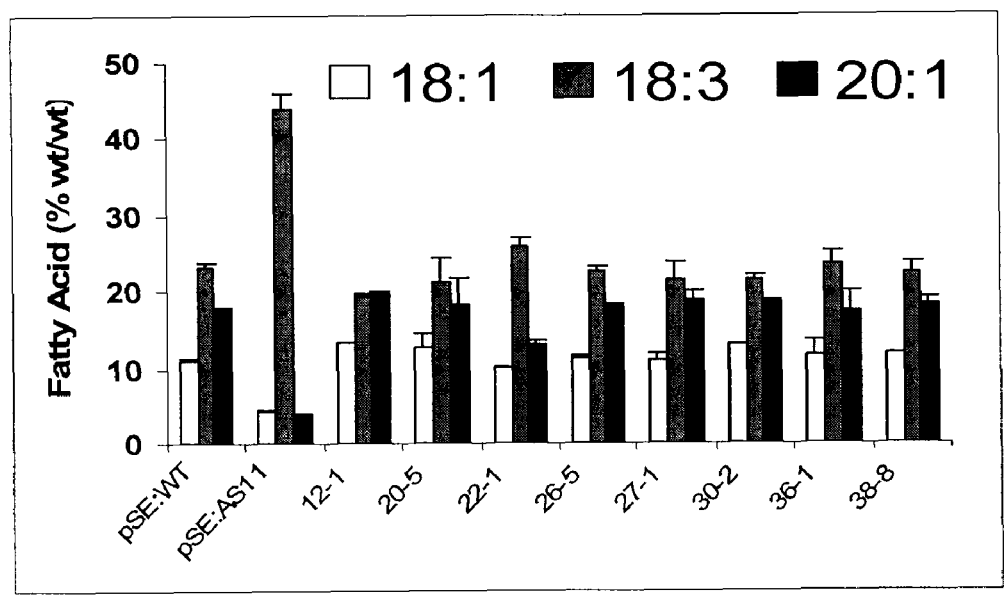

Expression of TmDGAT1 in *Arabidopsis*: Complementation of *Arabidopsis* AS11 DGAT Mutant The coding region of the TmDGAT1 (SEQ. ID. NO: 2) was cloned into a pSE vector behind the seed-specific napin promoter. The napin/DGAT1 plasmid was introduced into *Agrobacterium tumefaciens* and used to transform *Arabidopsis* DGAT1 mutant AS11. AS11 has a low TAG phenotype, an ultra-low 18:1/ultra-high 18:3/ultra-low 20:1 fatty acid phenotype, and dramatic changes in the sn-3 fatty acyl composition of its seed oil, true indicators of a mutation in the *Arabidopsis* AS11 DGAT seed protein (Katavic et al, 1995; Zou et al, 1999). Based on kanamycin selection, a number of primary napin:TmDGAT1 AS11 transgenic lines were produced, the $T_1$ plantlets grown to maturity, and $T_2$ seeds harvested, then segregation analyses were performed on the $T_3$ generation. At the same time several independent plasmid only control AS11 transgenic (pSE vector without DGAT1 insert) lines, as well as napin:TmDGAT1 in WT and pSE in WT transgenic lines were propagated and analyzed. The GC analysis of homozygous $T_3$ transgenic seed lines showed that seed specific expression of TmDGAT1 in AS11 was able to complement the fatty acid compositional mutant phenotype, restoring the proportions of 18:1, 20:1 and 18:3 to give a WT profile (FIG. 9A). In particular, the proportion of the sn-3 "marker" VLCFA, 20:1, was restored, which again, is a strong indication of the function of the TmDGAT1. In addition, the TmDGAT1 was able to complement the reduced TAG phenotype of the AS11 mutant, such that TAG levels were at least as high as that found in wild type *Arabidopsis* (FIG. 9B).

Expression of TmDGAT1 in *Arabidopsis*: Over-Expression in Wild-Type *Arabidopsis*

To determine whether TmDGAT1 over-expression has any biological significance in a non-mutant, the *Agrobacterium tumefaciens* harboring the napin/TmDGAT1 plasmid was also used to transform wild type (WT) *Arabidopsis*. Kanamycin-resistant $T_1$ plants were selected and propagated. The $T_2$ progeny were collected individually and the total oil content and fatty acid composition was determined. After analysis, a number of independent $T_2$ transgenic lines containing the napin:DGAT1 construct were selected for detailed study based on increased oil deposition on a per seed basis and an increased average 1,000-seed weight (data not shown). From the $T_2$ progeny, segregation analyses were performed on the $T_3$ generation, and homozygous lines were identified and subjected to further analysis.

Figure 10A:
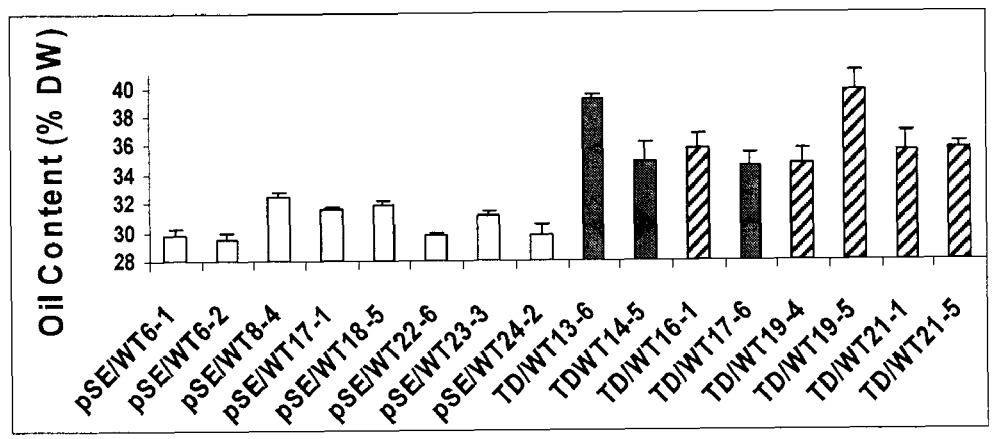
FIG. 10. Over expression of the TmDGAT1 in *Arabidopsis*. Effect of transformation of *Arabidopsis* with the TmDGAT1 cDNA under the control of a napin promoter on (A) oil content and (B) average 1000-seed weight. Total oil content (as percentage of mature seed dry weight) and seed weight are shown for pSE (empty plasmid) in WT *Arabidopsis* (white bars), non-transformed WT *Arabidopsis* (black bars) and napin:TmDGAT1 transgenic homozygous $T_3$ *Arabidopsis* lines (gray bars represent transgenic lines with a single insert and hatched bars represents transgenic lines with multiple inserts). (C) Fatty acid composition is shown for pSE (empty plasmid) in WT *Arabidopsis* and napin:TmDGAT1 transgenic homozygous $T_3$ *Arabidopsis* lines. Homozygous $T_3$ napin:TmDGAT1 lines were analyzed in triplicate, about 200 seeds per sample, accurately counted and weighed. For the plasmid only pSE in WT transgenic and non-transformed WT controls, ≧8 individual seed lots were similarly analyzed; the averaged values are presented.
Figure 10B:
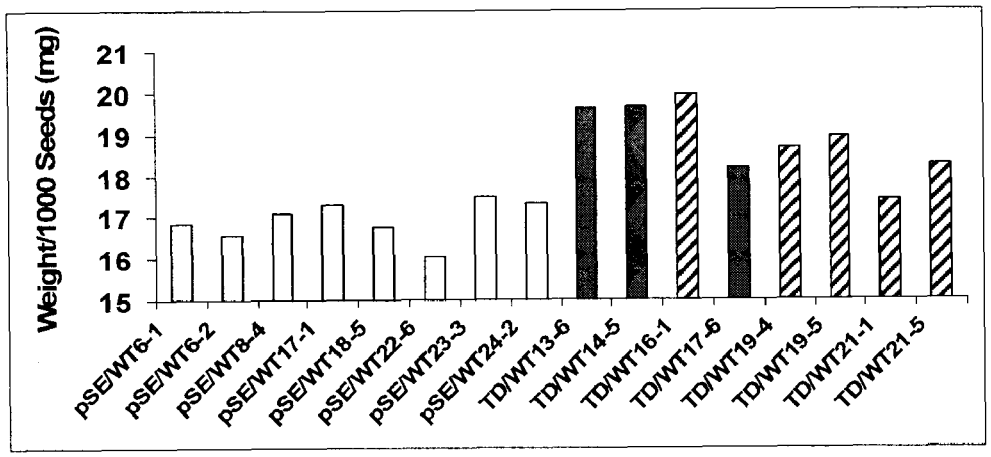
Figure 10C:
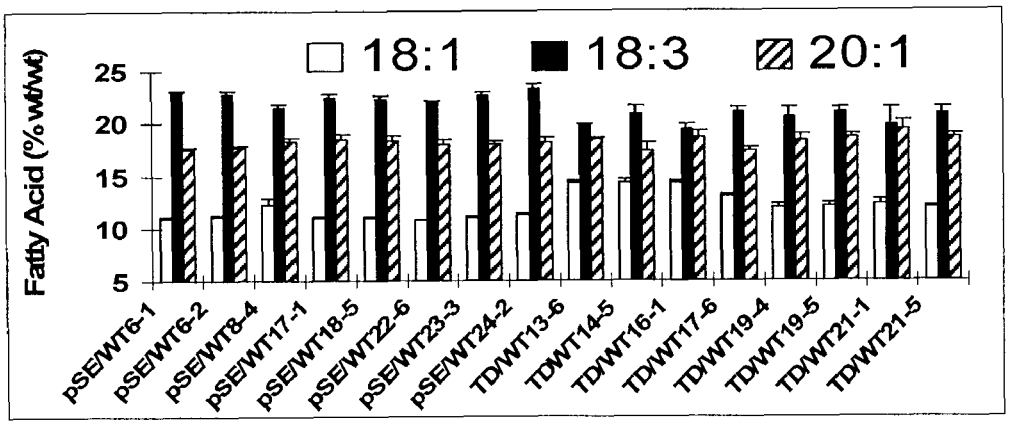

The data for the napin:TmDGAT1 transgenic lines were compared with those acquired from independent $T_3$ pSE (empty plasmid) in WT control plants. As shown in FIG. 10A, on a mature seed weight basis, the homozygous napin:TmDGAT1 lines exhibited oil content increases ranging from 2.6 to 8.6 percentage points, representing net overall oil increases of 10% to 28%, compared with the range exhibited by pSE WT controls. In addition, the average 1,000-seed-weight in the napin:TmDGAT1 homozygous transgenic lines was generally increased, by as much as 20 to 30% for lines 13-6, 14-5 and 16-1 (FIG. 10B). The fatty acid composition of the napin:TmDGAT1 *Arabidopsis* transgenic lines was minimally affected by over expression of TmDGAT1 gene, with increases from 0.7% to 2.3% for 18:1, decreases of 1.3% to 3.0% for 18:3 and a slight increase (0.3%) for 20:1, compared with pSE controls (FIG. 10C).

Figure 11A:
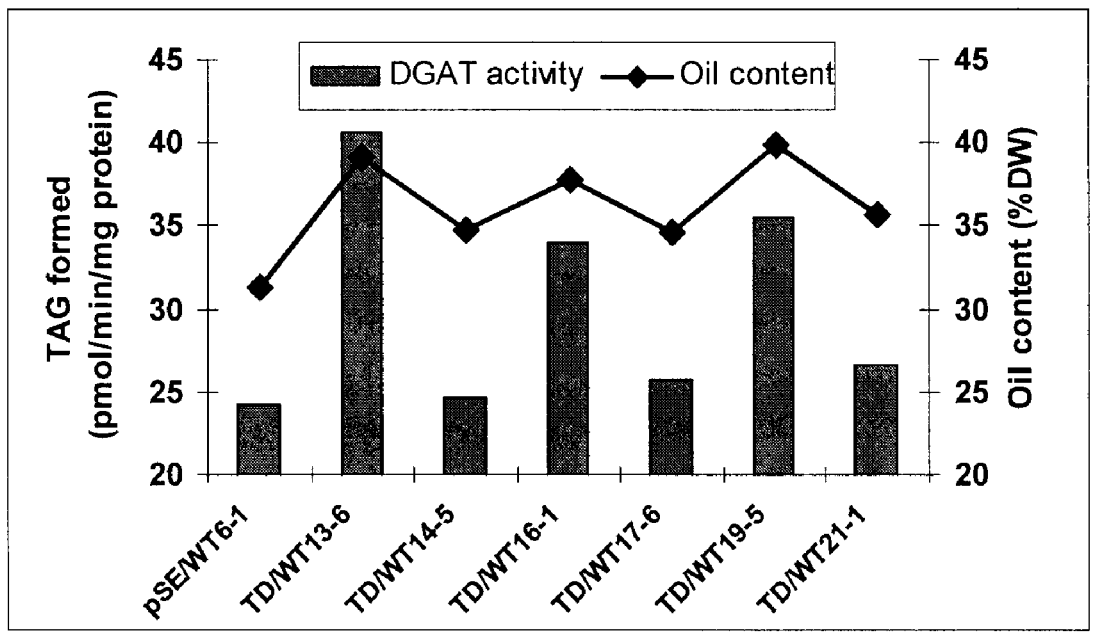
FIG. 11. (A) DGAT activity in microsomal fractions prepared from pooled mid-developing seed samples from $T_3$ transgenic lines of napin:TmDGAT1 (FD/WT #-#) and pSE plasmid-only control (pSE/WT #-#) transformed *Arabidopsis* are compared to the oil content of mature seed from $T_3$ transgenic lines. (Values of oil content of $T_3$ transgenic lines are also reported in FIG. 10A). (B) Northern analysis of TmDGAT1 gene expression in pooled mid-developing seed samples from $T_3$ transgenic lines of napin:TmDGAT1 and pSE control transformed *Arabidopsis*. Lane 1=pSE/WT 6-1; Lane 2=TD/WT 13-6; Lane 3=TD/WT 14-5; Lane 4=TD/WT 16-1; Lane 5=TD/WT 17-6; Lane 6=TD/WT 19-5; Lane 7=TD/WT 21-1. 20 µg total RNA extracted from siliques containing mid-green developing seeds was loaded for each sample.
Figure 11B:
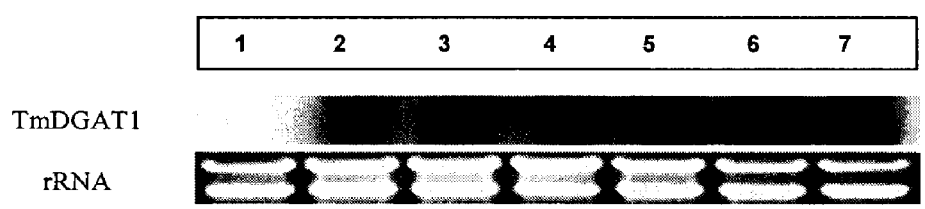

Using mid-developing seed samples from $T_3$ transgenic lines of napin:TmDGAT1 and pSE control *Arabidopsis*, the level of expression of the TmDGAT1 gene, and its effect on DGAT enzyme activity were investigated. An accumulation of the TmDGAT1 gene transcripts were detected on all the napin:TmDGAT1 transformed *Arabidopsis* mid-developing seed samples by northern analysis; no signals were present in the empty pSE control transformants (FIG. 11A). Compared to the empty pSE vector controls, all the napin:TmDGAT1 transformed lines exhibited increased DGAT activity, and there was a good correlation between this increase and enhancement of the oil content of mature seeds from these $T_3$ transgenic lines (FIG. 11B). There seemed to be no direct linear correlation between the transcript level and the degree of DGAT activity and oil content enhancement.

Expression of TmDGAT1 in *B. napus*: Over-Expression in a HEAR Breeding Line

Figure 12A:
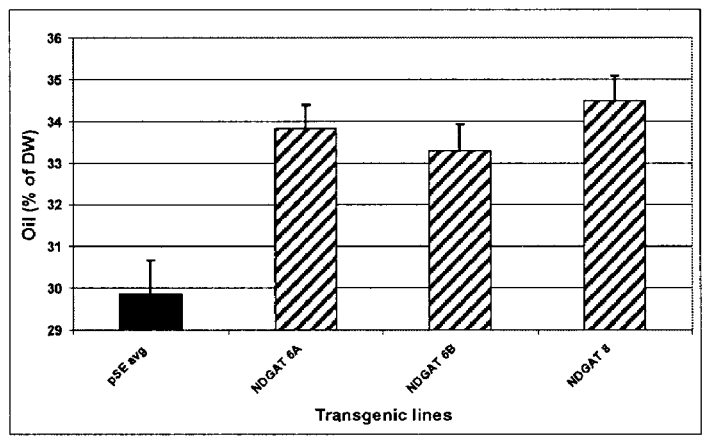
FIG. 12. Over expression of the TmDGAT1 in *B. napus* High erucic acid rapeseed breeding line 2026 (courtesy of Dr. P. B. E. McVetty, University of Manitoba). Effect of transformation of *B. napus* with the TmDGAT1 cDNA under control of the napin promoter on (A) oil content (as percentage of mature seed dry weight), (B) Total oil/100 seeds, (C) Relative net oil content (with the control average set at 100%). $T_1$ seeds of *B. napus* plasmid-only control transgenic lines (napin:pSE; black bar) and napin:TmDGAT1 transgenic lines (hatched bars) are shown ±SE.
Figure 12B:
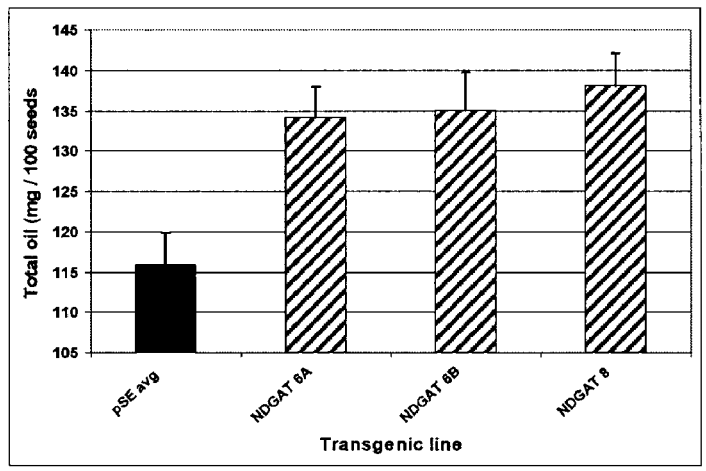
Figure 12C:
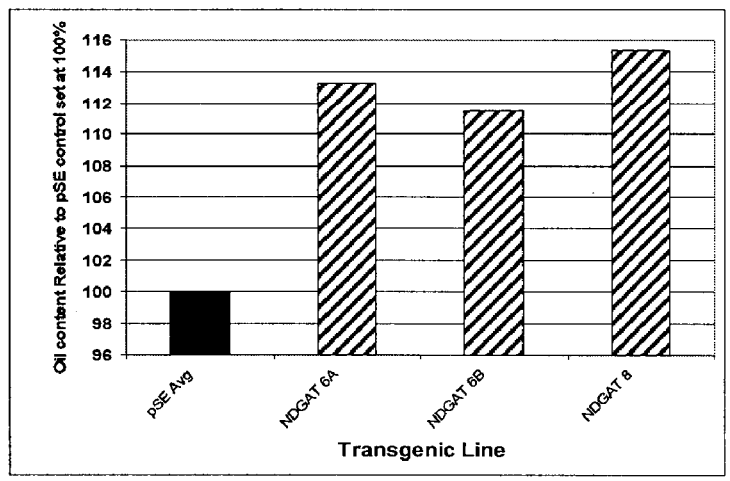

To determine the effect of TmDGAT1 over-expression in *B. napus*, the *Agrobacterium tumefaciens* harboring the napin/TmDGAT1 plasmid was also used to transform high erucic acid (HEAR) breeding line 2026 (Courtesy of Dr P. B. E. McVetty, University of Manitoba). Kanamycin-resistant $T_1$ plants were selected and subjected to lipid analyses. As shown in FIG. 12A, on a mature seed weight basis, the napin:TmDGAT1 lines exhibited oil content increases ranging from 3.5-4.5 percentage points, representing net overall oil increases of 11% to 15% (FIG. 12C), compared with the average exhibited by pSE WT controls. The oil content on a per 100-seed basis was also increased in the napin:TmDGAT1 transgenics by 20-30 mg (FIG. 12B). In addition, the average 100-seed-weight in one napin:TmDGAT1 transgenic lines 15C, was increased, by 16%. DGAT1 activity was from 30-60% higher in developing seed of the napin:TmDGAT1 transgenic lines than that observed in the pSE WT control.

Site Directed Mutagenesis (SDM) of Functional Regions of TmDGAT1

To better understand the functional regions essential for TmDGAT1 activity and reveal how the enzyme activity may be regulated by post-translational modification (e.g. phosphorylation), we performed site-directed mutagenesis (SDM) within signature regions putatively involved in enzyme function or regulation. Table 2 provides a list of the SDM primers used in this study with the desired mutations in bold, underlined.

TABLE 2

Mutagenic Oligonucleotide Primers

| Mutation | Oligonucleotide Primer Sequence |
| --- | --- |
| Phe$^{439}$ to Arg | F2RF: 5'-GGTGCCATTATTATCGCGCGCTTAG TTTCTGGTGC-3' (SEQ ID NO: 26) F2RR: 5'-GCACCAGAAACTAAGCGCGCGATAA TAATGGCACC-3' (SEQ ID NO: 27) |
| Pro$^{216}$ to Arg | P2RF: 5'-CCGCTGGAGTTTTATATCGAGTTAT TGTGATCTTAACG-3' (SEQ ID NO: 28) P2RR: 5'-CGTTAAGATCACAATAACTCGATAT AAAACTGCAGCGG-3' (SEQ ID NO: 29) |
| Tyr$^{392}$ to Ala | TF3: 5'-TGGTGATCGTGAATTCGCCAAAGATT GGTGG-3' (SEQ ID NO: 30) TF4: 5'-CCACCAATCTTTGGCGAATTCACGAT CACCA-3' (SEQ ID NO: 31) |
| Tyr$^{392}$ to Gly & Trp$^{395}$ to Gly | TF5: 5'-TGGTGATCGTGAATTCGGCAAAGATG GGTGGAATGC-3' (SEQ ID NO: 32) TF6: 5'-GCATTCCACCCATCTTTGCCGAATTC ACGATCACCA-3' (SEQ ID NO: 33) |
| Glu$^{145}$ to Val | TF14: 5'-AGTAGGCTTATCATCGTAAATCTTA TGAAGTATGG-3' (SEQ ID NO: 34) TF15: 5'-CCATACTTCATAAGATTTACGATGA TAAGCCTACT-3' (SEQ ID NO: 35) |
| Ser$^{197}$ to Ala | S2AF: 5'-GCGAAATCATATAGCTGAACTTGTT GCTGTTCTCC-3' (SEQ ID NO: 36) S2AR: 5'-GGAGAACAGCAACAAGTTCAGCTAT ATGATTTCGC-3' (SEQ ID NO: 37) |

One mutation was made in a putative diacylglycerol (DAG)/phorbol ester binding motif; the Phenylalanine$^{439}$ at the most hydrophobic point was changed to an Arginine residue (SEQ ID NO: 4, refer to SEQ ID NO: 10 for the nucleotide sequence). Another mutation was introduced into the putative thiolase acyl-enzyme intermediate signature; the invariant Proline$^{216}$ residue thought to be involved in acyl-CoA binding (Lewin et al., 1999) was substituted with an Arginine residue (SEQ ID NO: 5, refer to SEQ ID NO: 11 for the nucleotide sequence). A third mutation was conducted at Ser$^{197}$ (changed to an Alanine) (SEQ ID NO: 6, refer to SEQ ID NO: 12 for the nucleotide sequence) in the putative serine/tyrosine protein kinase SNF1-Related protein Kinase (SnRK1) phosphorylation motif. A fourth mutation was created in the catalytic site where an acidic Glutamate$^{145}$ was replaced with a Valine residue (SEQ ID NO: 7, refer to SEQ ID NO: 13 for the nucleotide sequence). The final two mutations were introduced into a putative tyrosine protein kinase (phosphorylation) motif located within a fatty acid binding protein signature, with the Tyrosine$^{392}$ residue being changed to an Alanine residue (SEQ ID NO: 8, refer to SEQ ID NO: 14 for the nucleotide sequence). A double mutation was also introduced at this tyrosine protein kinase motif, with both the Tyrosine$^{392}$ and the Tryptophan$^{395}$ residues being changed to *Glycine* residues (SEQ ID NO: 9, refer to SEQ ID NO: 15 for the nucleotide sequence).

Figure 13A:
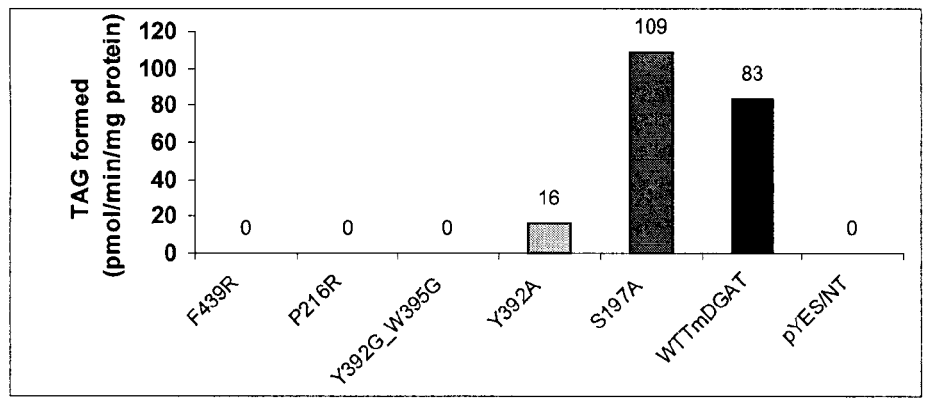
FIG. 13. Expression of site-directed mutagenized (SDM) TmDGAT1 cDNAs in yeast quadruple mutant H1246 MATα. (A) The nasturtium DGAT1 cDNAs in pYES2/NT plasmid were transformed into a yeast DGAT mutant strain: H1246 MATα. The specific SDM changes were: F2R=Phe$^{439}$ to Arg (SEQ. ID. NO: 4, refer to SEQ. ID. NO: 10 for the nucleotide sequence); P2R=Pro$^{216}$ to Arg (SEQ. ID. NO: 5, refer to SEQ. ID. NO: 11 for the nucleotide sequence); Y2G_W2G=Tyr$^{392}$ to Gly+Trp$^{395}$ to Gly (SEQ. ID. NO: 9, refer to SEQ. ID. NO: 15 for the nucleotide sequence); Y2A=Tyr$^{392}$ to Ala (SEQ. ID. NO: 8, refer to SEQ. ID. NO: 14 for the nucleotide sequence); S2A=Ser$^{197}$ to Ala (SEQ. ID. NO: 6, refer to SEQ. ID. NO: 12 for the nucleotide sequence) and E2V=E$^{145}$ to Val (SEQ. ID. NO: 7, refer to SEQ. ID. NO: 13 for the nucleotide sequence). Yeast cells transformed with pYES2/NT plasmid only was used as a control. The mutant, transformed with the native TmDGAT1, was used as a positive DGAT control. Following the induction in the presence of galactose, the transformants were lysed and assayed for DGAT activity. (B) Western blot of the SDM TmDGATs using an Anti-Xpress antibody. Following a 7 h lyse, a 15,000×g protein pellet isolated and proteins separated by SDS-PAGE. Lane 1=F439R; Lane 2=P216R; Lane 3=Y392G_W395G; Lane 4=Y392A; Lane 5=S197A; Lane 6=WTTmDGAT; Lane 7=pYES/NT.
Figure 13B:
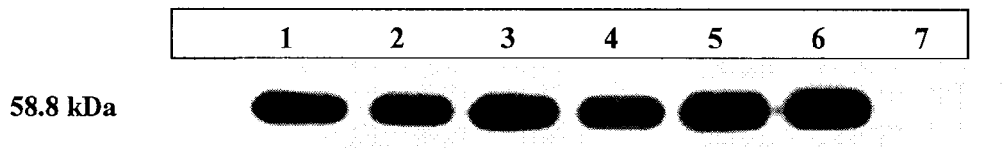
Figure 14:
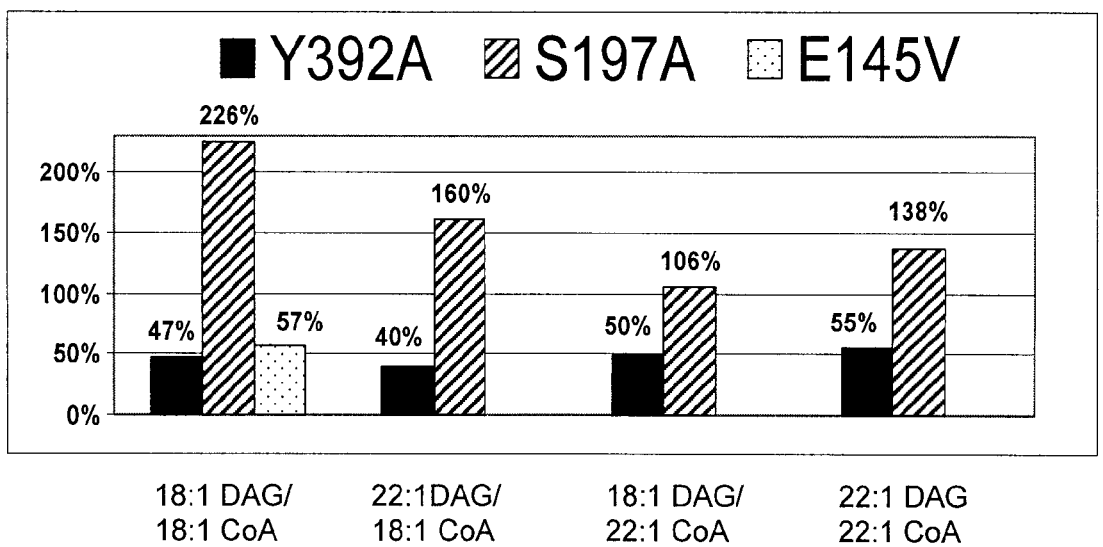
FIG. 14. SDM TmDGATs (SnRK1 and Tyr-P sites) activity utilizing $^{14}$C labeled erucoyl-CoA or oleoyl-CoA+sn-1,2-diolein or dierucin. SDM TmDGATs were transformed into yeast DGAT mutant, H1246 MATα, following induction by galactose the yeast were assayed for DGAT activity. Activity is expressed as a percent of native TmDGAT, with native TmDGAT activity set at 100%.

Sequences designed to produce proteins with the required SDM amino acid change(s) were cloned into a yeast expression vector pYES2/NT and transformed into a quadruple yeast mutant H1246MAT. The yeast transformants were induced using galactose, the recombinant protein fractions harvested and then verified via western blot and assayed for TmDGAT1 activity (FIG. 12A). Yeast cells transformed with pYES2/NT plasmid only construct (Control) was used as a control. The yeast transformed with the native DGAT construct (WT) was used as a positive control and its activity set at 100. The results shown in Table 3 are from 3 independent experiments. Western blot experiments were conducted using an anti-Xpress antibody against an Xpress epitope encoded by the N-terminal peptide on the pYES2/NT vector. All of the recombinant SDM TmDGAT1s were positive via a western, confirming the presence of DGAT protein after 7 hr of induction (FIG. 12B). With respect to enzyme activity, it is clear that substitution of Phenylalanine$^{439}$ with Arginine in the DAG/phorbol ester binding signature motif, and substitution of Proline$^{216}$ with Arginine in the thiolase acyl-enzyme intermediate signature motif both resulted in the total loss of DGAT1 activity, when compared to the recombinant WT TmDGAT1. Substitution of Tyrosine$^{392}$ with Alanine in the tyrosine protein kinase (phosphorylation) motif resulted in a dramatic decrease (80%) in DGAT1 activity compared to wild type, while the substitution of both Tyrosine$^{392}$ and Tryptophan$^{395}$, each with Glycine, in this motif resulted in a total loss of activity. Interestingly, replacement of the negatively charged E$^{145}$ residue in the catalytic site with the neutral valine severely reduced (43%), but did not eliminate, DGAT activity. Of major significance, substitution of Serine$^{197}$ with Alanine resulted in a strong increase ranging from 28 to 126%, in DGAT1 activity (FIG. 12A and Table 3). This suggests that this point mutation imparts an up-regulation in DGAT activity; it is also strong evidence that the putative SnRK1 is a serine/threonine protein kinase target site. Furthermore, the down-regulation of the Y$^{392}$ mutant enzyme activity, and the up-regulation of the S$^{197}$ enzyme activity showed consistent trends regardless of the acyl-CoA: sn-1,2-DAG pairing (FIG. 13). Of note, with the erucoyl-CoA:sn-1,2-dierucin pairing of substrates, the S$^{197}$A mutation enabled an ca 40% increase in trierucin production when compared to the native DGAT1.

TABLE 3

Site-directed Mutagenesis (SDM) Studies of the TmDGAT

| Control | F439R | P216R | Y392G + W395G | Y392A | E145V | S197A | WT |
|---|---|---|---|---|---|---|---|
| 0 | 0 | 0 | 0 | — | 57% | 148% | 100% |
| 0 | 0 | 0 | 0 | 20% | — | 142% | 100% |
| 0 | 0 | 0 | 0 | 47% | — | 226% | 100% |

We have cloned and characterized a DGAT1 gene (TmDGAT1) from *Tropaeolum majus* (garden nasturtium), which encodes a protein with high homology and significant primary structural similarity to other previously identified DGAT1 genes in different plant species. Protein analysis with the TMAP algorithm (Persson and Argos, 1997) predicted that the TmDGAT1 possesses 9 transmembrane domains, a structural feature which correlates with other plant DGAT1s (Zou et al., 1999; Hobbs et al., 1999; Nykiforuk et al., 2002; He, et al, 2004; Shockey et al., 2006), and consistent with its role as an integral membrane protein that has been shown to be localized in the endoplasmic reticulum (Shockey et al, 2006).

Northern analyses of RNA isolated from different tissues revealed that TmDGAT1 is detected only in developing embryos, but not in leaves, roots or flower petals. Among the three different seed developmental stages investigated, the maximal accumulation of transcript was observed in early developing embryos, as early as 7-13 dpa (representing about 20-40% of time to maturity) gradually declining in the middle and late stages. Similarly, the expression of a castor DGAT1 peaked at an early stage of seed development (19 dpa—approx 40% of time to maturity), and declined thereafter (He et al., 2004). A microarray study of tissue-specific *Arabidopsis* ESTs determined that the *Arabidopsis* DGAT gene is 2-fold more highly expressed in the early stages of seed development (Yamada et al., 2003). During *Arabidopsis* embryo development, DGAT1 protein is present as early as 5 dpa, then peaks at 7-9 dpa and then gradually declines, though it is still detectable at 23 dpa when the seeds are turning brown and desiccating (Lu et al., 2003). The beginning of the rise in DGAT activity lagged about one stage behind the transcript level, consistent with the general finding that DGAT1 protein accumulation seems to temporally follow the trend in transcript expression during seed development. While it does not appear to be the case for nasturtium, other DGAT1 homologs are ubiquitously expressed, including in germinating seedlings (Zou et al., 1999; Zimmermann et al., 2004; Shockey et al., 2006). In contrast, the AhDGAT2 transcript in peanut is detected only in developing seeds, concomitant with oil deposition (Saha et al., 2006). This suggests a complex level of temporal or developmental regulation over and above tissue-specific expression (Saha et al., 2006).

Results from two heterologous expression studies (in insect cells and in yeast) independently confirmed that the TmDGAT1 gene encodes a protein that functions as an acyl-CoA-dependent DGAT. The recombinant TmDGAT1 protein, when expressed in a quadruple yeast mutant strain devoid of all enzymes which can contribute to TAG synthesis, showed that there was a preference for utilizing acyl-CoAs of increasing chain length when sn-1,2-diolein or sn-1,2-dierucin was the acyl acceptor. Most significantly, a preference for utilizing $^{14}$C-erucoyl-CoA in the presence of sn-1,2-dierucin to form $^{14}$C trierucin was exhibited. Biochemical studies have consistently shown that while DGATs are somewhat indiscriminate, and capable of utilizing a wide range of acyl-CoAs in vitro, they may selectively incorporate unusual fatty acyl-CoAs (e.g. ricinoleoyl-CoA, short chain, lauroyl-CoA, erucoyl-CoA into TAGs in vivo in oilseeds containing high proportions of such fatty acids (e.g. castor, *Cuphea*, oil palm and *B. napus*, respectively) (Cao and Huang, 1986; 1987; Stymne and Stobart, 1987; Taylor et al., 1991; see review by Weselake, 2005). Recently, DGATs showing a preference for utilizing vernoloyl-CoA or acetyl-CoA have been characterized from *Vernonia/Stokesia* spp. or *Euonymus alatus* which have seed oils high in epoxy (Yu et al. 2006) or sn-3 acetyl (Milcamps et al., 2005) fatty acids, respectively. The current finding with the recombinant TmDGAT1 from nasturtium seed which contains very high proportions of erucic acid is therefore entirely consistent with this. In the current study, the in vitro finding of a slight preference of the TmDGAT1 for diolein over dierucin is probably not physiologically significant given the acyl composition of the DAG pool in mid-late developing seeds is largely dierucin; diolein constitutes less than 10% of the DAG pool, as cited above.

In parallel plant transformation studies, seed-specific overexpression of the TmDGAT1 in wild type *Arabidopsis* resulted in an increase in oil content and average 1000-seed-weight. There was no penalty in 1000-seed-weight due to oil content increases, the result being an increase in total oil on a per-seed basis of between 20 and 48% in the TmDGAT1 transgenic lines. The increment in mature seed oil content was correlated with increased DGAT activity in vitro as measured in mid-developing seed of each transgenic line. In the best line (TD/WT 13-6), a two-fold increase in the DGAT activity, resulted in a 44% net increase in oil content. Similar experiments conducted wherein the TmDGAT1 was over-expressed in B. napus, showed that these transgenic lines exhibited oil content increases of 3.5-4.5%, and 20-30 mg oil per 100 seeds on average, which translated to as much as a 15% net overall oil increase, when compared to the average pSE plasmid-only control lines. In addition, the average 100-seed-weight in one napin:TmDGAT1 transgenic lines 15C, was increased by 16%. That this range of effects were observed in the $T_1$ generation where the genotype is hemizygous, would suggest larger increments can likely be expected in future homozygous generations. Collectively, these findings strongly support our previous research wherein the *Arabidopsis thaliana* DGAT1 was over-expressed in WT *A. thaliana* to achieve similar trends (Jako et al., 2001). Recently, we have also over-expressed the *Arabidopsis* DGAT1 in *B. napus* cv Quantum and in the $T_4$ generation, have homozygous lines exhibiting overall oil content increases of 10 to 21% in the greenhouse and 7 to 13% in the field; seed weights were also increased (Weselake et al, 2006; Zou et al, 2006).

Therefore, in light of the current result with the TmDGAT1 and cumulative findings with the AthaIDGAT1, the general utility of over-expressing DGAT1 genes for crop improvement is now very clear.

These findings support earlier biochemical evidence that DGAT is rate-limiting for the production of TAGs in developing seed (Perry et al., 1999; see reviews by Weselake, 2005 and Lung and Weselake, 2006). More importantly, the implications of transgenically manipulating DGAT expression to improve oil content are especially important for the Canada's canola industry—Canola (*Brassica napus* and *B. rapa*) is a $2.5 billion/year industry in Canada, with the Prairies producing the bulk of the nation's crop. It has been estimated that a 1% increase in seed oil content would translate into an increase of $35-55 million/year annually for the oilseed crushing and processing industry (Canola Council of Canada; c.f. Weselake et al., 2006).

Previous to this, we had shown that seed-specific expression of another acyltransferase, a mutant yeast LPAAT (SLC1-1) gene, in high erucic Brassica germplasm resulted in increased oil and erucoyl content, and seed weight (Zou, 1997; Katavic et al, 2000; Taylor et al, 2001; Zou et al, 2000). Recently, studies in human and animal systems have shown that a gene encoding microsomal glycerol-3-phosphate acyltransferase may be rate-limiting for the synthesis and accumulation of TAGs in lipogenic tissues (Cao et al., 2006). A yeast gene coding for cytosolic glycerol-3-phosphate dehydrogenase (gpd1) was expressed in transgenic oilseed rape under the control of the seed-specific napin promoter. Similar to our result cited above, a twofold increase in glycerol-3-phosphate dehydrogenase activity led to a three- to fourfold increase in the level of glycerol-3-phosphate in developing seeds, resulting in a 40% increase in the final lipid content of the seed (Vigeolas et al., 2007).

Seed-specific expression of the TmDGAT1 was able to complement the low TAG and fatty acid compositional mutant phenotype of the AS11 *Arabidopsis* line. In the WT *Arabidopsis* lines over-expressing the TmDGAT1, there was a consistent, but small (2-3%) increase in the total proportion of mono-unsaturated fatty acids (18:1+20:1) with a concomitant decrease in the proportion of 18:3 in seed TAGs (data not shown) which is perhaps at least partially explained by the relative selectivity of DGAT1s for mono-over poly-unsaturated fatty acyl-CoAs. However, despite the selectivity of the TmDGAT1 for synthesizing trierucin, neither set of TmDGAT1 *A. thaliana* transgenics displayed any significant increase in the proportion of seed oil erucic acid compared to wild type. This is no doubt because there is no significant dierucin in wild-type *Arabidopsis* seed oil (Taylor et al, unpublished) and because the overall proportion of 22:1 is extremely low, on the order of a few percent at most.

A recent study on tung tree DGATs suggested that in plants containing unusual fatty acids, DGAT2 (type 2 DGAT) may play a more important role on channeling unusual fatty acids into seed storage oils (Shockey et al., 2006). However, in the AS11 mutant line, during seed development it is known that there is a "bottleneck" in the Kennedy pathway wherein the DAG pool is increased 8-fold and the DAG/TAG ratio is increased due to the lesion in DGAT1 (Katavic et al. 1995; Zou et al, 1999). Given this finding, the potential contribution of a DGAT2 to the metabolism of DAG to TAG in *Arabidopsis* developing seed needs further study. In this context, repeated attempts to identify a DGAT2 gene using PCR according to the method described by Shockey et al (2006) or scanning 20,000 ESTs in the nasturtium genome, was unsuccessful, therefore suggesting that TmDGAT1 may be the sole acyl-CoA-dependent DGAT in *T. majus*.

*T. majus* is the only know source of trierucin and yet despite earlier studies (Pollard and Stumpf, 1980; Fehling et al., 1990; Löhden and Frentzen, 1992) the mechanism by which it accumulates this TAG is not entirely clear. With respect to engineering trierucin production in e.g. HEAR *B. napus* or *B. carinata*, over the past decade there have been several studies wherein genes involved in either the synthesis or utilization of erucoyl moieties have been cloned and transgenically expressed in HEAR backgrounds: In terms of TAG assembly, LPAATs more selective with respect to utilization of erucoyl-CoA than the other two acyltransferases of the Kennedy pathway have been targeted (Ichihara et al., 1987; Oo and Huang, 1989; Frentzen, 1993). The LPAAT present in meadowfoam (*Limnanthes* spp.) seed extracts efficiently incorporates 22:1 into sn-2 position of lyso-phosphatidic acid (Cao et al., 1990; Taylor et al, 1990; Laurent and Huang, 1992; Löhden and Frentzen, 1992). However, transgenic expression of the meadowfoam LPAAT gene in HEAR *B. napus* resulted in only trace proportions of trierucin being synthesized and the actual overall proportion of 22:1 decreased (Brough et al, 1996; Weier et al, 1997; Münster et al; 1998). In contrast to a previous study by Lohden & Frentzen (1992), we have consistently observed that *T. majus* has a low but measurable LPAAT activity with 22:1-CoA (Taylor et al., 1990; 1993a & 1993b; 1995). In the current study, we have evidence of the preference of TmDGAT1 to utilize 22:1-CoA, most notably in the synthesis of trierucin, by the recombinant protein in vitro. Therefore, the additional ongoing efforts in our lab to isolate the TmLPAAT gene and/or a TmDGAT2 gene (if there is one) may help us better understand the mechanism whereby trierucin is assembled in *T. majus* seed oils and to exploit a combination of these genes for genetic engineering.

Previous studies in our group have also focused on whether the supply of erucic acid is strong enough in HEAR *B. napus* to support the synthesis of ultra-high erucoyl seed oils. In this instance the primary gene targets are (1) elongases for maximal synthesis of VLCFAs from oleic acid, and (2) the silencing of microsomal oleoyl- and linoleoyl-desaturases which will theoretically "free up" additional oleic acid for elongation. In both cases, it was reasoned that increases in the erucoyl pool would increase the proportion of erucic acid in the seed oils. Both of these strategies have been successful to a degree. In particular, we have isolated a *T. majus* FAE1 with a high specificity for extending 20:1-CoA to yield 22:1 as its primary product. Seed-specific expression of this nasturtium elongase in *Arabidopsis* resulted in a strong increase in the overall proportion of erucic acid in TAGs (Mietkiewska et al., 2004) and more recent studies of over-expression of the TmFAE1 in *B. carinata* have shown erucic increases from 37% in WT to as high as 49% in the transgenics (Taylor, Mietkiewska and Brost, 2006, unpublished). Partial silencing of FAD2 in *B. carinata* both by co-suppression and by antisense resulted in incremental increases in erucic acid in seed oils as well. In the case where a *B. napus* FAE1 has been co-expressed with a *Limnanthes* LPAAT (Weier et al, 1997; Münster et al, 1998), there was not a strong increase in erucic acid content and trierucin was of the order of 5-7% or less. Even when we observed an significant increase in the total proportion of 22:1 in *B. napus* co-expressing the *Arabidopsis* FAE1 and the yeast sn-2 acyltransferase gene SLC1-1, there was not a significant accumulation of trierucin (Katavic et al. 2000; Taylor et al., 2001). If one "stacked" the *T. majus* genes encoding one or more acyltransferases (e.g. the current TmD-GAT1; an LPAAT) or other nasturtium enzymes showing the ability, or indeed a preference for, utilizing erucoyl moieties in conjunction with e.g. the *T. majus* FAE1, our past experience has shown that there is also likely to be a level of regulation more sophisticated than simple acyl availability or specificity affecting whether one can achieve high levels of trierucin in the seed oil of transgenic HEAR *Brassica* oilseeds.

Previously, we had shown that an insertional mutation in the *Arabidopsis* DGAT1 gene in mutant AS11 resulted in a repeat of exon 2, translating to a 27 amino acid repeat of a motif containing the last four residues of a putative acyl-CoA binding motif as well as the active site catalytic residues $R^{149}$-L-I-I-$E^{153}$-$N^{154}$ (Katavic et al., 1995; Zou et al., 1999). This mutation resulted in a 3.5-fold decrease in DGAT activity and an increase in the DAG/TAG ratio (i.e. an increase in the DAG pool) during seed development, which resulted in a 30% decrease in mature seed oil content. This result implies the importance of structural integrity surrounding this motif. Perhaps it creates catalytic ambiguity. Clearly, tandem catalytic sites conferred no advantage with respect to oil deposition. We have since determined that while the *A. thaliana* AS11 cDNA could be expressed in the yeast quadruple mutant H1246MAT, and while the gene was transcribed and translated, the resulting AS11 DGAT protein is not functional (Xu, Francis and Taylor unpublished). In this DGAT catalytic motif, the R is thought to abstract a proton from the hydroxyl group of diacylglycerol allowing nucleophilic attack on the thioester bond of the acyl-CoA. The positive charge on the R is suggested to be stabilized by the negative charge on the nearby glutamate (E) residue. In the current study, when this glutamate $E^{145}$ on the TmDGAT is replaced with valine, enzyme activity was severely reduced (by 43%) but not eliminated. This finding suggests that in absence of a negatively-charged glutamate, the positive charge on the arginine is destabilized, leading to lower enzyme activity. This result may indicate that the requirement for charge stabilization is not absolute. Alternately, it is possible that this requirement could be partially afforded by the proximal Asp (D) at residue 155. Regardless, further studies are necessary to determine the role of this motif in catalysis and the of the E residue in particular.

Weselake et al (2006) have studied the acyl-CoA binding properties of a recombinant poly-His-tagged 13.3 kDa N-terminal fragment (residues 1-116) of the *B. napus* DGAT1 spanning a putative acyl-CoA binding signature (residues 99-116) motif. The enzyme fragment, which self-associated to form a tetramer, exhibited a stronger affinity for erucoyl-CoA (KD=2 (M)) than oleoyl-CoA KD=17 (M) in a Lipidex 100 binding assay, with the binding process displaying positive co-operativity. It was proposed that the acyl-CoA binding site in this N-terminal fragment may be responsible for trapping cytosolic acyl-CoA for use by the (downstream) catalytic site (described above).

While one recent study examined the effects of amino acid substitutions on enzyme stability and phosphorylation of oleate desaturases (Tang et al., 2005) and another has focused on motifs essential for signaling and localization of tung tree DGATs 1 and 2 to different subdomains of the ER (Shockey et al, 2006), the current study is the first to perform site-directed mutagenesis (SDM) studies conducted on putative functional regions/motifs of a plant DGAT enzyme.

Following SDM and expression of the recombinant TmD-GAT1 in a yeast quadruple mutant devoid of DGAT activity and unable to accumulate TAGs, a total loss of DGAT activity was observed with the mutagenesis of a single amino acid at residues Phenylalanine$^{439}$ (changed to an Arg) in a putative DAG binding motif, and Proline$^{216}$ (changed to an Arg) in the putative thiolase acyl-enzyme intermediate binding motif. Western blots showed that translation was not impaired and the strong band corresponding to the SDM TmDGAT1 proteins of the expected size were detected. Both of these mutations affect putative primary signature sites for substrate binding. Our results suggest that the hydrophobic integrity of the putative DAG binding site is critical; a change in the single most hydrophobic amino acid occurring within this amphiphilic/hydrophobic block may affect the binding domain for the diacylglycerol. The invariant Proline residue in the thiolase acyl-enzyme intermediate acyl-CoA binding motif is also clearly essential for DGAT activity. Substitution of this residue with a basic amino acid (arginine) may remove the capability of the proline to assist in making the acylthioester intermediate available to the diacylglycerol. That both of the point mutations we made resulted in a total loss of activity, indicates the critical role of each chosen residue in the respective site.

Mutagenesis of the a putative tyrosine protein kinase (phosphorylation) site in the fatty acid binding signature motif resulted in a near total loss (80% when mutating just the tyrosine) to complete loss (when mutating both the tyrosine and neighbouring tryptophan residues in this motif) of DGAT1 activity. A similar result has been observed in SDM studies of this type of motif (FYxDWWN) in yeast and human acyl-CoA sterol acyltransferases (Guo et al., 2001). At present, it is unclear as to whether this is due to the disruption of the capacity to activate the enzyme via phosphorylation at this site or, more probably, due to a dramatic alteration of the hydrophobicity in this region of the enzyme by replacement of both the Tyr and Trp residues with amphiphilic alanines, which, in turn, affects the ability of the site to accommodate or bind lipophilic fatty acyl groups. More study of this particular mutation is necessary, but its effect on DGAT1 activity is clearly important, and may constitute a means to down-regulate DGAT1 activity in a biotechnological context.

The SnRK1 (Sucrose non-fermenting (SNF)-related protein kinase-1) proteins are a class of Ser/Thr protein kinases that have been increasingly implicated in the global regulation of carbon metabolism in plants (Halford and Hardie, 1998). The consensus serine residue in the putative SnRK1 targeting motif thus present a possible phosphorylation site on plant DGAT1s and we propose that phosphorylation of this site may down-regulate the enzyme activity. Phosphorylation-mediated inhibition of enzyme function has been demonstrated by Tang et al. (2005); the serine-185 of FAD2-1 sequences is phosphorylated during soybean seed development, and the expression of phosphopeptide mimic mutations in yeast suggested that phosphorylation may down-regulate the expression of enzyme activity in vivo. In our study, there was a significant increase in recombinant DGAT activity (up to 125%) upon the mutagenesis of Ser[197] in the putative SnRK1 target site. The western blots showed the protein level of the mutated protein is similar to that of the wild type TmDGAT1 protein. Therefore because changing of Ser[197] imparts a strong up-regulation in DGAT activity, it is also strong evidence that the putative SnRK1 is a serine/threonine protein kinase target site. The enhanced capability to produce trierucin is an additional advantage of this mutation and will be useful in a biotechnology context. The Ser197-to-Alanine mutation provides a new means to enhance oil content of plant seeds; by transgenic over-expression of the mutated protein, enhanced DGAT activity results. This will result in enhanced oil content in transgenic oilseeds. We are currently taking two approaches to study the phosphorylation state of the TmDGAT1 protein (at this site), examining both the recombinant WT vs. mutagenized forms, as well as the native protein found in developing seeds of nasturtium: One is to perform a western blot with isolated protein fractions using a site-specific pSer anti-phosphopeptide antibody; another is to use Q-TOF MS/MS to attempt to identify and characterize site-specific phosphorylated peptides (vs. their absence in them mutated form) in a peptide digest (Larsen et al., 2005; Vyetrogon et al., 2006; Wan et al., 2007). Thus, transgenic experiments are currently underway to express both the SDM Ser[197] to Ala TmDGAT1 and WT TmDGAT1 in *Arabidopsis* developing seed to determine the effects of this alteration in the SnRK1 site on seed oil profiles. This will help us to understand the regulation of TmDGAT1 in its endogenous environment and will provide a new means to enhance oil content of plant seeds by expression of the mutated protein.

The negative regulation of DGAT activity via phosphorylation of S[197] constitutes the first report of post-translational regulation of plant DGAT activity. It has been hypothesized that the SnRK1 complex can be regulated by different metabolites according to the organs or tissues involved, e.g. source or sink (Polge and Thomas, 2006). In the developing seed sink, we conjecture, such regulation may be controlled by the size of the DAG pool (DAG is implicated as an initiator in a number of signal transduction cascades) or the relative ratio of key Kennedy pathway intermediates, such as e.g. the PC/DAG or TAG/DAG ratios. If, for example, the rate of storage TAG deposition adversely reduced the DAG available for membrane and other PL synthesis (e.g. PC, PE, PS, PI) during the exponential phase of seed development, then a regulatory mechanism for diverting DAG to PL rather than TAG synthesis, might be necessary. DGAT1 could join a growing list of key enzymes in different plant metabolic pathways, including nitrate reductase (NR), 3-hydroxymethyl-3-methylglutaryl-CoA reductase (HMGR), sucrose phosphate synthase (SPS) and trehalose phosphate synthase 5 (TPS5), which are coordinately regulated by SnRK1-catalyzed post-translational enzyme phosphorylation (Polge and Thomas, 2006).

The *T. majus* DGAT1 cloned and characterized herein has many of the features of other plant DGAT1s. Our study has focused on the utility of the gene, and ways in which it may be exploited/altered for biotechnology applications. Thus, we have demonstrated that over-expression of the gene behind a strong seed-specific promoter, can result in enhanced oil content and seed weight. These demonstrations have been conducted in both the model crucifer, *Arabidopsis thaliana*, as well as in *Brassica napus*. The TmDGAT1 enzyme is capable of synthesizing trierucin and has a strong capacity to use VLCF-acyl-CoAs, consistent with the fatty acid phenotype of nasturtium seed oil. Several key motifs have been studied using site-directed mutagenesis, among these, a DAG binding motif and a the putative thiolase acyl-enzyme intermediate binding motif; DGAT1 activity can be abolished by mutagenesis of a single amino acid at residue Phenylalanine[439] (changed to an Arg) and at residue Proline[216] (changed to an Arg) in the respective motifs. An up-regulation of DGAT1 activity, by as much as 125%, can be obtained by SDM of a putative SnRK1 binding motif, where a key serine residue is substituted by an alanine. Mutagenesis of the various sites described above, followed by strong seed-specific expression of the mutated transgene, will therefore have utility for both down- and up-regulating DGAT1 activity. The resultant seed oil content profile changes have commercial relevance for both increasing oil for greater productivity, or decreasing TAG and enhancing the proportions of DAG to allow a healthier, lower calorie oil to be created in situ.

REFERENCES

The contents of the entirety of each of which are incorporated by this reference.

Altschul S F, Gish W, Miller W, Myers E W, Lipman D J (1990) Basic local alignment search tool. J Mol Biol 215: 403-410.

Banas A, Dahlqvist A, Stahl U, Lenman M, Stymne S (2000) The involvement of phospholipid:diacylglycerol acyltransferases in triacylglycerol production. Biochem Soc Trans 28: 703-705.

Billheimer J T, Cromley D A, Kempner E S (1990) The functional size of acyl-coenzyme A (CoA):cholesterol acyltransferase and acyl-CoA hydrolase as determined by radiation inactivation. J Biol Chem. 265: 8632-8635.

Bonaldo M F, Lennon G, Soares M B (1996) Normalization and Subtraction: Two Approaches to Facilitate Gene Discovery. Genome Research 6: 791-806.

Bouvier-Nave P, Benveniste P, Oelkers P, Sturley S L, Schaller H (2000) Expression in yeast and tobacco of plant cDNAs encoding acyl CoA:diacylglycerol acyltransferase. Eur J Biochem. 267: 85-96.

Bradford M M (1976) A rapid and sensitive method for the quantification of microgram quantities of protein utilizing the principle of protein-dye binding. Anal Biochem 72: 248-254.

Brough C L, Coventry J M, Christie W W, Kroon J T M, Brown A P, Barsby T L, Slabas A R (1996) Towards genetic engineering of triacylglycerols of defined fatty acid composition: major changes in erucic acid content at the sn-2 position affected by the introduction of a 1-acyl-sn-glycerol-3-phosphate acyltransferase from *Limnanthes douglasii* into oil seed rape. Molecular Breeding 2: 133-142.

Cao J, Li J-L, Li D, Tobin J F, Gimeno R E (2006) Molecular identification of microsomal acyl-CoA:glycerol-3-phosphate acyltransferase, a key enzyme in de novo triacylglycerol synthesis. Proc. Nat'l Acad Sci. 103: 19695-19700.

Cao Y Z, Huang A H C (1987) Acyl Coenzyme A preference of diacylglycerol acyltransferase from maturing sees of *Cuphea*, maize, rapeseed and canola. Plant Physiol. 84: 762-765.

Cao Y Z Huang A H C (1986) Diacylglycerol acyltransferase in maturing oil seeds of maize and other species. Plant Physiol. 82: 813-820.

Cao Y Z, Oo K-C, Huang A H C (1990) Lysophosphatidic acid acyltransferase in the microsomes from maturing seeds of meadowfoam (*Limnanthes alba*). Plant Physiol 94: 1199-1206.

Cases S, Smith S J, Zheng Y W, Myers H M, Lear S R, Sande E, Novak S, Collins C, Welch C B, Lusis A J, Erickson S, Farese R V Jr (1998) Identification of a gene encoding an acyl CoA:diacylglycerol acyltransferase, a key enzyme in triacylglycerol synthesis. Proc Natl Acad Sci USA 95:13018-13023.

Clough S J, Bent A F (1998) Floral dip: a simplified method for *Agrobacterium*-mediated transformation of *Arabidopsis thaliana*. Plant J 16: 735-743.

Chang T Y, Chang C C, Cheng D (1997) Acyl-coenzyme A:cholesterol acyltransferase. Annu Rev Biochem 66: 613-638.

Dahlqvist A, Stahl U, Lenman M, Banas A, Lee M, Sandager L, Ronne H, Stymne S (2000) Phospholipid:diacylglycerol acyltransferase: An enzyme that catalyzes the acyl-CoA-independent formation of triacylglycerol in yeast and plants. Proc Natl Acad Sci USA 97: 6487-6492.

Daniel J, Deb C, Dubey V S, Sirakova T D, Abomoelak B, Morbidoni H R, Kolattukudy P E (2004) Induction of a novel class of diacylglycerol acyltransferases and triacylglycerol accumulation in *Mycobacterium tuberculosis* as it goes into a dormancy-like state in culture. J Bacteriol 186: 5017-5030.

DeBlock M, DeBrouwer D, Tenning P (1989) Transformation of *Brassica napus* and *Brassica oleracea* using *Agrobacterium tumefaciens* and the expression of the bar and neo genes in the transgenic plants. Plant Physiol 91: 694-701.

Fehling E, Murphy D J, Mukherjee K D (1990) Biosynthesis of Triacylglycerols Containing Very Long Chain Monounsaturated Acyl Moieties in Developing Seeds. Plant Physiol 94: 492-498.

Fehling E, Mukherjee K D (1991) Acyl-CoA elongase from a higher plant (*Lunaria annua*): metabolic intermediates of very-long-chain acyl-CoA products and substrate specificity. Biochim Biophys Acta 1082: 239-246.

Fehling E, Lessire R, Cassagne C, Mukherjee K D (1992) Solubilization and partial purification of constituents of acyl-CoA elongase from *Lunaria annua*. Biochim Biophys Acta 1126: 88-94.

Focks N, Benning C (1998) wrinkled1: A novel, low-seed-oil mutant of *Arabidopsis* with a deficiency in the seed-specific regulation of carbohydrate metabolism. Plant Physiol 118: 91-101.

Frentzen M (1993) Acyltransferases and triacylglycerols. In T S Moore Jr, ed, Lipid Metabolism in Plants. CRC Press, Boca Raton, Fla., pp 195-230.

Griffiths G, Stymne S, Stobart A K (1988) Phosphatidylcholine and its relationship to triacylglycerol biosynthesis in oil-tissues. Phytochemistry 27: 2089-2093.

Guo Z, Cromley D, Billheimer J T, Sturley S L (2001) Identification of potential substrate-binding sites in yeast and human acyl-CoA sterol acyltransferases by mutagenesis of conserved sequences. J Lipid Res 42: 1282-1291.

Halford N G, Hardie D G (1998) SNF1-related protein kinases: global regulators of carbon metabolism in plants? Plant Mol Biol 37: 735-748.

He X, Turner C, Chen G Q, Lin J-T, McKeon TA (2004) Cloning and Characterization of a cDNA Encoding Diacylglycerol Acyltransferase from Castor Bean. Lipids 39: 311-318.

Hobbs D H, Lu C, Hills M J. (1999) Cloning of a cDNA encoding diacylglycerol acyltransferase from *Arabidopsis thaliana* and its functional expression. FEBS 452:145-149.

Hogge L R, Taylor D C, Underhill E W (1991) Characterization of castor bean neutral lipids by mass spectrometry/mass spectrometry. J Am Oil Chem Soc 68: 863-868.

Ichihara K, Asahi T, Fugii S (1987) 1-acyl-sn-glycerol-3-phosphate acyltransferase in maturing safflower seeds and its contribution to the non-random fatty acid distribution of triacylglycerol. Eur J Biochem 167: 339-347.

Ichihara K, Takahashi T, Fujii S (1988) Diacylglycerol acyltransferase in maturing safflower seeds: its influences on the fatty acid composition of triacylglycerol and on the rate of triacylglycerol synthesis. Biochim Biophys Acta 958: 125-129.

Jadhav A, Katavic V, Marillia E-F, Giblin E M, Barton D L, Kumar A, Sonntag C, Babic V, Keller W A and Taylor D C (2005) Increased levels of erucic acid in *Brassica carinata* by co-suppression and antisense repression of the endoegenous FAD2 gene. Metabolic Engineering 7: 215-220.

Jako C, Kumar A, Wei Y, Zou J, Barton D L, Giblin E M, Covello P S, Taylor D C (2001) Seed-specific over-expression of an *Arabidopsis* cDNA encoding a diacylglycerol acyltransferase enhances seed oil content and seed weight. Plant Physiol 126: 861-874.

Kalscheuer R, Luftmann H, Steinbuchel A (2004) Synthesis of novel lipids in *Saccharomyces cerevisiae* by heterologous expression of an unspecific bacterial acyltransferase. Appl Environ Microbiol 70: 7119-7125.

Katavic V, Reed D W, Taylor D C, Giblin E M, Barton D L, Zou J, MacKenzie S L, Covello P S, Kunst L (1995) Alteration of Seed Fatty Acid Composition by an Ethyl Methanesulfonate-Induced Mutation in *Arabidopsis thaliana* Affecting Diacylglycerol Acyltransferase Activity. Plant Physiol 108: 399-409.

Katavic V, Friesen W, Barton D L, Gossen K K, Giblin E M, Luciw T, An J, Zou J, MacKenzie S L, Keller W A, Males D, Taylor D C (2000) Utility of the *Arabidopsis* FAE1 and Yeast SLC1-1 Genes for Improvements in Erucic Acid and Oil Content in Rapeseed. Biochem. Soc. Trans. 28(6): 935-937.

Katavic V, Zou J, Jako C, Marillia E F, Taylor D C (2001) Improving erucic acid and oil content in high erucic acid germplasm: Targets and strategies. Recent Res Devel Plant Biol 1: 131-142.

Katavic V, Mietkiewska E, Barton D L, Giblin E M, Reed D W, Taylor D C (2002) Restoring enzyme activity in non-functional low erucic acid *Brassica napus* fatty acid elongase 1 by a single amino acid substitution. Eur J Biochem 269: 5625-5631.

Koncz C, Schell J (1986) The promoter of TL-DNA gene 5 controls the tissue-specific expression of chimaeric genes carried by a novel type of *Agrobacterium* binary vector. Mol Gen Genet 204: 383-396.

Knutzon D S, Lardizabal K D, Nelsen J S, Bleibaum J L, Davies H M, Metz J G (1995) Cloning of a Coconut Endosperm cDNA Encoding a 1-Acyl-sn-Glycerol-3-Phosphate Acyltransferase That Accepts Medium-Chain-Length Substrates. Plant Physiol 109: 999-1006.

Lardizabal K D, Mai J T, Wagner N W, Wyrick A, Voelker T, Hawkins D J (2001) DGAT2 is a new diacylglycerol acyltransferase gene family: purification, cloning, and expression in insect cells of two polypeptides from *Mortierella ramanniana* with diacylglycerol acyltransferase activity. J Biol Chem 276: 38862-38869.

Larsen M R, Thingholm T E, Jensen O N, Roepstorff P, Jorgensen T J D (2005) Highly selective enrichment of phosphorylated peptides from peptide mixtures using titanium dioxide microcolumns. Molecular and Cellular Proteomics 4: 873-866.

Lassner M W, Levering C K, Davies H M, Knutzon D S (1995) Lysophosphatidic acid acyltransferase from meadowfoam mediates insertion of erucic acid at the sn-2 position of triacylglycerol in transgenic rapeseed oil. Plant Physiol 109: 1389-1394.

Laurent P, Huang A H C (1992) Organ- and development-specific acyl coenzyme A lysophosphatidate acyltransferases in palm and meadowfoam. Plant Physiol 99: 1711-1715.

Leonard C (1994) Sources and commercial applications of high erucic vegetable oils. Lipid Technology 4: 79-83.

Lehner R, Kuksis A (1996) Biosynthesis of triacylglycerols. Prog in Lipid Res 35: 169-201.

Lewin T M, Wang P, Coleman R A (1999) Analysis of amino acid motifs diagnostic for the sn-glycerol-3-phosphate acyltransferase reaction. Biochemistry 38: 5764-5771.

Li Y, Beisson F, Pollard M, Ohlrogge J (2006) Oil content of *Arabidopsis* seeds: The influence of seed anatomy, light and plant-to-plant variation. Phytochemistry. 67: 904-15.

Löhden and Frentzen (1992) Triacylglycerol biosynthesis in developing seeds of *Tropaeolum majus* L. and *Limnanthes douglasii* R. Br. Planta 188:215-224.

Lu C L, de Noyer S B, Hobbs D H, Kang J, Wen Y, Krachtus D, Hills M J (2003) Expression pattern of diacylglycerol acyltransferase-1, an enzyme involved in triacylglycerol biosynthesis, in *Arabidopsis thaliana*. Plant Mol Biol 52: 31-41.

Lung A-C, Weselake R J (2006) Diacylglycerol acyltransferase: A key mediator of plant triacylglycerol synthesis. Lipids. 41: 1073-1088.

Mancha M, Stymne S (1997) Remodelling of triacylglycerols in microsomal preparations from developing castor bean (*Ricinus communis* L.) endosperm. Planta 203: 51-57.

Mhaske M, Beljilali K, Ohirogge J, Pollard M (2005) Isolation and characterization of an *Arabidopsis thaliana* knockout line for phospholipid: diacylglycerol transacylase gene (At5g13640). Plant Physiol Biochem. 43:413-417.

Mietkiewska E, Giblin E M Wang S, Barton D L, Dirpaul J, Brost J M, Katavic V and Taylor D C (2004) Seed-specific heterologous expression of a *T. majus* FAE gene in *Arabidopsis* results in a dramatic increase in the proportion of erucic acid. Plant Physiol 136: 2665-2675.

Milcamps A, Tumaney A W, Paddock T, Pan D A, Ohlrogge J, Pollard M (2005) Isolation of a gene encoding a 1,2-diacylglycerol-sn-acetyl-CoA acetyltransferase from developing seeds of *Euonymus alatus*. J Biol Chem 280: 5370-5377.

Moloney M M, Walker J M, Sharma K K (1989) High efficiency transformation of *Brassica napus* using *Agrobacterium* vectors. Plant Cell Reports 8: 238-242.

Münster A, Grafin Z U, Lühs W, Borchardt D S, Wolter F P, Frentzen M (1998) Experiments to optimize the channeling of erucic acid into the sn-2 position of transgenic oil of *Brassica napus* L. In: Advances in Plant Lipid Research (Sanchez J, Cerdá-Olmedo E, Martinez-Force E, eds). Secretariado depublicaciones de la Universidad de Sevilla, Sevilla, Spain. pp. 671-674.

Murphy D J, Vance J (1999) Mechanisms of lipid-body formation. Trends Biochem Sci 24: 109-115.

Nakai K, Kanehisa M (1992) A knowledge base for predicting protein localization sites in eukaryotic cells. Genomics 14: 897-911.

Nykiforuk C L, Furukawa-Stoffer T L, Huff P W, Sarna M, Laroche A, Moloney M M, Weselake R J (2002) Characterization of cDNAs encoding diacylglycerol acyltransferase from cultures of *Brassica napus* and sucrose-mediated induction of enzyme biosynthesis. Biochim Biophys Acta 1580: 95-109.

Oelkers P, Behari A, Cromley D, Billheimer J T, Sturley S L (1998) Characterization of two human genes encoding acyl coenzyme A:cholesterol acyltransferase-related enzymes. J Biol Chem 273: 26765-26771.

Oo K C, Chew Y H (1992) Diacylglycerol Acyltransferase in Microsomes and Oil Bodies of Oil Palm Mesocarp. Plant Cell Physiol 33: 189-195.

Perry H J, Bligny R, Gout E, Harwood J L (1999) Changes in Kennedy pathway intermediates associated with increased triacylglycerol synthesis in oilseed rape. Phytochemistry 52: 799-804.

Perry H J, Harwood J L (1993a) Changes in the lipid content of developing seeds of *Brassica napus*. Phytochemistry 32: 1411-1415.

Perry H J, Harwood J L (1993b) Radiolabelling studies of acyl lipids in developing seeds of *Brassica napus*: use of [1-$^{14}$C]acetate precursor. Phytochemistry 33: 329-333.

Persson B, Argos P (1997) Prediction of membrane protein topology utilizing multiple sequence alignments. J Protein Chem 16: 453-457.

Polge C, Thomas M (2006) SNF1/AMPK/SnRK1 kinases, global regulators at the heart of energy control. Trends in Plant Science 12: 20-28.

Pollard M R, Stumpf P K (1980) Long Chain (C20 and C22) Fatty Acid Biosynthesis in Developing Seeds of *Tropaeolum majus*. Plant Physiol 66: 641-648.

Routaboul J M, Benning C, Bechtold N, Caboche M, Lepiniec L (1999) The TAG1 locus of *Arabidopsis* encodes for a diacylglycerol acyltransferase. Plant Physiol and Biochem 37: 831-840.

Saha S, Enugutti B, Rajakumari S, Rajasekharan R (2006) Cytosolic triacylglycerol biosynthetic pathway in oilseeds. Molecular cloning and expression of peanut cytosolic diacylglycerol acyltransferase. Plant Physiol 141:1533-1543.

Sambrook J, Fritsch E F, Maniatis T (1989) Molecular Cloning, A Laboratory Manual, Ed 2. Cold Spring Harbor Laboratory Press, Cold Spring Harbor, N.Y.

Sandager L, Gustavsson M H, Stahl U, Dahlqvist A, Wiberg E, Banas A, Lenman M, Ronne H, Stymne S (2002) Storage lipid synthesis is non-essential in yeast. J Biol Chem 277: 6478-6482.

Shockey J M, Gidda S K, Chapital D C, Kuan J C, Dhanoa P K, Bland J M, Rothstein S J, Mullen R T, Dyer J M (2006) Tung Tree DGAT1 and DGAT2 have nonredundant functions in triacylglycerol biosynthesis and are localized to different subdomains of the endoplasmic reticulum. Plant Cell 15: 1872-1887.

Saha S, Enugutti B, Rajakumari S, Rajasekharan R (2006) Cytosolic triacylglycerol biosynthetic pathway in oilseeds. Molecular cloning and expression of peanut cytosolic diacylglycerol acyltransferase. Plant Physiol 141:1533-1543

Slocombe S P, Piffanelli P, Fairbairn D, Bowra S, Hatzopoulos P, Tsiantis M, Murphy D J (1994) Temporal and Tissue-Specific Regulation of a *Brassica napus* Stearoyl-Acyl Carrier Protein Desaturase Gene. Plant Physiol 104: 1167-1176.

Stahl U, Carlsson A S, Lenman M, Dahlqvist A, Huang B, Banas W, Banas A, Stymne S (2004) Cloning and functional characterization of a phospholipid:diacylglycerol acyltransferase from *Arabidopsis*. Plant Physiol 135: 1324-1335.

Stobart K, Mancha M, Lenman M, Dahlqvist A, Stymne S (1997) Triacylglycerols are synthesised and utilized by transacylation reactions in microsomal preparations of developing safflower (*Carthamus tinctorius* L.) seeds. Planta 203: 58-66.

Stoveken T, Kalscheuer R, Malkus U, Reichelt R, Steinbuchel A (2005) The wax ester synthase/acyl coenzyme A:diacylglycerol acyltransferase from *Acinetobacter* sp. strain ADP1: characterization of a novel type of acyltransferase. J Bacteriol 187: 1369-1376.

Stymne S, Stobart A K (1987) Triacylglycerol biosynthesis. The Biochemistry of Plants, Vol. 9 Lipids: Structure and Function. PK Stumpf, ed, Academic Press, New York, pp 175-214.

Tang G Q, Novitzky W P, Carol Griffin H, Huber S C, Dewey R E (2005) Oleate desaturase enzymes of soybean: evidence of regulation through differential stability and phosphorylation. Plant J 44: 433-446.

Taylor D C, Thompson L W, MacKenzie S L, Pomeroy M K, Weselake R J (1990) Target Enzymes for Modification of Seed Storage Lipids. In: Sixth Crucifer Genetics Workshop Proceedings, (McFerson J R, Kresovich S, Dwyer S G, eds), USDA-ARS Plant Genetic Resources Unit, Cornell University, Geneva, N.Y., pp 38-39.

Taylor D C, Weber N, Barton D L, Underhill E W, Hogge L R, Weselake R J, Pomeroy M K (1991) Triacylglycerol Bioassembly in Microspore-Derived Embryos of *Brassica napus* L. cv Reston. Plant Physiol 97: 65-79.

Taylor D C, Barton D L, Rioux K P, MacKenzie S L, reed D W, Underhill E W, Pomeroy M K, Weber N (1992a) Biosynthesis of Acyl Lipids Containing Very Long Chain Fatty Acids in Microspore-Derived and Zygotic Embryos of *Brassica napus* L cv Reston. Plant Physiol 99: 1609-1618.

Taylor D C, Weber N, Hogge L R, Underhill E W, Pomeroy M K (1992b) Formation of Trierucoylglycerol (Trierucin) from 1,2-Dierucoylglycerol by a Homogenate of Microspore-Derived Embryos of *Brassica napus* L. J Am Oil Chem Soc 69: 355-358.

Taylor D C, Kunst L MacKenzie S L (1993a) Bioassembly of Storage Lipids in Oilseed Crops; Target: Trierucin. In: Progress in New Crops, (Janick J, Simon J E eds) Wiley, New York, pp 181-191.

Taylor D C, Magus J R, Bhella R, Zou J-T, MacKenzie S L, Giblin E M, Pass E W Crosby W L (1993b) Biosynthesis of Triacylglycerols in *Brassica napus* L. cv Reston; Target: Trierucin. In: Seed Oils for the Future, (MacKenzie, S. L. and Taylor, D. C. eds.) American Oil Chemists' Society, Champaign, Ill., pp 77-102.

Taylor D C, Barton D L, Giblin E M, MacKenzie S L, Van Den B C, McVetty P (1995) Microsomal Lyso-Phosphatidic Acid Acyltransferase from a *Brassica oleracea* Cultivar Incorporates Erucic Acid into the sn-2 Position of Seed Triacylglycerols. Plant Physiol 109: 409-420.

Taylor D C, Katavic V, Zou J, MacKenzie S L, Keller W A, An J, Friesen W, Barton D L, Gossen K K, Giblin E M, Ge Y, Dauk M, Luciw T, Males D (2001) Field-testing of transgenic rapeseed cv. Hero transformed with a yeast sn-2 acyltransferase results in increased oil content, erucic acid content and seed yield. Molecular Breeding 8: 317-322.

Vigeolas H, Waldeck P, Zank T, Geigenberger P (2007) Increasing seed oil content in oil-seed rape (*Brassica napus* L.) by over-expression of a yeast glycerol-3-phosphate dehydrogenase under the control of a seed-specific promoter. Plant Biotechnology Journal 5: 431-441.

Vyetrogon K, Tebbji F, Olson D J H, Ross A R S, Matton D P (2007) A comparative proteome and phosphoproteome analysis of differentially regulated proteins during fertilization in the self incompatible species *Solanum chacoense* Bitt. Proteomics 7: 232-247.

Wan L, Ross A R S, Yang J, Hegedus D D, Kermode A R (2007) Phosphorylation of 12S Globulin Cruciferin in Wild Type and abi1-1 Mutant *Arabidopsis thaliana* Seeds. Biochemical Journal 404: 247-256.

Wang C S, Vodkin L O (1994) Extraction of RNA from Tissues Containing High Levels of Procyanidins that Bind R N A. Plant Mol Bio Rep 12: 132-145.

Wang H W, Zhang J S, Gai J Y, Chen S Y (2006) Cloning and comparative analysis of the gene encoding diacylglycerol acyltransferase from wild type and cultivated soybean. Theor Appl Genet. 112: 1086-1097.

Weier D, Hanke C, Eikelkamp A, Lühs W, Dettendorfer J, Schaffert E, Möllers C, Freidt W, Wolter F P, Frentzen M (1997) Trierucoylglyccerol biosynthesis in transgenic plants of rapeseed (*Brassica napus* L.) Fett/Lipid 99: 160-165.

Weselake R J (2005) Storage lipids in Plant Lipids, Biology, Utilisation and Manipulation. Murphy D J (ed.), Blackwell Publishing Ltd, Cardiff, UK, pp 162-225.

Weselake R J, Shah S, Taylor D C, Zou J T, Laroche A, Moloney M, Rakow G, Raney J P, Harwood J (2007) Transformation of *Brassica napus* with diacylglycerol acyltransferase-1 results in increased seed oil content. In: Current advances in the Biochemistry and Cell Biology of Plant Lipids. Benning, C and Ohirogge, J. Eds. Proceedings of the 17th International Symposium on Plant Lipids, Aardvark Global Publishing Co., LLC, Salt Lake City, Utah. pp 232-234.

Weselake R J, Madhavji M, Szarka S J, Patterson N A, Wiehler W B, Nykiforuk C L, Burton T L, Boora P S, Mosimann S C, Foroud N A, Thibault B J, Moloney M M, Laroche A, Furukawa-Stoffer T L (2006) Acyl-CoA-binding and self-associating properties of a recombinant 13.3 KDa N-terminal fragment of diacylglycerol acyltransferase-1 from oilseed rape. BMC Biochemistry 7:24 (URL—http://www.biomedcentral.com/1471-2091/7/24).

Wolters-Arts M, Lush W M, Mariani C (1998) Lipids are required for directional pollen-tube growth. Nature 392: 818-821.

Xue L, McCune L M, Kleppinger-Sparace K F, Brown M J, Pomeroy M K, Sparace S A (1997) Characterization of the Glycerolipid Composition and Biosynthetic Capacity of Pea Root Plastids. Plant Physiol 113: 549-557.

Yamada K, Lim J, Dale J M, Chen H, Shinn P, Palm C J, Southwick A M, Wu H C, Kim C, Nguyen M, et al (2003) Empirical analysis of transcriptional activity in the *Arabidopsis* genome. Science 302: 842-846

Zheng Z, Xia Q, Dauk M, Shen W, Selvaraj G, Zou J (2003) *Arabidopsis* AtGPAT1, a Member of the Membrane-Bound Glycerol-3-Phosphate Acyltransferase Gene Family, is Essential for Tapetum Differentiation and Male Fertility. Plant Cell 15: 1872-1887.

Zimmermann P, Hirsch-Hoffmann M, Hennig L, Gruissem W (2004) GENEVESTIGATOR. *Arabidopsis* microarray database and analysis toolbox. Plant Physiol 136: 2621-2632.

Zou J-T, Brokx S J, Taylor D C (1996) Cloning of a cDNA encoding the 21.2 kDa oleosin isoform from *Arabidopsis thaliana* and down-regulation of its expression in a mutant defective in diacylglycerol acyltransferase activity. Plant Mol Biol 31: 429-433

Zou J-T, Katavic V, Giblin E M, Barton D L, MacKenzie S L, Keller W A, Hu X and Taylor D C (1997). Modification of Seed Oil Content and Acyl Composition in Brassicaceae by Expression of a Yeast sn-2 Acyltransferase Gene. Plant Cell 9: 909-923.

Zou J, Wei Y, Jako C, Kumar A, Selvaraj G, Taylor D C (1999) The *Arabidopsis thaliana* TAG1 mutant has a mutation in a diacylglycerol acyltransferase gene. Plant J 19: 645-653.

Zou J-T, et al. (Apr. 18, 2000) Modification of plant lipids and seed oils utilizing yeast SLC genes. U.S. Pat. No. 6,051,755.

Zou J-T, et al. (Mar. 21, 2006) Diacylglycerol acyltransferase gene from plants. U.S. Pat. No. 7,015,373.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. An isolated or purified polypeptide comprising the amino acid sequence as set forth in SEQ ID NO: 4, SEQ ID NO: 5, SEQ ID NO: 6, SEQ ID NO: 7, SEQ ID NO: 8 or SEQ ID NO: 9.

2. A method of increasing diacylglycerol acyltransferase activity in a cell comprising expressing a polypeptide comprising the amino acid sequence as set forth in SEQ ID NO: 6 in the cell.

3. The method according to claim 2, wherein the cell is a cell of an oilseed plant.

4. The method according to claim 3, wherein the oilseed plant is *Arabidopsis* spp., *Brassica napus, Brassica rapa, Brassica carinata, Brassica juncea,* or *Camelina sativa.*

5. The method according to claim 4, wherein the oilseed plant is of *Borago* spp., *Ricinus* spp., *Theobroma* spp., *Gossypium* spp., *Crambe* spp., *Cuphea* spp., *Linum* spp., *Lesquerella* spp., *Limnanthes* spp., Linola, *Tropaeolum* spp., *Olea* spp., *Elaeis* spp., *Arachis* spp., *Carthamus* spp., *Glycine* spp., *Soja* spp., *Helianthus* spp. or *Vernonia* spp.

6. A method of decreasing diacylglycerol acyltransferase activity in a cell comprising expressing a polypeptide comprising the amino acid sequence as set forth in SEQ ID NO: 4, SEQ ID NO: 5, SEQ ID NO: 7, SEQ ID NO: 8 or SEQ ID NO: 9 in the cell.

7. The method according to claim 6, wherein the cell is a cell of an oilseed plant.

8. The method according to claim 7, wherein the oilseed plant is *Arabidopsis* spp., *Brassica napus, Brassica rapa, Brassica carinata, Brassica juncea,* or *Camelina sativa.*

9. The method according to claim 7, wherein the oilseed plant is of *Borago* spp., *Ricinus* spp., *Theobroma* spp., *Gossypium* spp., *Crambe* spp., *Cuphea* spp., *Linum* spp., *Lesquerella* spp., *Limnanthes* spp., Linola, *Tropaeolum* spp., *Olea* spp., *Elaeis* spp., *Arachis* spp., *Carthamus* spp., *Glycine* spp., *Soja* spp., *Helianthus* spp. or *Vernonia* spp.

10. A method of converting a diacylglycerol to a triacylglycerol comprising: contacting a diacylglycerol with an acyl donor in the presence of a diacylglycerol acyltransferase having the amino acid sequence as set forth in SEQ ID NO: 6.

11. The method of claim 10, wherein the acyl donor comprises acyl-CoA.

12. The method of claim 10, wherein the diacylglycerol comprises dierucin, the triacylglycerol comprises trierucin and the acyl donor comprises erucoyl (22:1)-CoA.

* * * * *

SEQUENCE LISTING

```
<160> NUMBER OF SEQ ID NOS: 42

<210> SEQ ID NO 1
<211> LENGTH: 2090
<212> TYPE: DNA
<213> ORGANISM: Tropaeolum majus

<400> SEQUENCE: 1
acgcggggag ttttcaaaat catattatgc tttttcttca ctactgcatg aactttcttt      60
ctacttcttg caactgattt gtaatcctta cacatgtttc tagttttctc catataaaaa     120
aaatattctc tgagcttctc gattctctag agagagaagg ccaaaaaaaa atggcggtgg     180
cagagtcgtc acagaacacg acaaccatga gtggtcacgg cgactcggat ctcaacaatt     240
tccgtagaag gaaaccgagt tcctccgtga ttgaaccttc gtcgtccggt tttacatcca     300
ccaatggcgt accggcgact ggccacgtgg ctgagaatcg tgaccaggat cgggtagggg     360
ctatggagaa cgcaacagga tcggtcaact taattggaaa tggtggaggc gtggttatcg     420
ggaatgaaga gaaacaggta ggggagactg atatacgatt cacttaccgg ccttcgtttc     480
cggctcatcg gagggtgagg gagagtcctc ttagctctga tgcaatcttc aaacagagcc     540
atgcgggttt attcaacttg tgtatagtag tgctcattgc agtaaacagt aggcttatca     600
tcgaaaatct tatgaagtat ggttggttga tcgatactgg tttctggttt agctcaagat     660
cactgggtga ttggtccatc tttatgtgct gtcttacact cccaattttc ccacttgctg     720
cttttattgt tgaaaagctg gtgcagcgaa atcatatatc tgaacttgtt gctgttctcc     780
ttcatgtaat cgtttctacc gctgcagttt tatatccagt tattgtgatc ttaacgtgtg     840
attcggtgta tatgtctggt gtggtattga tgctctttgg ttgcattatg tggttgaagc     900
tggtgtcata tgcacatact agttctgata ttagaacact ggccaaatct ggctataagg     960
gggatgcgca ccccaattca accattgtga gttgctcata tgatgttagc ttgaagagtt    1020
tggcatactt catggttgct ccgacattat gttaccagcc tagctatcct cgttcgtcgt    1080
gtatccgcaa gggttgggtt gttcgtcaat tgtcaaaact aatagttttc ataggactca    1140
tggggttcat tatagaacaa tatattaatc ctatcgttcg aaattccaaa cacccattga    1200
aaggagattt tttatatgca atagaaagag ttttgaagct ttcagttcca aatctatatg    1260
tttggctttg catgttctac tctttttcc acctctggtt gaacatactg gctgagcttc    1320
ttcgctttgg tgatcgtgaa ttctacaaag attggtggaa tgcaaaaact gttgcggagt    1380
attggaaaat gtggaatatg cctgttcata gatggatggt tcgtcatcta tatttccct    1440 gtttgaggaa tgggataccc aaggaaggtg ccattattat cgcgttctta gtttctggtg    1500 cttttccatga gctctgcatt gcagttcctt gccacgtatt caagttatgg gcctttatag    1560
gcattatgtt tcaggttccc ttggtattga ttacgaatta tctacaagaa aagttcgata    1620
attctatggt gggcaatatg atcttctggt tcatcttctg catacttggc caacctatgt    1680
```

-continued

```
gtgtccttct atattaccat gacctgataa atctaaagga aaagtgaaaa aatggaagtt      1740
gcctatgctc agagtattcc tatcccaatg cacacattat atggttctgt acaatctgtg      1800
cccccttcat cctttacacg tacccatgct ggttcctgca cgatgatttg ccttttgttt      1860
gtaagcaata tttggagaga gtccaattta ggaagtgact agtgtggctt atatcttgta      1920
tactaccttt agtcatgggg gggtttttat attactagta ccaaaagtca agttgtatat      1980
gatttacggt ttagtttctt tcatgttttt tgttttgtg taaatatacg tttcatatat      2040
cactgttttt tcaaagtaaa atcaataata ccccatagat gttgaaactg               2090
```

<210> SEQ ID NO 2
<211> LENGTH: 1557
<212> TYPE: DNA
<213> ORGANISM: Tropaeolum majus

<400> SEQUENCE: 2

```
atggcggtgg cagagtcgtc acagaacacg acaaccatga gtggtcacgg cgactcggat       60
ctcaacaatt tccgtagaag gaaaccgagt tcctccgtga ttgaaccttc gtcgtccggt      120
tttacatcca ccaatggcgt accggcgact ggccacgtgg ctgagaatcg tgaccaggat      180
cgggtagggg ctatggagaa cgcaacagga tcggtcaact taattggaaa tggtggaggc      240
gtggttatcg ggaatgaaga gaaacaggta ggggagactg atatacgatt cacttaccgg      300
ccttcgtttc cggctcatcg gagggtgagg gagagtcctc ttagctctga tgcaatcttc      360
aaacagagcc atgcgggttt attcaacttg tgtatagtag tgctcattgc agtaaacagt      420
aggcttatca tcgaaaatct tatgaagtat ggttggttga tcgatactgg tttctggttt      480
agctcaagat cactgggtga ttggtccatc tttatgtgct gtcttacact cccaattttc      540
ccacttgctg ctttttattgt tgaaaagctg gtgcagcgaa atcatatatc tgaacttgtt      600
gctgttctcc ttcatgtaat cgtttctacc gctgcagttt tatatccagt tattgtgatc      660
ttaacgtgtg attcggtgta tatgtctggt gtggtattga tgctctttgg ttgcattatg      720
tggttgaagc tggtgtcata tgcacatact agttctgata ttagaacact ggccaaatct      780
ggctataagg gggatgcgca ccccaattca accattgtga gttgctcata tgatgttagc      840
ttgaagagtt tggcatactt catggttgct ccgacattat gttaccagcc tagctatcct      900
cgttcgtcgt gtatccgcaa gggttgggtt gttcgtcaat tgtcaaaact aatagttttc      960
ataggactca tggggttcat tatagaacaa tatattaatc ctatcgttcg aaattccaaa     1020
cacccattga aaggagattt tttatatgca atagaaagag ttttgaagct ttcagttcca     1080
aatctatatg tttggctttg catgttctac tctttttttcc acctctggtt gaacatactg     1140
gctgagcttc ttcgctttgg tgatcgtgaa ttctacaaag attggtggaa tgcaaaaact     1200
gttgcggagt attggaaaat gtggaatatg cctgttcata gatggatggt tcgtcatcta     1260
tattttccct gtttgaggaa tgggataccc aaggaaggtg ccattattat cgcgttctta     1320
gtttctggtg ctttccatga gctctgcatt gcagttcctt gccacgtatt caagttatgg     1380
gcctttatag gcattatgtt tcaggttccc ttggtattga ttacgaatta tctacaagaa     1440
aagttcagta attctatggt gggcaatatg atcttctggt tcatcttctg catacttggc     1500
caacctatgt gtgtccttct atattaccat gacctgataa atctaaagga aaagtga        1557
```

<210> SEQ ID NO 3
<211> LENGTH: 518
<212> TYPE: PRT
<213> ORGANISM: Tropaeolum majus -continued

<400> SEQUENCE: 3

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
                20                  25                  30

Val Ile Glu Pro Ser Ser Gly Phe Thr Ser Thr Asn Gly Val Pro
            35                  40                  45

Ala Thr Gly His Val Ala Glu Asn Arg Asp Gln Asp Arg Val Gly Ala
        50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Ile Ala Val Asn Ser Arg Leu Ile Ile
130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
                165                 170                 175

Leu Pro Ile Phe Pro Leu Ala Ala Phe Ile Val Glu Lys Leu Val Gln
            180                 185                 190

Arg Asn His Ile Ser Glu Leu Val Ala Val Leu Leu His Val Ile Val
        195                 200                 205

Ser Thr Ala Ala Val Leu Tyr Pro Val Ile Val Ile Leu Thr Cys Asp
210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
                245                 250                 255

Leu Ala Lys Ser Gly Tyr Lys Gly Asp Ala His Pro Asn Ser Thr Ile
            260                 265                 270

Val Ser Cys Ser Tyr Asp Val Ser Leu Lys Ser Leu Ala Tyr Phe Met
        275                 280                 285

Val Ala Pro Thr Leu Cys Tyr Gln Pro Ser Tyr Pro Arg Ser Ser Cys
290                 295                 300

Ile Arg Lys Gly Trp Val Val Arg Gln Phe Val Lys Leu Ile Val Phe
305                 310                 315                 320

Ile Gly Leu Met Gly Phe Ile Ile Glu Gln Tyr Ile Asn Pro Ile Val
                325                 330                 335

Arg Asn Ser Lys His Pro Leu Lys Gly Asp Phe Leu Tyr Ala Ile Glu
            340                 345                 350

Arg Val Leu Lys Leu Ser Val Pro Asn Leu Tyr Val Trp Leu Cys Met
        355                 360                 365

Phe Tyr Ser Phe Phe His Leu Trp Leu Asn Ile Leu Ala Glu Leu Leu
370                 375                 380

Arg Phe Gly Asp Arg Glu Phe Tyr Lys Asp Trp Trp Asn Ala Lys Thr
385                 390                 395                 400

Val Ala Glu Tyr Trp Lys Met Trp Asn Met Pro Val His Arg Trp Met
                405                 410                 415

```
Val Arg His Leu Tyr Phe Pro Cys Leu Arg Asn Gly Ile Pro Lys Glu
            420                 425                 430

Gly Ala Ile Ile Ile Ala Phe Leu Val Ser Gly Ala Phe His Glu Leu
            435                 440                 445

Cys Ile Ala Val Pro Cys His Val Phe Lys Leu Trp Ala Phe Ile Gly
            450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
                485                 490                 495

Cys Ile Leu Gly Gln Pro Met Cys Val Leu Leu Tyr Tyr His Asp Leu
            500                 505                 510

Ile Asn Leu Lys Glu Lys
            515

<210> SEQ ID NO 4
<211> LENGTH: 518
<212> TYPE: PRT
<213> ORGANISM: Tropaeolum majus

<400> SEQUENCE: 4

Met Ala Val Ala Glu Ser Ser Gln Asn Thr Thr Met Ser Gly His
1               5                   10                  15

Gly Asp Ser Asp Leu Asn Asn Phe Arg Arg Lys Pro Ser Ser Ser
                20                  25                  30

Val Ile Glu Pro Ser Ser Ser Gly Phe Thr Ser Thr Asn Gly Val Pro
            35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Lys Gln Val Gly Glu Thr Asp Ile Arg
            85                  90                  95

Phe Thr Tyr Arg Pro Ser Phe Pro Ala His Arg Arg Val Arg Glu Ser
                100                 105                 110

Pro Leu Ser Ser Asp Ala Ile Phe Lys Gln Ser His Ala Gly Leu Phe
            115                 120                 125

Asn Leu Cys Ile Val Val Leu Ile Ala Val Asn Ser Arg Leu Ile Ile
    130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
                165                 170                 175

Leu Pro Ile Phe Pro Leu Ala Ala Phe Ile Val Glu Lys Leu Val Gln
            180                 185                 190

Arg Asn His Ile Ser Glu Leu Val Ala Val Leu Leu His Val Ile Val
            195                 200                 205

Ser Thr Ala Ala Val Leu Tyr Pro Val Ile Val Ile Leu Thr Cys Asp
    210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
                245                 250                 255

Leu Ala Lys Ser Gly Tyr Lys Gly Asp Ala His Pro Asn Ser Thr Ile
            260                 265                 270
```

```
Val Ser Cys Ser Tyr Asp Val Ser Leu Lys Ser Leu Ala Tyr Phe Met
        275                 280                 285

Val Ala Pro Thr Leu Cys Tyr Gln Pro Ser Tyr Pro Arg Ser Ser Cys
        290                 295                 300

Ile Arg Lys Gly Trp Val Val Arg Gln Phe Val Lys Leu Ile Val Phe
305                 310                 315                 320

Ile Gly Leu Met Gly Phe Ile Ile Glu Gln Tyr Ile Asn Pro Ile Val
                325                 330                 335

Arg Asn Ser Lys His Pro Leu Lys Gly Asp Phe Leu Tyr Ala Ile Glu
                340                 345                 350

Arg Val Leu Lys Leu Ser Val Pro Asn Leu Tyr Val Trp Leu Cys Met
                355                 360                 365

Phe Tyr Ser Phe Phe His Leu Trp Leu Asn Ile Leu Ala Glu Leu Leu
        370                 375                 380

Arg Phe Gly Asp Arg Glu Phe Tyr Lys Asp Trp Trp Asn Ala Lys Thr
385                 390                 395                 400

Val Ala Glu Tyr Trp Lys Met Trp Asn Met Pro Val His Arg Trp Met
                405                 410                 415

Val Arg His Leu Tyr Phe Pro Cys Leu Arg Asn Gly Ile Pro Lys Glu
                420                 425                 430

Gly Ala Ile Ile Ile Ala Arg Leu Val Ser Gly Ala Phe His Glu Leu
                435                 440                 445

Cys Ile Ala Val Pro Cys His Val Phe Lys Leu Trp Ala Phe Ile Gly
        450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
                485                 490                 495

Cys Ile Leu Gly Gln Pro Met Cys Val Leu Leu Tyr Tyr His Asp Leu
        500                 505                 510

Ile Asn Leu Lys Glu Lys
        515

<210> SEQ ID NO 5
<211> LENGTH: 518
<212> TYPE: PRT
<213> ORGANISM: Tropaeolum majus

<400> SEQUENCE: 5

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
                20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
                100                 105                 110

Pro Leu Ser Ser Asp Ala Ile Phe Lys Gln Ser His Ala Gly Leu Phe
        115                 120                 125
```

```
Asn Leu Cys Ile Val Val Leu Ile Ala Val Asn Ser Arg Leu Ile Ile
            130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
                165                 170                 175

Leu Pro Ile Phe Pro Leu Ala Ala Phe Ile Val Glu Lys Leu Val Gln
                180                 185                 190

Arg Asn His Ile Ser Glu Leu Ala Val Leu Leu His Val Ile Val
                195                 200                 205

Ser Thr Ala Ala Val Leu Tyr Arg Val Ile Val Ile Leu Thr Cys Asp
210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
                245                 250                 255

Leu Ala Lys Ser Gly Tyr Lys Gly Asp Ala His Pro Asn Ser Thr Ile
                260                 265                 270

Val Ser Cys Ser Tyr Asp Val Ser Leu Lys Ser Leu Ala Tyr Phe Met
                275                 280                 285

Val Ala Pro Thr Leu Cys Tyr Gln Pro Ser Tyr Pro Arg Ser Ser Cys
290                 295                 300

Ile Arg Lys Gly Trp Val Val Arg Gln Phe Val Lys Leu Ile Val Phe
305                 310                 315                 320

Ile Gly Leu Met Gly Phe Ile Ile Glu Gln Tyr Ile Asn Pro Ile Val
                325                 330                 335

Arg Asn Ser Lys His Pro Leu Lys Gly Asp Phe Leu Tyr Ala Ile Glu
                340                 345                 350

Arg Val Leu Lys Leu Ser Val Pro Asn Leu Tyr Val Trp Leu Cys Met
                355                 360                 365

Phe Tyr Ser Phe Phe His Leu Trp Leu Asn Ile Leu Ala Glu Leu Leu
                370                 375                 380

Arg Phe Gly Asp Arg Glu Phe Tyr Lys Asp Trp Asn Ala Lys Thr
385                 390                 395                 400

Val Ala Glu Tyr Trp Lys Met Trp Asn Met Pro Val His Arg Trp Met
                405                 410                 415

Val Arg His Leu Tyr Phe Pro Cys Leu Arg Asn Gly Ile Pro Lys Glu
                420                 425                 430

Gly Ala Ile Ile Ile Ala Phe Leu Val Ser Gly Ala Phe His Glu Leu
                435                 440                 445

Cys Ile Ala Val Pro Cys His Val Phe Lys Leu Trp Ala Phe Ile Gly
                450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
                485                 490                 495

Cys Ile Leu Gly Gln Pro Met Cys Val Leu Leu Tyr Tyr His Asp Leu
                500                 505                 510

Ile Asn Leu Lys Glu Lys
                515

<210> SEQ ID NO 6
<211> LENGTH: 518
<212> TYPE: PRT
<213> ORGANISM: Tropaeolum majus
```

<400> SEQUENCE: 6

```
Met Ala Val Ala Glu Ser Ser Gln Asn Thr Thr Met Ser Gly His
1               5                   10                  15

Gly Asp Ser Asp Leu Asn Asn Phe Arg Arg Lys Pro Ser Ser Ser
            20                  25                  30

Val Ile Glu Pro Ser Ser Gly Phe Thr Thr Asn Gly Val Pro
            35                  40                  45

Ala Thr Gly His Val Ala Glu Asn Arg Asp Gln Asp Arg Val Gly Ala
50                  55                  60

Met Glu Asn Ala Thr Gly Ser Val Asn Leu Ile Gly Asn Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
            115                 120                 125

Asn Leu Cys Ile Val Val Leu Ile Ala Val Asn Ser Arg Leu Ile Ile
130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
            165                 170                 175

Leu Pro Ile Phe Pro Leu Ala Ala Phe Ile Val Glu Lys Leu Val Gln
            180                 185                 190

Arg Asn His Ile Ala Glu Leu Val Ala Val Leu Leu His Val Ile Val
            195                 200                 205

Ser Thr Ala Ala Val Leu Tyr Pro Val Ile Val Ile Leu Thr Cys Asp
210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
            245                 250                 255

Leu Ala Lys Ser Gly Tyr Lys Gly Asp Ala His Pro Asn Ser Thr Ile
            260                 265                 270

Val Ser Cys Ser Tyr Asp Val Ser Leu Lys Ser Leu Ala Tyr Phe Met
            275                 280                 285

Val Ala Pro Thr Leu Cys Tyr Gln Pro Ser Tyr Pro Arg Ser Ser Cys
            290                 295                 300

Ile Arg Lys Gly Trp Val Val Arg Gln Phe Val Lys Leu Ile Val Phe
305                 310                 315                 320

Ile Gly Leu Met Gly Phe Ile Ile Glu Gln Tyr Ile Asn Pro Ile Val
            325                 330                 335

Arg Asn Ser Lys His Pro Leu Lys Gly Asp Phe Leu Tyr Ala Ile Glu
            340                 345                 350

Arg Val Leu Lys Leu Ser Val Pro Asn Leu Tyr Val Trp Leu Cys Met
            355                 360                 365

Phe Tyr Ser Phe Phe His Leu Trp Leu Asn Ile Leu Ala Glu Leu Leu
            370                 375                 380

Arg Phe Gly Asp Arg Glu Phe Tyr Lys Asp Trp Trp Asn Ala Lys Thr
385                 390                 395                 400

Val Ala Glu Tyr Trp Lys Met Trp Asn Met Pro Val His Arg Trp Met
            405                 410                 415
```

```
Val Arg His Leu Tyr Phe Pro Cys Leu Arg Asn Gly Ile Pro Lys Glu
            420                 425                 430

Gly Ala Ile Ile Ile Ala Phe Leu Val Ser Gly Ala Phe His Glu Leu
        435                 440                 445

Cys Ile Ala Val Pro Cys His Val Phe Lys Leu Trp Ala Phe Ile Gly
        450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
                485                 490                 495

Cys Ile Leu Gly Gln Pro Met Cys Val Leu Leu Tyr Tyr His Asp Leu
            500                 505                 510

Ile Asn Leu Lys Glu Lys
            515

<210> SEQ ID NO 7
<211> LENGTH: 518
<212> TYPE: PRT
<213> ORGANISM: Tropaeolum majus

<400> SEQUENCE: 7

Met Ala Val Ala Glu Ser Ser Gln Asn Thr Thr Thr Met Ser Gly His
1               5                   10                  15

Gly Asp Ser Asp Leu Asn Asn Phe Arg Arg Lys Pro Ser Ser Ser
            20                  25                  30

Val Ile Glu Pro Ser Ser Gly Phe Thr Ser Thr Asn Gly Val Pro
            35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Ile Ala Val Asn Ser Arg Leu Ile Ile
    130                 135                 140

Val Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
                165                 170                 175

Leu Pro Ile Phe Pro Leu Ala Ala Phe Ile Val Glu Lys Leu Val Gln
            180                 185                 190

Arg Asn His Ile Ser Glu Leu Val Ala Val Leu Leu His Val Ile Val
        195                 200                 205

Ser Thr Ala Ala Val Leu Tyr Pro Val Ile Val Leu Thr Cys Asp
    210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
                245                 250                 255

Leu Ala Lys Ser Gly Tyr Lys Gly Asp Ala His Pro Asn Ser Thr Ile
            260                 265                 270
```

```
Val Ser Cys Ser Tyr Asp Val Ser Leu Lys Ser Leu Ala Tyr Phe Met
        275                 280                 285

Val Ala Pro Thr Leu Cys Tyr Gln Pro Ser Tyr Pro Arg Ser Ser Cys
        290                 295                 300

Ile Arg Lys Gly Trp Val Arg Gln Phe Lys Leu Ile Val Phe
305                 310                 315                 320

Ile Gly Leu Met Gly Phe Ile Ile Glu Gln Tyr Ile Asn Pro Ile Val
                    325                 330                 335

Arg Asn Ser Lys His Pro Leu Lys Gly Asp Phe Leu Tyr Ala Ile Glu
                340                 345                 350

Arg Val Leu Lys Leu Ser Val Pro Asn Leu Tyr Val Trp Leu Cys Met
            355                 360                 365

Phe Tyr Ser Phe Phe His Leu Trp Leu Asn Ile Leu Ala Glu Leu Leu
        370                 375                 380

Arg Phe Gly Asp Arg Glu Phe Tyr Lys Asp Trp Trp Asn Ala Lys Thr
385                 390                 395                 400

Val Ala Glu Tyr Trp Lys Met Trp Asn Met Pro Val His Arg Trp Met
                    405                 410                 415

Val Arg His Leu Tyr Phe Pro Cys Leu Arg Asn Gly Ile Pro Lys Glu
                420                 425                 430

Gly Ala Ile Ile Ile Ala Phe Leu Val Ser Gly Ala Phe His Glu Leu
            435                 440                 445

Cys Ile Ala Val Pro Cys His Val Phe Lys Leu Trp Ala Phe Ile Gly
        450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
                    485                 490                 495

Cys Ile Leu Gly Gln Pro Met Cys Val Leu Tyr Tyr His Asp Leu
                500                 505                 510

Ile Asn Leu Lys Glu Lys
            515

<210> SEQ ID NO 8
<211> LENGTH: 518
<212> TYPE: PRT
<213> ORGANISM: Tropaeolum majus

<400> SEQUENCE: 8

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
                20                  25                  30

Val Ile Glu Pro Ser Ser Ser Gly Phe Thr Thr Asn Gly Val Pro
            35                  40                  45

Ala Thr Gly His Val Ala Glu Asn Arg Asp Gln Asp Arg Val Gly Ala
        50                  55                  60

Met Glu Asn Ala Thr Gly Ser Val Asn Leu Ile Gly Asn Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
                100                 105                 110

Pro Leu Ser Ser Asp Ala Ile Phe Lys Gln Ser His Ala Gly Leu Phe
            115                 120                 125
```

```
Asn Leu Cys Ile Val Val Leu Ile Ala Val Asn Ser Arg Leu Ile Ile
    130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
                165                 170                 175

Leu Pro Ile Phe Pro Leu Ala Ala Phe Ile Val Glu Lys Leu Val Gln
                180                 185                 190

Arg Asn His Ile Ser Glu Leu Val Ala Val Leu Leu His Val Ile Val
                195                 200                 205

Ser Thr Ala Ala Val Leu Tyr Pro Val Ile Val Ile Leu Thr Cys Asp
    210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
                245                 250                 255

Leu Ala Lys Ser Gly Tyr Lys Gly Asp Ala His Pro Asn Ser Thr Ile
                260                 265                 270

Val Ser Cys Ser Tyr Asp Val Ser Leu Lys Ser Leu Ala Tyr Phe Met
                275                 280                 285

Val Ala Pro Thr Leu Cys Tyr Gln Pro Ser Tyr Pro Arg Ser Ser Cys
                290                 295                 300

Ile Arg Lys Gly Trp Val Val Arg Gln Phe Val Lys Leu Ile Val Phe
305                 310                 315                 320

Ile Gly Leu Met Gly Phe Ile Ile Glu Gln Tyr Ile Asn Pro Ile Val
                325                 330                 335

Arg Asn Ser Lys His Pro Leu Lys Gly Asp Phe Leu Tyr Ala Ile Glu
                340                 345                 350

Arg Val Leu Lys Leu Ser Val Pro Asn Leu Tyr Val Trp Leu Cys Met
                355                 360                 365

Phe Tyr Ser Phe Phe His Leu Trp Leu Asn Ile Leu Ala Glu Leu Leu
    370                 375                 380

Arg Phe Gly Asp Arg Glu Phe Ala Lys Asp Trp Trp Asn Ala Lys Thr
385                 390                 395                 400

Val Ala Glu Tyr Trp Lys Met Trp Asn Met Pro Val His Arg Trp Met
                405                 410                 415

Val Arg His Leu Tyr Phe Pro Cys Leu Arg Asn Gly Ile Pro Lys Glu
                420                 425                 430

Gly Ala Ile Ile Ile Ala Phe Leu Val Ser Gly Ala Phe His Glu Leu
                435                 440                 445

Cys Ile Ala Val Pro Cys His Val Phe Lys Leu Trp Ala Phe Ile Gly
    450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
                485                 490                 495

Cys Ile Leu Gly Gln Pro Met Cys Val Leu Leu Tyr Tyr His Asp Leu
                500                 505                 510

Ile Asn Leu Lys Glu Lys
                515

<210> SEQ ID NO 9
<211> LENGTH: 518
<212> TYPE: PRT
```

-continued

<213> ORGANISM: Tropaeolum majus

<400> SEQUENCE: 9

Met Ala Val Ala Glu Ser Ser Gln Asn Thr Thr Met Ser Gly His
1               5                   10                  15

Gly Asp Ser Asp Leu Asn Asn Phe Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Ile Ala Val Asn Ser Arg Leu Ile Ile
130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
                165                 170                 175

Leu Pro Ile Phe Pro Leu Ala Ala Phe Ile Val Glu Lys Leu Val Gln
            180                 185                 190

Arg Asn His Ile Ser Glu Leu Val Ala Val Leu Leu His Val Ile Val
        195                 200                 205

Ser Thr Ala Ala Val Leu Tyr Pro Val Ile Val Leu Thr Cys Asp
210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
                245                 250                 255

Leu Ala Lys Ser Gly Tyr Lys Gly Asp Ala His Pro Asn Ser Thr Ile
            260                 265                 270

Val Ser Cys Ser Tyr Asp Val Ser Leu Lys Ser Leu Ala Tyr Phe Met
        275                 280                 285

Val Ala Pro Thr Leu Cys Tyr Gln Pro Ser Tyr Pro Arg Ser Ser Cys
290                 295                 300

Ile Arg Lys Gly Trp Val Val Arg Gln Phe Val Lys Leu Ile Val Phe
305                 310                 315                 320

Ile Gly Leu Met Gly Phe Ile Ile Glu Gln Tyr Ile Asn Pro Ile Val
                325                 330                 335

Arg Asn Ser Lys His Pro Leu Lys Gly Asp Phe Leu Tyr Ala Ile Glu
            340                 345                 350

Arg Val Leu Lys Leu Ser Val Pro Asn Leu Tyr Val Trp Leu Cys Met
        355                 360                 365

Phe Tyr Ser Phe Phe His Leu Trp Leu Asn Ile Leu Ala Glu Leu Leu
370                 375                 380

Arg Phe Gly Asp Arg Glu Phe Gly Lys Asp Gly Trp Asn Ala Lys Thr
385                 390                 395                 400

Val Ala Glu Tyr Trp Lys Met Trp Asn Met Pro Val His Arg Trp Met

```
                        405                 410                 415
Val Arg His Leu Tyr Phe Pro Cys Leu Arg Asn Gly Ile Pro Lys Glu
                420                 425                 430

Gly Ala Ile Ile Ile Ala Phe Leu Val Ser Gly Ala Phe His Glu Leu
            435                 440                 445

Cys Ile Ala Val Pro Cys His Val Phe Lys Leu Trp Ala Phe Ile Gly
        450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Ile Phe
                485                 490                 495

Cys Ile Leu Gly Gln Pro Met Cys Val Leu Leu Tyr Tyr His Asp Leu
            500                 505                 510

Ile Asn Leu Lys Glu Lys
        515

<210> SEQ ID NO 10
<211> LENGTH: 1557
<212> TYPE: DNA
<213> ORGANISM: Tropaeolum majus

<400> SEQUENCE: 10
atggcggtgg cagagtcgtc acagaacacg acaaccatga gtggtcacgg cgactcggat      60
ctcaacaatt tccgtagaag gaaaccgagt tcctccgtga ttgaaccttc gtcgtccggt     120
tttacatcca ccaatggcgt accggcgact ggccacgtgg ctgagaatcg tgaccaggat     180
cgggtagggg ctatggagaa cgcaacagga tcggtcaact taattggaaa tggtggaggc     240
gtggttatcg gaatgaaga gaaacaggta ggggagactg atatacgatt cacttaccgg     300
ccttcgtttc cggctcatcg gagggtgagg gagagtcctc ttagctctga tgcaatcttc     360
aaacagagcc atgcgggttt attcaacttg tgtatagtag tgctcattgc agtaaacagt     420
aggcttatca tcgaaaatct tatgaagtat ggttggttga tcgatactgg tttctggttt     480
agctcaagat cactgggtga ttggtccatc tttatgtgct gtcttacact cccaattttc     540
ccacttgctg cttttattgt tgaaaagctg gtgcagcgaa atcatatatc tgaacttgtt     600
gctgttctcc ttcatgtaat cgtttctacc gctgcagttt tatatccagt tattgtgatc     660
ttaacgtgtg attcggtgta tatgtctggt gtggtattga tgctcttgg ttgcattatg     720 tggttgaagc tggtgtcata tgcacatact agttctgata ttagaacact ggccaaatct     780
ggctataagg gggatgcgca ccccaattca accattgtga gttgctcata tgatgttagc     840
ttgaagagtt tggcatactt catggttgct ccgacattat gttaccagcc tagctatcct     900
cgttcgtcgt gtatccgcaa gggttgggtt gttcgtcaat tgtcaaact aatagttttc     960 ataggactca tggggttcat tatagaacaa tatattaatc ctatcgttcg aaattccaaa    1020
cacccattga aaggagattt tttatatgca atagaaagag ttttgaagct ttcagttcca    1080
aatctatatg tttggctttg catgttctac tctttttcc acctctggtt gaacatactg    1140
gctgagcttc ttcgctttgg tgatcgtgaa ttctacaaag attggtggaa tgcaaaaact    1200
gttgcggagt attggaaaat gtggaatatg cctgttcata gatggatggt tcgtcatcta    1260
tattttccct gtttgaggaa tgggataccc aaggaaggtg ccattattat cgcgcgctta    1320
gtttctggtg cttttccatga gctctgcatt gcagttcctt gccacgtatt caagttatgg    1380
gcctttatag gcattatgtt tcaggttccc ttggtattga ttacgaatta tctacaagaa    1440
aagttcagta attctatggt gggcaatatg atcttctggt tcatcttctg catacttggc    1500
```

```
caacctatgt gtgtccttct atattaccat gacctgataa atctaaagga aaagtga      1557
```

<210> SEQ ID NO 11
<211> LENGTH: 1557
<212> TYPE: DNA
<213> ORGANISM: Tropaeolum majus

<400> SEQUENCE: 11

```
atggcggtgg cagagtcgtc acagaacacg acaaccatga gtggtcacgg cgactcggat     60
ctcaacaatt ccgtagaaag gaaaccgagt tcctccgtga ttgaaccttc gtcgtccggt    120
tttacatcca ccaatggcgt accggcgact ggccacgtgg ctgagaatcg tgaccaggat    180
cgggtagggg ctatggagaa cgcaacagga tcggtcaact taattggaaa tggtggaggc    240
gtggttatcg ggaatgaaga gaaacaggta ggggagactg atatacgatt cacttaccgg    300
ccttcgtttc cggctcatcg gagggtgagg gagagtcctc ttagctctga tgcaatcttc    360
aaacagagcc atgcgggttt attcaacttg tgtatagtag tgctcattgc agtaaacagt    420
aggcttatca tcgaaaatct tatgaagtat ggttggttga tcgatactgg tttctggttt    480
agctcaagat cactgggtga ttggtccatc tttatgtgct gtcttacact cccaattttc    540
ccacttgctg ctttattgt tgaaaagctg gtgcagcgaa atcatatatc tgaacttgtt    600
gctgttctcc ttcatgtaat cgtttctacc gctgcagttt tatatcgagt tatttgtgatc    660
ttaacgtgtg attcggtgta tatgtctggt gtggtattga tgctctttgg ttgcattatg    720
tggttgaagc tggtgtcata tgcacatact agttctgata ttagaacact ggccaaatct    780
ggctataagg gggatgcgca ccccaattca accattgtga gttgctcata tgatgttagc    840
ttgaagagtt tggcatactt catggttgct ccgacattat gttaccagcc tagctatcct    900
cgttcgtcgt gtatccgcaa gggttgggtt gttcgtcaat ttgtcaaact aatagttttc    960
ataggactca tggggttcat tatagaacaa tatattaatc ctatcgttcg aaattccaaa   1020
cacccattga aaggagattt tttatatgca atagaaagag ttttgaagct ttcagttcca   1080
aatctatatg tttggctttg catgttctac tctttttttcc acctctggtt gaacatactg   1140
gctgagcttc ttcgctttgg tgatcgtgaa ttctacaaag attggtggaa tgcaaaaact   1200
gttgcggagt attggaaaat gtggaatatg cctgttcata gatggatggt tcgtcatcta   1260
tattttccct gtttgaggaa tgggatacccc aaggaaggtg ccattattat cgcgttctta   1320
gtttctggtg ctttccatga gctctgcatt gcagttcctt gccacgtatt caagttatgg   1380
gcctttatag gcattatgtt tcaggttccc ttggtattga ttacgaatta tctacaagaa   1440
aagttcagta attctatggt gggcaatatg atcttctggt tcatcttctg catacttggc   1500
caacctatgt gtgtccttct atattaccat gacctgataa atctaaagga aaagtga      1557
```

<210> SEQ ID NO 12
<211> LENGTH: 1557
<212> TYPE: DNA
<213> ORGANISM: Tropaeolum majus

<400> SEQUENCE: 12

```
atggcggtgg cagagtcgtc acagaacacg acaaccatga gtggtcacgg cgactcggat     60
ctcaacaatt ccgtagaaag gaaaccgagt tcctccgtga ttgaaccttc gtcgtccggt    120
tttacatcca ccaatggcgt accggcgact ggccacgtgg ctgagaatcg tgaccaggat    180
cgggtagggg ctatggagaa cgcaacagga tcggtcaact taattggaaa tggtggaggc    240
gtggttatcg ggaatgaaga gaaacaggta ggggagactg atatacgatt cacttaccgg    300
```

```
ccttcgtttc cggctcatcg gagggtgagg gagagtcctc ttagctctga tgcaatcttc      360
aaacagagcc atgcgggttt attcaacttg tgtatagtag tgctcattgc agtaaacagt      420
aggcttatca tcgaaaatct tatgaagtat ggttggttga tcgatactgg tttctggttt      480
agctcaagat cactgggtga ttggtccatc tttatgtgct gtcttacact cccaattttc      540
ccacttgctg cttttattgt tgaaaagctg gtgcagcgaa atcatatagc tgaacttgtt      600
gctgttctcc ttcatgtaat cgtttctacc gctgcagttt tatatccagt tattgtgatc      660
ttaacgtgtg attcggtgta tatgtctggt gtggtattga tgctctttgg ttgcattatg      720
tggttgaagc tggtgtcata tgcacatact agttctgata ttagaacact ggccaaatct      780
ggctataagg gggatgcgca ccccaattca accattgtga gttgctcata tgatgttagc      840
ttgaagagtt tggcatactt catggttgct ccgacattat gttaccagcc tagctatcct      900
cgttcgtcgt gtatccgcaa gggttgggtt gttcgtcaat tgtcaaaact aatagttttc      960
ataggactca tggggttcat tatagaacaa tatattaatc ctatcgttcg aaattccaaa     1020
cacccattga aggagatttt tttatatgca atagaaagag ttttgaagct ttcagttcca     1080
aatctatatg tttggctttg catgttctac tcttttttcc acctctggtt gaacatactg     1140
gctgagcttc ttcgctttgg tgatcgtgaa ttctacaaag attggtggaa tgcaaaaact     1200
gttgcggagt attggaaaat gtggaatatg cctgttcata gatggatggt tcgtcatcta     1260
tattttccct gtttgaggaa tgggataccc aaggaaggtg ccattattat cgcgttctta     1320
gtttctggtg ctttccatga gctctgcatt gcagttcctt gccacgtatt caagttatgg     1380
gcctttatag gcattatgtt tcaggttccc ttggtattga ttacgaatta tctacaagaa     1440
aagttcagta attctatggt gggcaatatg atcttctggt tcatcttctg catacttggc     1500
caacctatgt gtgtccttct atattaccat gacctgataa atctaaagga aaagtga       1557

<210> SEQ ID NO 13
<211> LENGTH: 1557
<212> TYPE: DNA
<213> ORGANISM: Tropaeolum majus

<400> SEQUENCE: 13
atggcggtgg cagagtcgtc acagaacacg acaaccatga gtggtcacgg cgactcggat       60
ctcaacaatt tccgtagaag gaaaccgagt tcctccgtga ttgaaccttc gtcgtccggt      120
tttacatcca ccaatggcgt accggcgact ggccacgtgg ctgagaatcg tgaccaggat      180
cgggtagggg ctatggagaa cgcaacagga tcggtcaact taattggaaa tggtggaggc      240
gtggttatcg ggaatgaaga gaaacaggta ggggagactg atatacgatt cacttaccgg      300
ccttcgtttc cggctcatcg gagggtgagg gagagtcctc ttagctctga tgcaatcttc      360
aaacagagcc atgcgggttt attcaacttg tgtatagtag tgctcattgc agtaaacagt      420
aggcttatca tcgtaaatct tatgaagtat ggttggttga tcgatactgg tttctggttt      480
agctcaagat cactgggtga ttggtccatc tttatgtgct gtcttacact cccaattttc      540
ccacttgctg cttttattgt tgaaaagctg gtgcagcgaa atcatatatc tgaacttgtt      600
gctgttctcc ttcatgtaat cgtttctacc gctgcagttt tatatccagt tattgtgatc      660
ttaacgtgtg attcggtgta tatgtctggt gtggtattga tgctctttgg ttgcattatg      720
tggttgaagc tggtgtcata tgcacatact agttctgata ttagaacact ggccaaatct      780
ggctataagg gggatgcgca ccccaattca accattgtga gttgctcata tgatgttagc      840
ttgaagagtt tggcatactt catggttgct ccgacattat gttaccagcc tagctatcct      900
```

```
cgttcgtcgt gtatccgcaa gggttgggtt gttcgtcaat tgtcaaact aatagttttc      960 ataggactca tggggttcat tatagaacaa tatattaatc ctatcgttcg aaattccaaa     1020
cacccattga aaggagattt tttatatgca atagaaagag ttttgaagct ttcagttcca     1080
aatctatatg tttggctttg catgttctac tcttttttcc acctctggtt gaacatactg     1140
gctgagcttc ttcgctttgg tgatcgtgaa ttctacaaag attggtggaa tgcaaaaact     1200
gttgcggagt attggaaaat gtggaatatg cctgttcata gatggatggt tcgtcatcta     1260
tattttccct gtttgaggaa tgggataccc aaggaaggtg ccattattat cgcgttctta     1320
gtttctggtg ctttccatga gctctgcatt gcagttcctt gccacgtatt caagttatgg     1380
gcctttatag gcattatgtt tcaggttccc ttggtattga ttacgaatta tctacaagaa     1440
aagttcagta attctatggt gggcaatatg atcttctggt tcatcttctg catacttggc     1500
caacctatgt gtgtccttct atattaccat gacctgataa atctaaagga aaagtga       1557

<210> SEQ ID NO 14
<211> LENGTH: 1557
<212> TYPE: DNA
<213> ORGANISM: Tropaeolum majus

<400> SEQUENCE: 14
atggcggtgg cagagtcgtc acagaacacg acaaccatga gtggtcacgg cgactcggat       60
ctcaacaatt tccgtagaag gaaaccgagt tcctccgtga ttgaaccttc gtcgtccggt      120
tttacatcca ccaatggcgt accggcgact ggccacgtgg ctgagaatcg tgaccaggat      180
cgggtagggg ctatggagaa cgcaacagga tcggtcaact taattggaaa tggtggaggc      240
gtggttatcg ggaatgaaga gaaacaggta ggggagactg atatacgatt cacttaccgg      300
ccttcgtttc cggctcatcg gagggtgagg gagagtcctc ttagctctga tgcaatcttc      360
aaacagagcc atgcgggttt attcaacttg tgtatagtag tgctcattgc agtaaacagt      420
aggcttatca tcgaaaatct tatgaagtat ggttggttga tcgatactgg tttctggttt      480
agctcaagat cactgggtga ttggtccatc tttatgtgct gtcttacact cccaattttc      540
ccacttgctg ctttttattgt tgaaaagctg gtgcagcgaa atcatatatc tgaacttgtt      600
gctgttctcc ttcatgtaat cgtttctacc gctgcagttt tatatccagt tattgtgatc      660
ttaacgtgtg attcggtgta tatgtctggt gtggtattga tgctctttgg ttgcattatg      720
tggttgaagc tggtgtcata tgcacatact agttctgata ttagaacact ggccaaatct      780
ggctataagg gggatgcgca ccccaattca accattgtga gttgctcata tgatgttagc      840
ttgaagagtt tggcatactt catggttgct ccgacattat gttaccagcc tagctatcct      900
cgttcgtcgt gtatccgcaa gggttgggtt gttcgtcaat tgtcaaact aatagttttc      960 ataggactca tggggttcat tatagaacaa tatattaatc ctatcgttcg aaattccaaa     1020
cacccattga aaggagattt tttatatgca atagaaagag ttttgaagct ttcagttcca     1080
aatctatatg tttggctttg catgttctac tcttttttcc acctctggtt gaacatactg     1140
gctgagcttc ttcgctttgg tgatcgtgaa ttcgccaaag attggtggaa tgcaaaaact     1200
gttgcggagt attggaaaat gtggaatatg cctgttcata gatggatggt tcgtcatcta     1260
tattttccct gtttgaggaa tgggataccc aaggaaggtg ccattattat cgcgttctta     1320
gtttctggtg ctttccatga gctctgcatt gcagttcctt gccacgtatt caagttatgg     1380
gcctttatag gcattatgtt tcaggttccc ttggtattga ttacgaatta tctacaagaa     1440
aagttcagta attctatggt gggcaatatg atcttctggt tcatcttctg catacttggc     1500
```

```
caacctatgt gtgtccttct atattaccat gacctgataa atctaaagga aaagtga      1557
```

<210> SEQ ID NO 15
<211> LENGTH: 1557
<212> TYPE: DNA
<213> ORGANISM: Tropaeolum majus

<400> SEQUENCE: 15

```
atggcggtgg cagagtcgtc acagaacacg acaaccatga gtggtcacgg cgactcggat       60
ctcaacaatt tccgtagaag gaaaccgagt tcctccgtga ttgaaccttc gtcgtccggt      120
tttacatcca ccaatggcgt accggcgact ggccacgtgg ctgagaatcg tgaccaggat      180
cgggtagggg ctatggagaa cgcaacagga tcggtcaact taattggaaa tggtggaggc      240
gtggttatcg ggaatgaaga gaaacaggta ggggagactg atatacgatt cacttaccgg      300
ccttcgtttc cggctcatcg gagggtgagg gagagtcctc ttagctctga tgcaatcttc      360
aaacagagcc atgcgggttt attcaacttg tgtatagtag tgctcattgc agtaaacagt      420
aggcttatca tcgaaaatct tatgaagtat ggttggttga tcgatactgg tttctggttt      480
agctcaagat cactgggtga ttggtccatc tttatgtgct gtcttacact cccaattttc      540
ccacttgctg ctttattgt tgaaaagctg gtgcagcgaa atcatatatc tgaacttgtt      600
gctgttctcc ttcatgtaat cgtttctacc gctgcagttt tatatccagt tattgtgatc      660
ttaacgtgtg attcggtgta tatgtctggt gtggtattga tgctcttgg ttgcattatg      720
tggttgaagc tggtgtcata tgcacatact agttctgata ttagaacact ggccaaatct      780
ggctataagg gggatgcgca ccccaattca accattgtga gttgctcata tgatgttagc      840
ttgaagagtt tggcatactt catggttgct ccgacattat gttaccagcc tagctatcct      900
cgttcgtcgt gtatccgcaa gggttgggtt gttcgtcaat ttgtcaaact aatagttttc      960
ataggactca tggggttcat tatagaacaa tatattaatc ctatcgttcg aaattccaaa     1020
cacccattga aaggagattt tttatatgca atagaaagag ttttgaagct ttcagttcca     1080
aatctatatg tttggctttg catgttctac tcttttttcc acctctggtt gaacatactg     1140
gctgagcttc ttcgctttgg tgatcgtgaa ttcggcaaag atgggtggaa tgcaaaaact     1200
gttgcggagt attggaaaat gtggaatatg cctgttcata gatggatggt tcgtcatcta     1260
tattttccct gtttgaggaa tgggataccc aaggaaggtg ccattattat cgcgttctta     1320
gtttctggtg cttttccatga gctctgcatt gcagttcctt gccacgtatt caagttatgg     1380
gcctttatag gcattatgtt tcaggttccc ttggtattga ttacgaatta tctacaagaa     1440
aagttcagta attctatggt gggcaatatg atcttctggt tcatcttctg catacttggc     1500
caacctatgt gtgtccttct atattaccat gacctgataa atctaaagga aaagtga       1557
```

<210> SEQ ID NO 16
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (12)..(12)
<223> OTHER INFORMATION: n is i
<220> FEATURE:
<221> NAME/KEY: misc_feature
<222> LOCATION: (15)..(15)
<223> OTHER INFORMATION: n is i
<220> FEATURE:
<221> NAME/KEY: misc_feature

```
<222> LOCATION: (18)..(18)
<223> OTHER INFORMATION: n is i

<400> SEQUENCE: 16
tayttyatgg tngcnccnac                                            20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
ggcatrttcc acatyckcca                                            20

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
gaaatggcgg tggcagag                                              18

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
tcacttttcc tttagattta tc                                         22

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
tatctagaat ggcggtggca gag                                        23

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
atggtacctc acttttcctt tagatttatc                                 30

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
tttcttcgcc acttgtcact cc                                         22
```

```
<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
cgcgctatat tttgttttct a                                      21

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
gaggtaccgg aaatggcggt ggcag                                  25

<210> SEQ ID NO 25
<211> LENGTH: 36
<212> TYPE: DNA
<213> ORGANISM: Artificial Sequence
<220> FEATURE:
<223> OTHER INFORMATION: Primer

<400> SEQUENCE: 25
ccgctcgagt ttcactttc ctttagattt atcagg                       36

<210> SEQ ID NO 26
<211> LENGTH: 35
<212> TYPE: DNA
<213> ORGANISM: Artificial Sequence
<220> FEATURE:
<223> OTHER INFORMATION: Primer

<400> SEQUENCE: 26
ggtgccatta ttatcgcgcg cttagtttct ggtgc                       35

<210> SEQ ID NO 27
<211> LENGTH: 35
<212> TYPE: DNA
<213> ORGANISM: Artificial Sequence
<220> FEATURE:
<223> OTHER INFORMATION: Primer

<400> SEQUENCE: 27
gcaccagaaa ctaagcgcgc gataataatg gcacc                       35

<210> SEQ ID NO 28
<211> LENGTH: 38
<212> TYPE: DNA
<213> ORGANISM: Artificial Sequence
<220> FEATURE:
<223> OTHER INFORMATION: Primer

<400> SEQUENCE: 28
ccgctgcagt tttatatcga gttattgtga tcttaacg                    38

<210> SEQ ID NO 29
<211> LENGTH: 38
<212> TYPE: DNA
<213> ORGANISM: Artificial Sequence
<220> FEATURE:
<223> OTHER INFORMATION: Primer

<400> SEQUENCE: 29
```

```
cgttaagatc acaataactc gatataaaac tgcagcgg                              38
```

<210> SEQ ID NO 30
<211> LENGTH: 31
<212> TYPE: DNA
<213> ORGANISM: Artificial Sequence
<220> FEATURE:
<223> OTHER INFORMATION: Primer

<400> SEQUENCE: 30

```
tggtgatcgt gaattcgcca aagattggtg g                                    31
```

<210> SEQ ID NO 31
<211> LENGTH: 31
<212> TYPE: DNA
<213> ORGANISM: Artificial Sequence
<220> FEATURE:
<223> OTHER INFORMATION: Primer

<400> SEQUENCE: 31

```
ccaccaatct ttggcgaatt cacgatcacc a                                    31
```

<210> SEQ ID NO 32
<211> LENGTH: 36
<212> TYPE: DNA
<213> ORGANISM: Artificial Sequence
<220> FEATURE:
<223> OTHER INFORMATION: Primer

<400> SEQUENCE: 32

```
tggtgatcgt gaattcggca aagatgggtg gaatgc                               36
```

<210> SEQ ID NO 33
<211> LENGTH: 36
<212> TYPE: DNA
<213> ORGANISM: Artificial Sequence
<220> FEATURE:
<223> OTHER INFORMATION: Primer

<400> SEQUENCE: 33

```
gcattccacc catctttgcc gaattcacga tcacca                               36
```

<210> SEQ ID NO 34
<211> LENGTH: 35
<212> TYPE: DNA
<213> ORGANISM: Artificial Sequence
<220> FEATURE:
<223> OTHER INFORMATION: Primer

<400> SEQUENCE: 34

```
agtaggctta tcatcgtaaa tcttatgaag tatgg                                35
```

<210> SEQ ID NO 35
<211> LENGTH: 35
<212> TYPE: DNA
<213> ORGANISM: Artificial Sequence
<220> FEATURE:
<223> OTHER INFORMATION: Primer

<400> SEQUENCE: 35

```
ccatacttca taagatttac gatgataagc ctact                                35
```

<210> SEQ ID NO 36
<211> LENGTH: 35
<212> TYPE: DNA
<213> ORGANISM: Artificial Sequence

```
<220> FEATURE:
<223> OTHER INFORMATION: Primer

<400> SEQUENCE: 36
gcgaaatcat atagctgaac ttgttgctgt tctcc                          35

<210> SEQ ID NO 37
<211> LENGTH: 35
<212> TYPE: DNA
<213> ORGANISM: Artificial Sequence
<220> FEATURE:
<223> OTHER INFORMATION: Primer

<400> SEQUENCE: 37
ggagaacagc aacaagttca gctatatgat ttcgc                          35

<210> SEQ ID NO 38
<211> LENGTH: 501
<212> TYPE: PRT
<213> ORGANISM: Brassica napus (BnDGAT)

<400> SEQUENCE: 38
```

Met Glu Ile Leu Asp Ser Gly Gly Val Thr Met Pro Thr Glu Asn Gly
1               5                   10                  15

Gly Ala Asp Leu Asp Thr Leu Arg His Arg Lys Pro Arg Ser Asp Ser
            20                  25                  30

Ser Asn Gly Leu Leu Pro Asp Ser Val Thr Val Ser Asp Ala Asp Val
        35                  40                  45

Arg Asp Arg Val Asp Ser Ala Val Glu Asp Thr Gln Gly Lys Ala Asn
    50                  55                  60

Leu Ala Gly Glu Asn Glu Ile Arg Glu Ser Gly Gly Glu Ala Gly Gly
65                  70                  75                  80

Asn Val Asp Val Arg Tyr Thr Tyr Arg Pro Ser Val Pro Ala His Arg
                85                  90                  95

Arg Val Arg Glu Ser Pro Leu Ser Ser Asp Ala Ile Phe Lys Gln Ser
            100                 105                 110

His Ala Gly Leu Phe Asn Leu Cys Val Val Leu Val Ala Val Asn
        115                 120                 125

Ser Arg Leu Ile Ile Glu Asn Leu Met Lys Tyr Gly Trp Leu Ile Arg
130                 135                 140

Thr Asp Phe Trp Phe Ser Ser Thr Ser Leu Arg Asp Trp Pro Leu Phe
145                 150                 155                 160

Met Cys Cys Leu Ser Leu Ser Ile Phe Pro Leu Ala Ala Phe Thr Val
                165                 170                 175

Glu Lys Leu Val Leu Gln Lys Cys Ile Ser Glu Pro Val Val Ile Ile
            180                 185                 190

Leu His Ile Ile Thr Met Thr Glu Val Leu Tyr Pro Val Tyr Val
        195                 200                 205

Thr Leu Arg Cys Asp Ser Ala Phe Leu Ser Gly Val Thr Leu Met Leu
    210                 215                 220

Leu Thr Cys Ile Val Trp Leu Lys Leu Val Ser Tyr Ala His Thr Asn
225                 230                 235                 240

Tyr Asp Ile Arg Thr Leu Ala Asn Ser Ser Asp Lys Ala Asn Pro Glu
                245                 250                 255

Val Ser Tyr Tyr Val Ser Leu Lys Ser Leu Ala Tyr Phe Met Leu Ala
            260                 265                 270

Pro Thr Leu Cys Tyr Gln Pro Ser Tyr Pro Arg Ser Pro Cys Ile Arg
        275                 280                 285

```
Lys Gly Trp Val Ala Arg Gln Phe Ala Lys Leu Ile Ile Phe Thr Gly
    290                 295                 300
Phe Met Gly Phe Ile Ile Glu Gln Tyr Ile Asn Pro Ile Val Arg Asn
305                 310                 315                 320
Ser Lys His Pro Leu Lys Gly Asp Leu Leu Tyr Gly Val Glu Arg Val
                325                 330                 335
Leu Lys Leu Ser Val Pro Asn Leu Tyr Val Trp Leu Cys Met Phe Tyr
            340                 345                 350
Cys Phe Phe His Leu Trp Leu Asn Ile Leu Ala Glu Leu Leu Cys Phe
        355                 360                 365
Gly Asp Arg Glu Phe Tyr Lys Asp Trp Trp Asn Ala Lys Ser Val Gly
    370                 375                 380
Asp Tyr Trp Arg Met Trp Asn Met Pro Val His Lys Trp Met Val Arg
385                 390                 395                 400
His Val Tyr Phe Pro Cys Leu Arg Arg Asn Ile Pro Lys Val Pro Ala
                405                 410                 415
Ile Ile Leu Ala Phe Leu Val Ser Ala Val Phe His Glu Leu Cys Ile
            420                 425                 430
Ala Val Pro Cys Arg Leu Phe Lys Leu Trp Ala Phe Leu Gly Ile Met
        435                 440                 445
Phe Gln Val Pro Leu Val Phe Ile Thr Asn Tyr Leu Gln Glu Arg Phe
    450                 455                 460
Gly Ser Met Val Gly Asn Met Ile Phe Trp Phe Thr Phe Cys Ile Phe
465                 470                 475                 480
Gly Gln Pro Met Cys Val Leu Leu Tyr Tyr His Asp Leu Met Asn Arg
                485                 490                 495
Lys Gly Lys Met Ser
            500

<210> SEQ ID NO 39
<211> LENGTH: 520
<212> TYPE: PRT
<213> ORGANISM: Arabidopsis thaliana (AtDGAT)

<400> SEQUENCE: 39

Met Ala Ile Leu Asp Ser Ala Gly Val Thr Thr Val Thr Glu Asn Gly
1               5                   10                  15
Gly Gly Glu Phe Val Asp Leu Asp Arg Leu Arg Arg Arg Lys Ser Arg
                20                  25                  30
Ser Asp Ser Ser Asn Gly Leu Leu Leu Ser Gly Ser Asp Asn Asn Ser
            35                  40                  45
Pro Ser Asp Asp Val Gly Ala Pro Ala Asp Val Arg Asp Arg Ile Asp
        50                  55                  60
Ser Val Val Asn Asp Asp Ala Gln Gly Thr Ala Asn Leu Ala Gly Asp
65                  70                  75                  80
Asn Asn Gly Gly Gly Asp Asn Asn Gly Gly Arg Gly Gly Gly Glu
                85                  90                  95
Gly Arg Gly Asn Ala Asp Ala Thr Phe Thr Tyr Arg Pro Ser Val Pro
            100                 105                 110
Ala His Arg Arg Ala Arg Glu Ser Pro Leu Ser Ser Asp Ala Ile Phe
        115                 120                 125
Lys Gln Ser His Ala Gly Leu Phe Asn Leu Cys Val Val Val Leu Ile
    130                 135                 140
Ala Val Asn Ser Arg Leu Ile Ile Glu Asn Leu Met Lys Tyr Gly Trp
145                 150                 155                 160
```

Leu Ile Arg Thr Asp Phe Trp Phe Ser Ser Arg Ser Leu Arg Asp Trp
            165                 170                 175

Pro Leu Phe Met Cys Cys Ile Ser Leu Ser Ile Phe Pro Leu Ala Ala
            180                 185                 190

Phe Thr Val Glu Lys Leu Val Leu Gln Lys Tyr Ile Ser Glu Pro Val
            195                 200                 205

Val Ile Phe Leu His Ile Ile Thr Met Thr Glu Val Leu Tyr Pro
210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
            245                 250                 255

His Thr Ser Tyr Asp Ile Arg Ser Leu Ala Asn Ala Ala Asp Lys Ala
            260                 265                 270

Asn Pro Glu Val Ser Tyr Tyr Val Ser Leu Lys Ser Leu Ala Tyr Phe
            275                 280                 285

Met Val Ala Pro Thr Leu Cys Tyr Gln Pro Ser Tyr Pro Arg Ser Ala
            290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
            325                 330                 335

Val Arg Asn Ser Lys His Pro Leu Lys Gly Asp Leu Leu Tyr Ala Ile
            340                 345                 350

Glu Arg Val Leu Lys Leu Ser Val Pro Asn Leu Tyr Val Trp Leu Cys
            355                 360                 365

Met Phe Tyr Cys Phe Phe His Leu Trp Leu Asn Ile Leu Ala Glu Leu
            370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
            405                 410                 415

Met Val Arg His Ile Tyr Phe Pro Cys Leu Arg Ser Lys Ile Pro Lys
            420                 425                 430

Thr Leu Ala Ile Ile Ile Ala Phe Leu Val Ser Ala Val Phe His Glu
            435                 440                 445

Leu Cys Ile Ala Val Pro Cys Arg Leu Phe Lys Leu Trp Ala Phe Leu
450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
            485                 490                 495

Cys Ile Phe Gly Gln Pro Met Cys Val Leu Leu Tyr Tyr His Asp Leu
            500                 505                 510

Met Asn Arg Lys Gly Ser Met Ser
            515                 520

<210> SEQ ID NO 40
<211> LENGTH: 526
<212> TYPE: PRT
<213> ORGANISM: Vernicia fordii (VfDGAT)

<400> SEQUENCE: 40

Met Thr Ile Pro Glu Thr Pro Asp Asn Ser Thr Asp Ala Thr Thr Ser
1               5                   10                  15

Gly Gly Ala Glu Ser Ser Ser Asp Leu Asn Leu Ser Leu Arg Arg Arg
            20                  25                  30

Arg Thr Ala Ser Asn Ser Asp Gly Ala Val Ala Glu Leu Ala Ser Lys
            35                  40                  45

Ile Asp Glu Leu Glu Ser Asp Ala Gly Gly Gln Val Ile Lys Asp
    50                  55                  60

Pro Gly Ala Glu Met Asp Ser Gly Thr Leu Lys Ser Asn Gly Lys Asp
65                  70                  75                  80

Cys Gly Thr Val Lys Asp Arg Ile Glu Asn Arg Glu Asn Arg Gly Gly
                85                  90                  95

Ser Asp Val Lys Phe Thr Tyr Arg Pro Ser Val Pro Ala His Arg Ala
                100                 105                 110

Leu Lys Glu Ser Pro Leu Ser Ser Asp Asn Ile Phe Lys Gln Ser His
            115                 120                 125

Ala Gly Leu Phe Asn Leu Cys Ile Val Val Leu Val Ala Val Asn Ser
            130                 135                 140

Arg Leu Ile Ile Glu Asn Ile Met Lys Tyr Gly Trp Leu Ile Lys Thr
145                 150                 155                 160

Gly Phe Trp Phe Ser Ser Arg Ser Leu Arg Asp Trp Pro Leu Leu Met
                165                 170                 175

Cys Cys Leu Thr Leu Pro Ile Phe Ser Leu Ala Ala Tyr Leu Val Glu
                180                 185                 190

Lys Leu Ala Cys Arg Lys Tyr Ile Ser Ala Pro Thr Val Val Phe Leu
            195                 200                 205

His Ile Leu Phe Ser Ser Thr Ala Val Leu Tyr Pro Val Ser Val Ile
            210                 215                 220

Leu Ser Cys Glu Ser Ala Val Leu Ser Gly Val Ala Leu Met Leu Phe
225                 230                 235                 240

Ala Cys Ile Val Trp Leu Lys Leu Val Ser Tyr Ala His Thr Asn Phe
                245                 250                 255

Asp Met Arg Ala Ile Ala Asn Ser Val Asp Lys Gly Asp Ala Leu Ser
                260                 265                 270

Asn Ala Ser Ser Ala Glu Ser Ser His Asp Val Ser Phe Lys Ser Leu
            275                 280                 285

Val Tyr Phe Met Val Ala Pro Thr Leu Cys Tyr Gln Pro Ser Tyr Pro
            290                 295                 300

Arg Thr Ala Ser Ile Arg Lys Gly Trp Val Val Arg Gln Phe Val Lys
305                 310                 315                 320

Leu Ile Ile Phe Thr Gly Phe Met Gly Phe Ile Ile Glu Gln Tyr Ile
                325                 330                 335

Asn Pro Ile Val Gln Asn Ser Gln His Pro Leu Lys Gly Asp Leu Leu
            340                 345                 350

Tyr Ala Ile Glu Arg Val Leu Lys Leu Ser Val Pro Asn Leu Tyr Val
            355                 360                 365

Trp Leu Cys Met Phe Tyr Cys Phe Phe His Leu Trp Leu Asn Ile Leu
            370                 375                 380

Ala Glu Leu Leu Arg Phe Gly Asp Arg Glu Phe Tyr Lys Asp Trp Trp
385                 390                 395                 400

Asn Ala Arg Thr Val Glu Glu Tyr Trp Arg Met Trp Asn Met Pro Val
                405                 410                 415

His Lys Trp Met Val Arg His Ile Tyr Phe Pro Cys Leu Arg His Lys
                420                 425                 430

Ile Pro Arg Gly Val Ala Leu Leu Ile Thr Phe Phe Val Ser Ala Val

```
                435              440              445
Phe His Glu Leu Cys Ile Ala Val Pro Cys His Ile Phe Lys Leu Trp
    450                  455                  460

Ala Phe Ile Gly Ile Met Phe Gln Ile Pro Leu Val Gly Ile Thr Asn
465                  470                  475                  480

Tyr Leu Gln Asn Lys Phe Arg Ser Ser Met Val Gly Asn Met Ile Phe
                485                  490                  495

Trp Phe Ile Phe Cys Ile Leu Gly Gln Pro Met Cys Leu Leu Leu Tyr
                500                  505                  510

Tyr His Asp Leu Met Asn Arg Lys Gly Thr Thr Glu Ser Arg
                515                  520                  525

<210> SEQ ID NO 41
<211> LENGTH: 521
<212> TYPE: PRT
<213> ORGANISM: Ricinus communis (RcDGAT)

<400> SEQUENCE: 41

Met Thr Ile Leu Glu Thr Pro Glu Thr Leu Gly Val Ile Ser Ser Ser
1               5                   10                  15

Ala Thr Ser Asp Leu Asn Leu Ser Leu Arg Arg Arg Thr Ser Asn
                20                  25                  30

Asp Ser Asp Gly Ala Leu Ala Asp Leu Ala Ser Lys Phe Asp Asp Asp
            35                  40                  45

Asp Asp Val Arg Ser Glu Asp Ser Ala Glu Asn Ile Ile Glu Asp Pro
        50                  55                  60

Val Ala Ala Val Thr Glu Leu Ala Thr Ala Lys Ser Asn Gly Lys Asp
65                  70                  75                  80

Cys Val Ala Asn Ser Asn Lys Asp Lys Ile Asp Ser His Gly Gly Ser
                85                  90                  95

Ser Asp Phe Lys Leu Ala Tyr Arg Pro Ser Val Pro Ala His Arg Ser
            100                 105                 110

Leu Lys Glu Ser Pro Leu Ser Ser Asp Leu Ile Phe Lys Gln Ser His
        115                 120                 125

Ala Gly Leu Phe Asn Leu Cys Ile Val Val Leu Val Ala Val Asn Ser
130                 135                 140

Arg Leu Ile Ile Glu Asn Leu Met Lys Tyr Gly Trp Leu Ile Lys Thr
145                 150                 155                 160

Gly Phe Trp Phe Ser Ser Arg Ser Leu Arg Asp Trp Pro Leu Phe Met
                165                 170                 175

Cys Cys Leu Ser Leu Pro Val Phe Pro Leu Ala Ala Tyr Leu Val Glu
            180                 185                 190

Lys Ala Ala Tyr Arg Lys Tyr Ile Ser Pro Pro Ile Val Ile Phe Leu
        195                 200                 205

His Val Ile Ile Thr Ser Ala Ala Val Leu Tyr Pro Ala Ser Val Ile
    210                 215                 220

Leu Ser Cys Glu Ser Ala Phe Leu Ser Gly Val Thr Leu Met Glu Leu
225                 230                 235                 240

Ala Cys Met Val Trp Leu Lys Leu Val Ser Tyr Ala His Thr Asn Tyr
                245                 250                 255

Asp Met Arg Ala Ile Ala Asp Thr Ile His Lys Glu Asp Ala Ser Asn
            260                 265                 270

Ser Ser Ser Thr Glu Tyr Cys His Asp Val Ser Phe Lys Thr Leu Ala
        275                 280                 285

Tyr Phe Met Val Ala Pro Thr Leu Cys Tyr Gln Pro Ser Tyr Pro Arg
```

```
                290                 295                 300
Thr Ala Phe Ile Arg Lys Gly Trp Val Phe Arg Gln Phe Val Lys Leu
305                 310                 315                 320

Ile Ile Phe Thr Gly Phe Met Gly Phe Ile Ile Glu Gln Tyr Ile Asn
                325                 330                 335

Pro Ile Val Gln Asn Ser Gln His Pro Leu Lys Gly Asp Leu Leu Tyr
                340                 345                 350

Ala Ile Glu Arg Val Leu Lys Leu Ser Val Pro Asn Leu Tyr Val Trp
                355                 360                 365

Leu Cys Leu Phe Tyr Cys Phe Phe His Leu Trp Leu Asn Ile Val Ala
370                 375                 380

Glu Leu Leu Arg Phe Gly Asp Arg Glu Phe Tyr Lys Asp Trp Trp Asn
385                 390                 395                 400

Ala Lys Thr Val Glu Glu Tyr Trp Arg Met Trp Asn Met Pro Val His
                405                 410                 415

Lys Trp Met Val Arg His Ile Tyr Phe Pro Cys Leu Arg Lys Ile
                420                 425                 430

Pro Arg Gly Val Ala Ile Val Ile Ala Phe Phe Val Ser Ala Val Phe
                435                 440                 445

His Glu Leu Cys Ile Ala Val Pro Cys His Met Phe Lys Leu Trp Ala
450                 455                 460

Phe Phe Gly Ile Met Phe Gln Ile Pro Leu Val Val Ile Thr Asn Tyr
465                 470                 475                 480

Phe Gln Arg Lys Phe Arg Ser Ser Met Val Gly Asn Met Ile Phe Trp
                485                 490                 495

Phe Phe Phe Cys Ile Leu Gly Gln Pro Met Cys Val Leu Leu Tyr Tyr
                500                 505                 510

His Asp Leu Met Asn Arg Asp Gly Asn
                515                 520

<210> SEQ ID NO 42
<211> LENGTH: 532
<212> TYPE: PRT
<213> ORGANISM: Nicotiana tabacum (NtDGAT)

<400> SEQUENCE: 42

Met Val Ile Met Glu Leu Pro Glu Ser Val Glu Met Thr Thr Thr Thr
1               5                   10                  15

Thr Thr Ser Gly Ile Glu Asn Leu Asn Ser Asp Leu Asn His Ser Val
                20                  25                  30

Arg Arg Arg Arg Gly Ser Asn Gly Phe Glu Ala Ala Ser Ala Ile Asn
                35                  40                  45

Ser Ser Asp Ala Asn Met Ser Glu Asp Arg Arg Asp Val Cys Gly Ser
                50                  55                  60

Gly Ala Gly Leu Glu Thr Val Asn Glu Arg Ser Lys Ser Val Gly Glu
65                  70                  75                  80

Ser Ser Asp Val Ile Arg Lys Glu Asp Arg Asn Asp Asn Val Ala
                85                  90                  95

Asn Gly Glu Glu Ser Lys Ser Thr Glu Thr Thr Thr Pro Phe Lys
                100                 105                 110

Phe Ala Tyr Arg Ala Ser Ala Pro Ala His Arg Ile Lys Glu Ser
                115                 120                 125

Pro Leu Ser Ser Asp Ala Ile Phe Lys Gln Ser His Ala Gly Leu Phe
130                 135                 140

Asn Leu Cys Val Val Val Leu Ile Ala Val Asn Ser Arg Leu Ile Ile
```

```
            145                 150                 155                 160
        Glu Asn Leu Met Lys Tyr Gly Leu Leu Ile Arg Ala Gly Phe Trp Phe
                        165                 170                 175

Ser Ser Lys Ser Leu Arg Asp Trp Pro Leu Leu Met Cys Cys Leu Ser
                        180                 185                 190

Leu Gln Ile Leu Pro Leu Ala Ala Phe Leu Val Glu Lys Leu Ala Gln
                        195                 200                 205

Gln Arg His Leu Thr Glu Arg Ala Val Val Thr Leu His Ile Thr Ile
                        210                 215                 220

Thr Thr Ala Ala Ile Leu Tyr Pro Val Leu Val Ile Leu Gly Cys Asp
        225                 230                 235                 240

Ser Ala Phe Leu Phe Gly Val Ile Leu Met Leu Val Ala Cys Ile Val
                        245                 250                 255

Trp Met Lys Leu Val Ser Tyr Ala His Thr Asn His Asp Met Arg Gln
                        260                 265                 270

Leu Ala Lys Ser Thr Asp Lys Asp Glu Thr Ser Asp Gly Asp Phe Ser
                        275                 280                 285

Tyr Asp Val Ser Phe Lys Ser Leu Ala Tyr Phe Met Val Ala Pro Thr
                        290                 295                 300

Leu Cys Tyr Gln Leu Ser Tyr Pro His Thr Pro Cys Ile Arg Lys Gly
        305                 310                 315                 320

Trp Val Ala Arg Gln Phe Ile Lys Leu Val Ile Phe Thr Gly Leu Met
                        325                 330                 335

Gly Phe Ile Ile Glu Gln Tyr Ile Asn Pro Ile Val Gln Asn Ser Gln
                        340                 345                 350

His Pro Leu Lys Gly Asn Leu Leu Tyr Ala Ile Glu Arg Val Leu Lys
                        355                 360                 365

Leu Ser Val Pro Asn Leu Tyr Val Trp Leu Cys Met Phe Tyr Cys Phe
                        370                 375                 380

Phe His Leu Trp Leu Asn Ile Leu Ala Glu Leu Leu Cys Phe Gly Asp
        385                 390                 395                 400

Arg Glu Phe Tyr Lys Asp Trp Trp Asn Ala Lys Thr Ile Asp Glu Tyr
                        405                 410                 415

Trp Arg Met Trp Asn Met Pro Val His Lys Trp Met Val Arg His Ile
                        420                 425                 430

Tyr Phe Pro Cys Leu Arg Asn Gly Ile Pro Lys Gly Val Ala Ile Leu
                        435                 440                 445

Ile Ala Phe Leu Val Ser Ala Val Phe His Glu Leu Cys Ile Ala Val
                        450                 455                 460

Pro Cys Arg Leu Phe Lys Trp Trp Ala Phe Met Gly Ile Met Phe Gln
        465                 470                 475                 480

Val Pro Leu Val Ile Leu Thr Asn Phe Leu Gln Asn Lys Phe Gln Ser
                        485                 490                 495

Ser Met Val Gly Asn Met Met Phe Trp Cys Phe Phe Cys Ile Leu Gly
                        500                 505                 510

Gln Pro Met Cys Val Leu Leu Tyr Tyr His Asp Val Met Asn Arg Lys
                        515                 520                 525

Ser Ser Ala Arg
        530
```